(12) United States Patent
LaRossa

(10) Patent No.: US 8,940,511 B2
(45) Date of Patent: Jan. 27, 2015

(54) YEAST STRAIN FOR PRODUCTION OF FOUR CARBON ALCOHOLS

(71) Applicant: Butamax™ Advanced Biofuels LLC, Wilmington, DE (US)

(72) Inventor: Robert A. LaRossa, Chadds Ford, PA (US)

(73) Assignee: Butamax Advanced Biofuels LLC DE (US)

( * ) Notice: Subject to any disclaimer, the term of this patent is extended or adjusted under 35 U.S.C. 154(b) by 0 days.

(21) Appl. No.: 13/756,841

(22) Filed: Feb. 1, 2013

(65) Prior Publication Data

US 2013/0130342 A1 May 23, 2013

Related U.S. Application Data

(62) Division of application No. 12/435,530, filed on May 5, 2009, now Pat. No. 8,389,252.

(60) Provisional application No. 61/052,286, filed on May 12, 2008, provisional application No. 61/052,289, filed on May 12, 2008.

(51) Int. Cl.
*C12P 7/16* (2006.01)
*C12N 1/19* (2006.01)

(52) U.S. Cl.
USPC ........................................ 435/160; 435/254.2

(58) Field of Classification Search
USPC .............................................. 435/160, 254.2
See application file for complete search history.

(56) References Cited

U.S. PATENT DOCUMENTS

| 5,192,673 | A | 3/1993 | Jain et al. |
|---|---|---|---|
| 6,358,717 | B1 | 3/2002 | Blaschek et al. |
| 6,960,465 | B1 | 11/2005 | Papoutsakis et al. |
| 2007/0092957 | A1 | 4/2007 | Donaldson et al. |
| 2007/0259410 | A1 | 11/2007 | Donaldson et al. |
| 2007/0259411 | A1 | 11/2007 | Bramucci et al. |
| 2007/0292927 | A1 | 12/2007 | Donaldson et al. |
| 2008/0124774 | A1 | 5/2008 | Bramucci et al. |
| 2008/0138870 | A1 | 6/2008 | Bramucci et al. |
| 2008/0182308 | A1 | 7/2008 | Donaldson et al. |
| 2009/0155870 | A1 | 6/2009 | Donaldson et al. |
| 2009/0162911 | A1 | 6/2009 | LaRossa et al. |
| 2009/0203097 | A1 | 8/2009 | Flint et al. |
| 2009/0203139 | A1 | 8/2009 | LaRossa et al. |
| 2009/0288337 | A1 | 11/2009 | Picataggio et al. |

OTHER PUBLICATIONS

Ashe et al., "A Novel eIF2B-Dependent Mechanism of Translational Control in Yeast as a Response to Fusel Alcohols", The EMBO Journal Nov. 15, 2001, vol. 20, No. 22, pp. 6464-6474.

(Continued)

*Primary Examiner* — Rosanne Kosson

(57) ABSTRACT

Yeast cells with a reduced general control response to amino acid starvation were found to have increased tolerance to butanol in the growth medium. The reduced response was engineered by genetic modification of a gene involved in the response, a GCN gene, to eliminate activity of the encoded protein. Yeast strains with an engineered butanol biosynthetic pathway and a genetic modification in a gene involved in the general control response to amino acid starvation, which have increased butanol tolerance, are useful for production of butanol.

13 Claims, 4 Drawing Sheets

(56) References Cited

OTHER PUBLICATIONS

Bieszkiewicz et al., "Studies on the Resistance of Activated Sludge Bacteria to High Concentrations of Methanol, Butanol, Glycol, Cyclohexanone and Cyclohexylamine, Acta Microbiologica Polonica", 1987, pp. 259-265, vol. 36, No. 3.
Bode et al., "Occurrence of the General Control of Amino Acid Biosynthesis in Yeast", J. Basic Microbiol, vol. 30, pp. 31-35, (1990).
Brachmann et al., "Designer Deletion Strains Derived From *Saccharomyces cerevisiae* S288C: A Useful Set of Strains and Plasmids for PCR-Mediated Gene Disruption and Other Applications", Yeast, vol. 14, pp. 115-132, (1998).
Desmond, C. et al., "Improved Stress Tolerance of GroESL-Overproducing *Lactococcus lactis* and Probiotic Lactobacillus paracasei NFBC 338", Applied and Environmental Microbiology, Oct. 2004, pp. 5929-5936, vol. 70, No. 10, American Society for Microbiology.
Dickinson et al., "An Investigation of the Metabolism of Valine to Isobutyl Alcohol in *Saccharomyces cerevisiae*", The Journal of Biological Chemistry, Oct. 2, 1998, pp. 25751-25756, vol. 273, No. 40, the American Society for Biochemistry and Molecular Biology, Inc.
Giaever et al., "Functional Profiling of the *Saccharomyces cerevisiae* Genome", Nature Publishing Group, vol. 418, pp. 387-391, (2002).
Girbal et al., "Regulation of solvent production in *Clostridium acetobutylicum*", Trends in Biotechnology, 1998, pp. 11-16, vol. 16, Elsevier Science Ltd.
Hannig et al., "Molecular Analysis of GCN3, A Translational Activator of GCN4: Evidence for Posttranslational Control of GCN3 Regulatory Function", Molecular and Cellular Biology, vol. 8, No. 11, 1988, pp. 4808-4820.
Hinnebusch, "Translational Regulation of GCN4 and the General Amino Acid Control of Yeast", Annual Review of Microbiology, pp. 407-450, (2005).
Hinnebusch, "Mechanisms of Gene Regulation in the General Control of Amino Acid Biosynthesis in *Saccharonmyces-cerevisiae*", Microbiological Reviews, vol. 52, No. 2, 1988, pp. 248-273.
International Preliminary Report on Patentability for corresponding application No. PCT/US2009/043275 mailed Nov. 25, 2010.
International Search Report for corresponding application No. PCT/US2009/043275 mailed Aug. 3, 2009.
Paluh et al., "The Cross-Pathway Control Gene of *Neurospora crassa*, CPC-1, Encodes a Protein Similar to GCN4 of Yeast and the DNA-Binding Domain of the Oncogene V-Jun-Encoded Protein", Proc. Natl. Acad. Sci., vol. 85, pp. 3728 - 3732, USA (1988).
Quratulain, S. et al., "Development and Characterization of Butanol-Resistant Strain of *Clostridium acetobutylicum* in Molasses Medium", Folia Microbiolgica, 1995, pp. 467-471, vol. 40, No. 5.
Sardessai et al., "Organic solvent-tolerant bacteria in mangrove ecosystem", Current Science, Mar. 25, 2002, pp. 622-623, vol. 82, No. 6.
Soucaille et al., 'Butanol Tolerance and AUtobacterioein Production by *Clostridium aceobutylicum*, Current Microbiology, 1987, pp. 295-29, vol. 14.
Stewart, "A Chemist'S Perspective on the Use of Genetically Engineered Microbes as Reagents for Organic Synthesis", Biotechnology and Genetic Reviews, vol. 14, pp. 67-143, (1997).
Tomas et al., "Overexpression of groESL in *Clostridium acetobutylicum* Results in Increased Solvent Production and Tolerance, Prolonged Metabolism, and Changes in the Cell's Transcriptional Program", Applied and Environmental Microbiology, Aug. 2003, pp. 4951-4965, vol. 69, No. 8, American Society for Microbiology.
Winzeler et al., "Functional Characterization of the *S. cerevisiae* Genome by Gene Deletion and Paralles Analysis", Science vol. 285, pp. 901-906 (1999).

YEAST STRAIN FOR PRODUCTION OF FOUR CARBON ALCOHOLS

CROSS-REFERENCE TO RELATED APPLICATIONS

This application is a divisional of and claims the benefit of U.S. application Ser. No. 12/435,530, filed May 5, 2009, which claims the benefit of U.S. Provisional Applications 61/052,286 and 61/052,289, both filed May 12, 2008. Each of the referenced applications is herein incorporated by reference.

FIELD OF INVENTION

The invention relates to the field of microbiology and genetic engineering. More specifically, yeast genes involved in response to butanol were identified. Yeast strains with reduced expression of the identified genes were found to have improved growth yield in the presence of butanol.

BACKGROUND OF INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known, however these processes use starting materials derived from petrochemicals, are generally expensive, and are not environmentally friendly. Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Isobutanol is produced biologically as a by-product of yeast fermentation. It is a component of "fusel oil" that forms as a result of incomplete metabolism of amino acids by this group of fungi. Isobutanol is specifically produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273(40):25752-25756 (1998)). Yields of fusel oil and/or its components achieved during beverage fermentation are typically low.

Additionally, recombinant microbial production hosts, expressing a 1-butanol biosynthetic pathway (Donaldson et al., copending and commonly owned U.S. Patent Application Publication No. 20080182308), a 2-butanol biosynthetic pathway (Donaldson et al., copending and commonly owned U.S. Patent Application Publication Nos. US 20070259410A1 and US 2007-0292927), and an isobutanol biosynthetic pathway (Maggio-Hall et al., copending and commonly owned U.S. Patent Application Publication No. US 20070092957) have been described.

Biological production of butanols is believed to be limited by butanol toxicity to the host microorganism used in fermentation for butanol production. Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., *Current Microbiology* 14(5):295-299 (1987)). Desmond et al. (*Appl. Environ. Microbiol.* 70(10): 5929-5936 (2004)) report that overexpression of GroESL, two stress responsive proteins, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) has been described. Butanol tolerant bacterial strains have been isolated from microbial consortia (copending and commonly owned U.S. Patent Publication Nos. 20070259411, 20080124774 and 20080138870) or by mutant screening (copending and commonly owned U.S. patent application Ser. Nos. 12/330,530, 12/330,531, and 12/330,534).

There remains a need for butanol producing yeast strains that are more tolerant to butanols, as well as methods of producing butanols using yeast host strains that are more tolerant to these chemicals and engineered for butanol production.

SUMMARY OF THE INVENTION

The invention provides a recombinant yeast host which produces butanol and comprises a genetic modification that results in reduced response in the general control response to amino acid starvation. Such cells have an increased tolerance to butanol as compared with cells that lack the genetic modification. Reduction in response in the general control response to amino acid starvation may be accomplished via mutation of endogenous genes that impact the response. Host cells of the invention may produce butanol naturally or may be engineered to do so via an engineered pathway.

Accordingly, the invention provides a recombinant yeast host cell producing butanol where the yeast cell comprises at least one genetic modification which reduces the response in the general control response to amino acid starvation.

In one embodiment the yeast cell of the invention comprises a genetic modification in a gene encoding a protein selected from Gcn1p, Gcn2p, Gcn3p, Gcn4p, Gcn5p, and Gcn20p.

In another embodiment the yeast cell comprises a recombinant biosynthetic pathway selected from the group consisting of:
  a) a 1-butanol biosynthetic pathway;
  b) a 2-butanol biosynthetic pathway; and
  c) an isobutanol biosynthetic pathway.

In another embodiment the invention provides a method for the production of butanol comprising the steps of:
  (a) providing a recombinant yeast host cell which
     1) produces butanol and
     2) comprises at least one genetic modification which reduces the response in the general control response to amino acid starvation; and
  (b) culturing the strain of (a) under conditions wherein butanol is produced.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 1A:
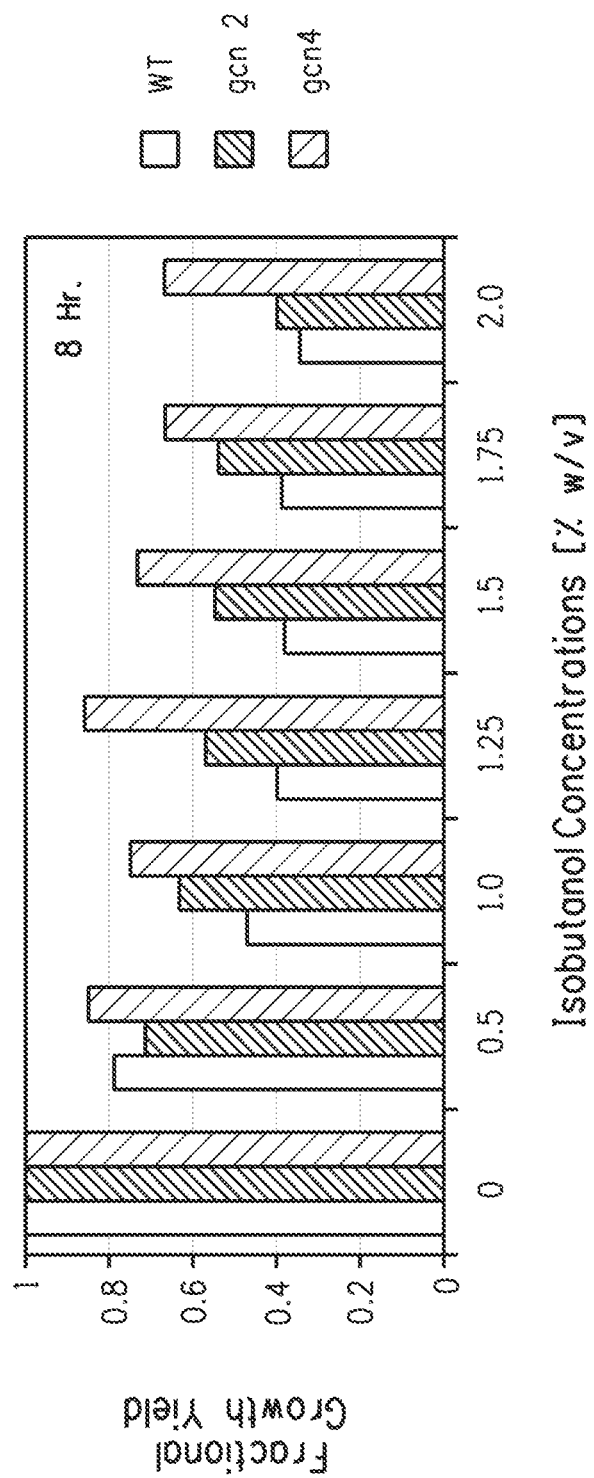
FIG. 1 shows fractional growth yields of wild type, mutant GCN2 and mutant GCN4 strains at 8 hr (A) and 24 hr (B) time points for growth in YVCM containing different concentrations of isobutanol.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from *Clostridium acetobutylicum* ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATCC 824 | 15 | 16 |

TABLE 2

Summary of Gene and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 872 | 27 | 28 |

TABLE 2-continued

Summary of Gene and Protein SEQ ID Numbers for 2-Butanol Biosynthetic Pathway

| Description | SEQ ID NO: Nucleic acid | SEQ ID NO: Peptide |
|---|---|---|
| sadH, 2-butanol dehydrogenase from *Rhodococcus* ruber 219 | 29 | 30 |

TABLE 3

Summary of Gene and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of Gene and Protein SEQ ID Numbers for members of general control system for amino acid biosynthesis

| Description | SEQ ID NO: Nucleic acid | SEQ ID NO: Peptide |
|---|---|---|
| GCN1 from *Saccharomyces cerevisiae* | 49 | 50 |
| GCN2 from *Saccharomyces cerevisiae* | 51 | 52 |
| GCN3 from *Saccharomyces cerevisiae* | 53 | 54 |
| GCN4 from *Saccharomyces cerevisiae* | 55 | 56 |
| GCN5 from *Saccharomyces cerevisiae* | 57 | 58 |
| GCN20 from *Saccharomyces cerevisiae* | 59 | 60 |
| GCN1 from *Yarrowia lipolytica* | 61 | 62 |
| GCN2 from *Yarrowia lipolytica* | 63 | 64 |
| GCN3 from *Yarrowia lipolytica* | 65 | 66 |
| GCN5 from *Yarrowia lipolytica* | 67 | 68 |
| GCN2 from *Candida albicans* | 69 | 70 |
| GCN3 from *Candida albicans* | 71 | 72 |
| GCN5 from *Candida albicans*-1 | 73 | 74 |
| GCN5 from *Candida albicans*-2 | 75 | 74* |

*the same amino acid sequence is encoded by both SEQ ID NO: 73 and 75

SEQ ID NO:76 is the nucleotide sequence of the GPD promoter described in Example 2.

SEQ ID NO:77 is the nucleotide sequence of the CYC1 terminator described in Example 2.

SEQ ID NO:78 is the nucleotide sequence of the FBA promoter described in Example 2.

SEQ ID NO:79 is the nucleotide sequence of ADH1 promoter described in Example 2.

SEQ ID NO:80 is the nucleotide sequence of ADH1 terminator described in Example 2.

SEQ ID NO:81 is the nucleotide sequence of GPM promoter described in Example 2.

SEQ ID NOs:82-137 are the nucleotide sequences of oligonucleotide cloning, screening or sequencing primers used in the Examples described herein.

SEQ ID NO:138 is the nucleotide sequence of the "URA3 repeats" fragment.

SEQ ID NOs:139 and 140 are the nucleotide sequences of PCR primers used to amplify a DNA fragment for gcn2 deletion.

SEQ ID NOs:141 and 142 are the nucleotide sequences of PCR primers used to amplify a DNA fragment for gcn4 deletion.

SEQ ID NOs:143 and 144 are primer binding sequences that bound direct repeats flanking URA3$^+$: in the "URA3 repeats" fragment. SEQ ID NOs:145 and 146 are direct repeat sequences that flank the promoter and coding sequence in the "URA3 repeats" fragment.

SEQ ID NO:147 is the promoter sequence in the "URA3 repeats" fragment.

SEQ ID NO:148 is the URA3 coding sequence in the "URA3 repeats" fragment.

DETAILED DESCRIPTION OF THE INVENTION

The present invention provides a recombinant yeast host which produces butanol and comprises a genetic modification that results in a reduced response in the general control response to amino acid starvation. Such cells have an increased tolerance to butanol as compared with cells that lack the genetic modification. A tolerant yeast strain of the invention has at least one genetic modification that causes the reduced general control response to amino acid starvation. This reduced response may be accomplished via mutation of endogenous genes that impact the response. Host cells of the invention may produce butanol naturally or may be engineered to do so via an engineered pathway.

Butanol produced using the present strains may be used as an alternative energy source to fossil fuels. Fermentative production of butanol results in less pollutants than typical petrochemical synthesis.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The terms "butanol tolerant yeast strain" and "tolerant" when used to describe a modified yeast strain of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZAADY01000001, *Alcaligenes eutrophus* (GenBank NOs: YP_294481, NC_007347), and *A. eutrophus* (Gen Bank NOs: P14697, J04981).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19)).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. mari-*

*paludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "carbon substrate" means a carbon contain compound useful as an energy source of a yeast and may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

A "cell having a reduced response in the general control response to amino acid starvation" refers herein to a cell that does not sense uncharged tRNA as a signal for induction of transcription of amino acid biosynthetic genes, and/or it does not respond to amino acid starvation by inducing transcription of amino acid biosynthetic genes (Hinnebusch (2005) *Ann. Rev. Microbiol.* 59:407-450).

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, 2nd ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputinq: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.*, 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191 (1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 70%, 75%, 80%, 85%, 90%, or 95%, or any integer percentage from 70% to 100% may be useful in describing the present invention, such as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments encode polypeptides with the above identities and typically encode a polypeptide having at least about 250 amino acids, preferably at least 300 amino acids, and most preferably at least about 348 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.*, 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.*, 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular alcohol dehydrogenase proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The invention encompasses more than the specific exemplary sequences because it is well known in the art that alterations in an amino acid sequence or in a coding region wherein a chemically equivalent amino acid is substituted at a given site, which does not effect the functional properties of the encoded protein, are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Thus coding regions with the described codon variations, and proteins with the described amino acid variations are encompassed in the present invention.

Standard recombinant DNA and molecular cloning techniques used here are well known in the art and are described by Sambrook, J., Fritsch, E. F. and Maniatis, *T. Molecular Cloning: A Laboratory Manual*, 2$^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987. Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

General Control Response Target Genes for Engineering Butanol Tolerance in Yeast The invention relates to the discovery that reducing expression of a gene involved in the general control response to amino acid starvation in *Saccharomyces cerevisiae* results in increased tolerance of cells to butanol. The general control response to amino acid starvation in yeast is a complex system that senses the presence of uncharged tRNAs and responds by inducing transcription of amino acid biosynthetic genes. This control system (reviewed in Hinebusch (2005) *Ann. Rev. Microbiol.* 59: 407-450) includes genes that when mutated confer sensitivity to a wide range of amino acid antagonists and analogs; these genes were called general control non-depressible, or GCN, for the mutant phenotype of not responding to amino acid starvation.

For example, GCN2 encodes a protein (Gcn2p) which senses uncharged tRNA and binds to ribosomes via one Gcn2p domain, the carboxy-terminal domain. Uncharged tRNA is sensed by a second internal domain of Gcn2p termed His RS (for histidyl-tRNA synthetase like). This binding of uncharged tRNA to the HRS domain results in yet another Gcn2p domain (PK) kinasing eukaryotic initiation factor 2 that is associated with GDP (eIF2~GDP) producing eIF2-P~GDP. In turn, eIF2-P~GDP stimulates translation of the GCN4 encoded mRNA and Gcn4p (the GCN4 encoded protein) activates expression of many genes involved in amino acid biosynthesis.

Initiation of translation requires an activated form of an initiation factor, eIF2: eIF2~GTP. This activated form presents the initiating tRNA, finet-tRNA, to the ribosome. eIF2-finet-tRNA~GTP normally starts translation by binding to ribosomes where eventually eIF2~GDP is released. This form of the initiation factor is inactive and must be activated by exchange of GTP for GDP producing eIF2-GTP. When Gcn2p's kinase is activated, eIF2~GDP is hijacked yielding eIF2~P. This form, eIF2~P, blocks the Guanine Exchange Factor eIF2B from catalyzing the reaction: eIF2~GDP+ GTP->eIF2~GTP +GDP. Thus most translational initiation is retarded while translation of Gcn4p, the transcriptional activator of amino acid biosynthetic genes, is increased.

Additional GCN gene encoded proteins involved in the general control response to amino acid starvation system in *Saccharomyces cerevisiae* include:

Gcn1p: a positive regulator of the Gcn2p kinase activity
Gcn3p: alpha subunit of the translation initiation factor eIF2B, a positive regulator of GCN4 expression
Gcn5p: histone acetyltransferase, acetylates N-terminal lysines on histones $H_2B$ and H3; catalytic subunit of the ADA and SAGA histone acetyltransferase complexes
Gcn6p: positive regulator of GCN4 transcription
Gcn7p: positive regulator of GCN4 transcription
Gcn8p: role undefined
Gcn9p: role undefined
Gcn20p: positive regulator of Gcn2p kinase activity, forms a complex with Gcn1p Given in Table 4 are the SEQ ID NOs for the *Saccharomyces cerevisiae* Gcn1-5p and Gcn20p proteins and their coding regions. Also given in Table 4 are representative coding regions and proteins for GCN genes of *Yarrowia lipolytica* and *Candida albicans*.

A mutation that reduces or eliminates expression of a protein involved in the general control response to amino acid starvation in yeast will reduce the response and surprisingly provide an increase in butanol tolerance. Thus the present yeast host has a genetic modification reducing activity of at least one protein involved in the general control response to amino acid starvation. Suitable genes for genetic modification to reduce the general control response to amino acid starvation include genes encoding Gcn1p, Gcn2p, Gcn3p, Gcn4p, Gcn5p, Gcn6p, Gcn7p, Gcn8p, Gcn9p, and Gcn20p. Examples of these proteins are given in Table 4 as SEQ ID NOS:50, 52, 54, 56, 58, 60, 62, 64, 66, 68, 70, 72, and 74. Genes encoding proteins with sequence identities of at least about 80%, 85%, 90%, 95% or more to these proteins and having GCN activity may be targets for genetic modification to reduce the general control response to amino acid starvation. More suitable targets are genes encoding Gcn1p, Gcn2p, Gcn3p, Gcn4p, Gcn5p, and Gcn20p. Most suitable targets are genes encoding Gcn2p and Gcn4p.

Any yeast gene identified as encoding a Gcn1p, Gcn2p, Gcn3p, Gcn4p, Gcn5p, Gcn6p, Gcn7p, Gcn8p, Gcn9p, or Gcn20p protein, or other gene encoding a protein involved in the general control response to amino acid starvation, is a target gene for modification in the corresponding yeast strain to create a strain of the present invention with increased butanol tolerance. Any type of yeast having a GCN system may be engineered for butanol tolerance using the method of the present invention. Yeast genera including *Saccharomyces, Yarrowia, Candida*, and *Hansenula* have GCN systems (Bode et al. (199) J. Basic. Microbiol. 30(1):31-5) and examples of GCN genes of *Saccharomyces cerevisiae, Yarrowia lipolytica*, and *Candida albicans* which are targets for modification to provide tolerance are listed in Table 4. Examples of GCN encoded proteins of *Saccharomyces cerevisiae* include SEQ ID NOs:50, 52, 54, 56, 58, and 60. Examples of GCN encoded proteins of *Yarrowia lipolytica* include SEQ ID NOs:62, 64, 66, and 68. Examples of GCN encoded proteins of *Candida albicans* include SEQ ID NOs:70, 72, and 74. In addition, homologs of GCN2 and GCN4 have been found in the mold *Neurospora crassa* (Paluh et al. (1988) *Proc. Natl. Acad. Sci. USA* 85(11):3728-3732).

Other GCN system target genes may be identified in the literature and in bioinformatics databases well known to the skilled person. Additionally, the sequences described herein or those recited in the art may be used to identify other homologs in nature. For example each of the GCN nucleic acid fragments described herein may be used to isolate genes encoding homologous proteins from the same or other yeasts. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, genes encoding similar proteins or polypeptides to the GCN genes described herein could be isolated directly by using all or a portion of the instant nucleic acid fragments as DNA hybridization probes to screen libraries from any desired yeast using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency. Heterologous genes may also be identified using functional selections as illustrated by complementation selection for GCN function described in Paluh et al. (ibid.).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described GCN sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Alternatively, because GCN sequences are well known, and because sequencing of the genomes of fungi is prevalent (10 are completed, 71 others have been subjected to a whole genome shotgun approach and are being assembled while 42 others are in progress), suitable GCN system target genes may be identified on the basis of sequence similarity using bioinformatics approaches alone, which are well known to one skilled in the art.

Genetic Modification of General Control Response Genes in Yeast for Butanol Tolerance Many methods for genetic modification of target genes are known to one skilled in the art and may be used to create the present yeast strains. Modifications that may be used to reduce or eliminate expression of a target protein are disruptions that include, but are not limited to, deletion of the entire gene or a portion of the gene encoding a Gcnp, inserting a DNA fragment into a GCN gene (in either the promoter or coding region) so that the protein is not expressed or expressed at lower levels, introducing a mutation into a GCn coding region which adds a stop codon or frame shift such that a functional protein is not expressed, and introducing one or more mutations into a GCN coding region to alter amino acids so that a non-functional or a less enzymatically active protein is expressed. In addition, expression of a GCN gene may be blocked by expression of an antisense RNA or an interfering RNA, and constructs may be introduced that result in cosuppression. Moreover, a GCN gene may be synthesized whose expression is low because rare codons are substituted for plentiful ones, and this gene substituted for the endogenous corresponding GCN gene. Such a gene will produce the same polypeptide but at a lower rate. In addition, the synthesis or stability of the transcript may be lessened by mutation. Similarly the efficiency by which a protein is translated from mRNA may be modulated by mutation. All of these methods may be readily practiced by one skilled in the art making use of the known sequences encoding Gcn proteins. Yeast GCN sequences are publicly available, and representative sequences are listed in Table 4. One skilled in the art may choose specific modification strategies to eliminate or lower the expression of a GCN gene as desired to increase butanol tolerance.

DNA sequences surrounding a GCN coding sequence are also useful in some modification procedures and are available for yeasts such as for *Saccharomycse cerevisiae* in the complete genome sequence coordinated by Genome Project ID9518 of Genome Projects coordinated by NCBI (National Center for Biotechnology Information) with identifying GOPID #13838. Additional examples of yeast genomic sequences include that of *Yarrowia lipolytica*, GOPIC #13837, and of *Candida albicans*, which is included in GPID #10771, #10701 and #16373. Other yeast genomic sequences can be readily found by one of skill in the art in publicly available databases.

In particular, DNA sequences surrounding a GCN coding sequence are useful for modification methods using homologous recombination. For example, in this method GCN gene flanking sequences are placed bounding a selectable marker gene to mediate homologous recombination whereby the marker gene replaces the GCN gene. Also partial GCN gene sequences and GCN flanking sequences bounding a selectable marker gene may be used to mediate homologous recombination whereby the marker gene replaces a portion of the target GCN gene. In addition, the selectable marker may be bounded by site-specific recombination sites, so that following expression of the corresponding site-specific recombinase, the resistance gene is excised from the GCN gene without reactivating the latter. The site-specific recombination leaves behind a recombination site which disrupts expression of the Gcn protein. The homologous recombination vector may be constructed to also leave a deletion in the GCN gene following excision of the selectable marker, as is well known to one skilled in the art.

Deletions may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence (as described in Methods in Enzymology, v194, pp 281-301 (1991)).

Moreover, promoter replacement methods may be used to exchange the endogenous transcriptional control elements allowing another means to modulate expression such as described in Mnaimneh et al. ((2004) Cell 118(1):31-44).

Butanol Tolerance of the Present Modified Yeast Strain

A yeast strain of the present invention that is genetically modified for reduced response in the general control response for amino acid starvation has improved tolerance to butanol. The tolerance of reduced response strains may be assessed by assaying their growth in concentrations of butanol that are detrimental to growth of the parental (prior to genetic modification) strains. Improved tolerance is to butanol compounds including 1-butanol, isobutanol, and 2-butanol. The amount of tolerance observed will vary depending on the inhibiting chemical and its concentration, growth conditions, growth period, and the specific genetically modified strain. For example, as shown in Example 1 herein, improved tolerance was observed with growth in 1%-2% isobutanol for 8 hours in a medium lacking amino acids other than histidine and leucine. In this medium the cells have more biosynthetic demand than is the case in rich medium, which contains histidine and leucine. Other conditions for demonstration of the improved butanol tolerance of the present yeast strains include conditions where biosynthetic demand is higher than in rich medium conditions, including a lack of any metabolic product, such as other amino acids, nucleotides, or fatty acids. Additionally the presence of inhibitors, osmotic imbalance, or other non-ideal growth conditions may provide conditions for demonstration of improved butanol tolerance.

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other.

The butanol biosynthetic pathway may be a 1-butanol, 2-butanol, or isobutanol biosynthetic pathway. Particularly suitable yeast hosts for the production of butanol and modification of the general control response to amino acid starvation for increased butanol tolerance include, but are not limited to, members of the genera *Saccharomyces*, *Candida*, *Hansenula* and *Yarowia*. Preferred hosts include *Saccharomyces cerevesiae*, *Candida albicans* and *Yarowia lipolytica*.

1-Butanol Biosynthetic Pathway

A biosynthetic pathway for the production of 1-butanol is described by Donaldson et al. in co-pending and commonly owned U.S. Patent Application Publication No. 0080182308, incorporated herein by reference. This biosynthetic pathway comprises the following substrate to product conversions:
a) acetyl-CoA to acetoacetyl-CoA, as catalyzed for example by acetyl-CoA acetyltransferase with protein sequence such as SEQ ID NO:2, 4 or 40 encoded by the genes given as SEQ ID NO:1, 3 or 39;
b) acetoacetyl-CoA to 3-hydroxybutyryl-CoA, as catalyzed for example by 3-hydroxybutyryl-CoA dehydrogenase with protein sequence such as SEQ ID NO:6 encoded by the gene given as SEQ ID NO:5;
c) 3-hydroxybutyryl-CoA to crotonyl-CoA, as catalyzed for example by crotonase with protein sequence such as SEQ ID NO:8 encoded by the gene given as SEQ ID NO:7;
d) crotonyl-CoA to butyryl-CoA, as catalyzed for example by butyryl-CoA dehydrogenase with protein sequence such as SEQ ID NO:10 encoded by the gene given as SEQ ID NO:9;
e) butyryl-CoA to butyraldehyde, as catalyzed for example by butyraldehyde dehydrogenase with protein sequence such as SEQ ID NO:12 encoded by the gene given as SEQ ID NO:11; and
f) butyraldehyde to 1-butanol, as catalyzed for example by 1-butanol dehydrogenase with protein sequence such as SEQ ID NO:14 or 16 encoded by the genes given as SEQ ID NO:13 or 15.

The pathway requires no ATP and generates $NAD^+$ and/or $NADP^+$, thus, it balances with the central, metabolic routes that generate acetyl-CoA.

2-Butanol Biosynthetic Pathway

Biosynthetic pathways for the production of 2-butanol are described by Donaldson et al. in co-pending and commonly owned U.S. Patent Application Publication Nos. 20070259410 and 20070292927, each incorporated herein by reference. One 2-butanol biosynthetic pathway comprises the following substrate to product conversions:
a) pyruvate to alpha-acetolactate, as catalyzed for example by acetolactate synthase with protein sequence such as SEQ ID NO:20 encoded by the gene given as SEQ ID NO:19;
b) alpha-acetolactate to acetoin, as catalyzed for example by acetolactate decarboxylase with protein sequence such as SEQ ID NO:18 encoded by the gene given as SEQ ID NO:17;

c) acetoin to 2,3-butanediol, as catalyzed for example by butanediol dehydrogenase with protein sequence such as SEQ ID NO:22 encoded by the gene given as SEQ ID NO:21;

d) 2,3-butanediol to 2-butanone, catalyzed for example by butanediol dehydratase with protein sequence such as SEQ ID NO:24, 26, or 28 encoded by genes given as SEQ ID NO:23, 25, or 27; and e) 2-butanone to 2-butanol, as catalyzed for example by 2-butanol dehydrogenase with protein sequence such as SEQ ID NO:30 encoded by the gene given as SEQ ID NO:29.

Isobutanol Biosynthetic Pathway

Biosynthetic pathways for the production of isobutanol are described by Maggio-Hall et al. in copending and commonly owned U.S. Patent Application Publication No. 20070092957, incorporated herein by reference. One isobutanol biosynthetic pathway comprises the following substrate to product conversions:

a) pyruvate to acetolactate, as catalyzed for example by acetolactate synthase with protein sequence such as SEQ ID NO:20 or 42 encoded by genes given as SEQ ID NO:19 or 41;

b) acetolactate to 2,3-dihydroxyisovalerate, as catalyzed for example by acetohydroxy acid isomeroreductase with protein sequence such as SEQ ID NO:32, 44 or 46 encoded by genes given as SEQ ID NO:31, 43 or 45;

c) 2,3-dihydroxyisovalerate to α-ketoisovalerate, as catalyzed for example by acetohydroxy acid dehydratase with protein sequence such as SEQ ID NO:34 encoded by the gene given as SEQ ID NO:33; or dihydroxyacid dehydratase with protein sequence such as SEQ ID NO:48 encoded by the gene given as SEQ ID NO:47;

d) α-ketoisovalerate to isobutyraldehyde, as catalyzed for example by a branched-chain keto acid decarboxylase with protein sequence such as SEQ ID NO:36 encoded by the gene given as SEQ ID NO:35; and e) isobutyraldehyde to isobutanol, as catalyzed for example by a branched-chain alcohol dehydrogenase with protein sequence such as SEQ ID NO:38 encoded by the gene given as SEQ ID NO:37.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48.

Methods for gene expression in yeasts are known in the art; specifically, basic yeast molecular biology protocols including transformation, cell growth, gene expression, gap repair recombination, etc. are described in *Methods in Enzymology*, Volume 194, *Guide to Yeast Genetics and Molecular and Cell Biology (Part A*, 2004, Christine Guthrie and Gerald R. Fink (Eds.), Elsevier Academic Press, San Diego, Calif. Expression of a gene in yeast typically requires a promoter, followed by the coding region of interest, and a transcriptional terminator, all of which are operably linked to provide expression cassettes. A number of yeast promoters can be used in constructing expression cassettes for genes encoding a butanol biosynthetic pathway, including, but not limited to constitutive promoters FBA, GPD, and GPM, and the inducible promoters GAL1, GAL10, and CUP1. Suitable transcriptional terminators include, but are not limited to FBAt, GPDt, GPMt, ERG10t, and GAL1t. For example, suitable promoters, transcriptional terminators, and the genes of a 1-butanol or isobutanol biosynthetic pathway may be cloned into *E. coli-yeast* shuttle vectors, as described in Example 2.

Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). These vectors allow strain propagation in both *E. coli* and yeast strains. Typical hosts for gene cloning and expression include a yeast haploid strain BY4741 (MATa his3Δ1 leu2Δ0 met15Δ0 ura3Δ0) (Research Genetics, Huntsville, Ala., also available from ATCC 201388) and a diploid strain BY4743 (MATa/alpha his3Δ1/his3Δ1 leu2Δ0/leu2Δ0 lys2Δ0/LYS2 MET15/met15Δ0 ura3Δ0/ura3Δ0) (Research Genetics, Huntsville, Ala., also available from ATCC 201390). Construction of expression vectors for genes encoding butanol biosynthetic pathway enzymes may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≥21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis. Yeast transformants of positive plasmids are grown for performing enzyme assays to characterize the activities of the enzymes expressed by the genes of interest.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1Compd., [Int. Symp.]*, 7th (1993), 415-32. Editor(s): Murrell, J. Collin; Kelly, Don P. Publisher: Intercept, Andover, UK). Similarly, various species of *Candida* will metabolize alanine or oleic acid (Sutter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and Methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotech-* nology: A Textbook of Industrial Microbiology, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Microbial strains were obtained from The American Type Culture Collection (ATCC), Manassas, Va., unless otherwise noted.

Methods for Determining Isobutanol Concentration in Culture Media

The concentration of isobutanol in the culture media can be determined by a number of methods known in the art. For example, a specific high performance liquid chromatography (HPLC) method utilizes a Shodex SH-1011 column with a Shodex SH-G guard column, both purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions described. Alternatively, gas chromatography (GC) methods are available. For example, a specific GC method utilizes an HP-INNOWax column (30 m×0.53 mm id, 1 µm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature ias 45° C. for 1 min, 45 to 220° C. at 10° C./min, and 220° C. for 5 min; and FID detection is employed at 240° C. with 26 mL/min helium makeup gas. The retention time of isobutanol is 4.5 min.

The meaning of abbreviations is as follows: "s" means second(s), "min" means minute(s), "h" means hour(s), "psi" means pounds per square inch, "nm" means nanometers, "d" means day(s), "µL" means microliter(s), "mL" means milliliter(s), "L" means liter(s), "mm" means millimeter(s), "nm" means nanometers, "mM" means millimolar, "µM" means micromolar, "M" means molar, "mmol" means millimole(s), "µmol" means micromole(s)", "g" means gram(s), "µg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography. The term "molar selectivity" is the number of moles of product produced per mole of sugar substrate consumed and is reported as a percent.

Example 1

Butanol tolerance in qcn2 and qcn4 mutants

GCN2 gene and GCN4 gene deletion mutants of the diploid a/αSaccharomyces cerevisiae strain BY4743 (Brachmann et al. (Yeast 14:115-132 (1998)) are available in a nearly complete, ordered deletion strain collection (Giaever et al. Nature 418, 387-391 (2002); Saccharomyces Genome Deletion Project). Cells of the GCN2 gene and GCN4 gene deletion mutants were grown overnight from a single colony on a YPD plate in either YPD or YVCM medium (recipes below) in a 14 ml Falcon tube at 30° C. with shaking at 250 rpm. Overnight cultures were diluted 1:100 (2 ml to 200 ml) in the same medium and growth was monitored every 60 minutes until 1 doubling had occurred. At that point the cultures were split into 25 ml samples that were dispensed to separate 125 ml plastic flasks. Challenging concentrations of isobutanol ranging between 0.5% and 2% w/v were added to all but one flask of each culture that served as the positive control. Control and challenge cultures were incubated with shaking in a 30° C. water bath and absorbance was monitored on about an hourly basis.

The two media used were a rich medium, YPD, which contains per liter: 10 g yeast extract, 20 g peptone, 20 g dextrose; and a defined, synthetic medium, YVCM, which contains per liter: 6.67 g yeast nitrogen base without amino acids but with ammonium sulfate, 20 g dextrose, 20 mg L-histidine, 30 mg L-leucine, 20 mg uracil.

Figure 1B:
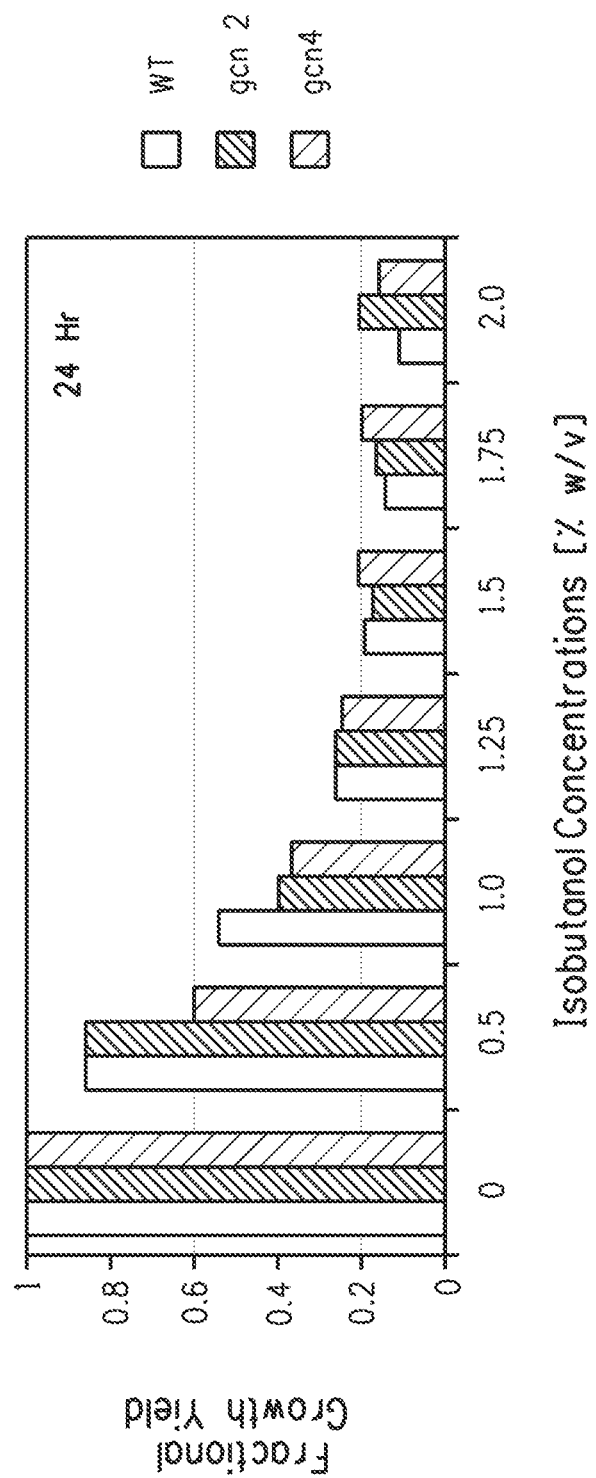

Using 8 and 24 hr time points for growth in YVCM containing isobutanol, fractional growth yields were determined and results are given in FIG. 1. Both GCN2 and GCN4 deletion lines that were grown in the synthetic medium were substantially more tolerant to an 8 hr isobutanol challenge than the parental strain. The accrued advantage disappeared after overnight incubation. The increased tolerance was seen over a 1-2% isobutanol concentration range.

Figure 2A:
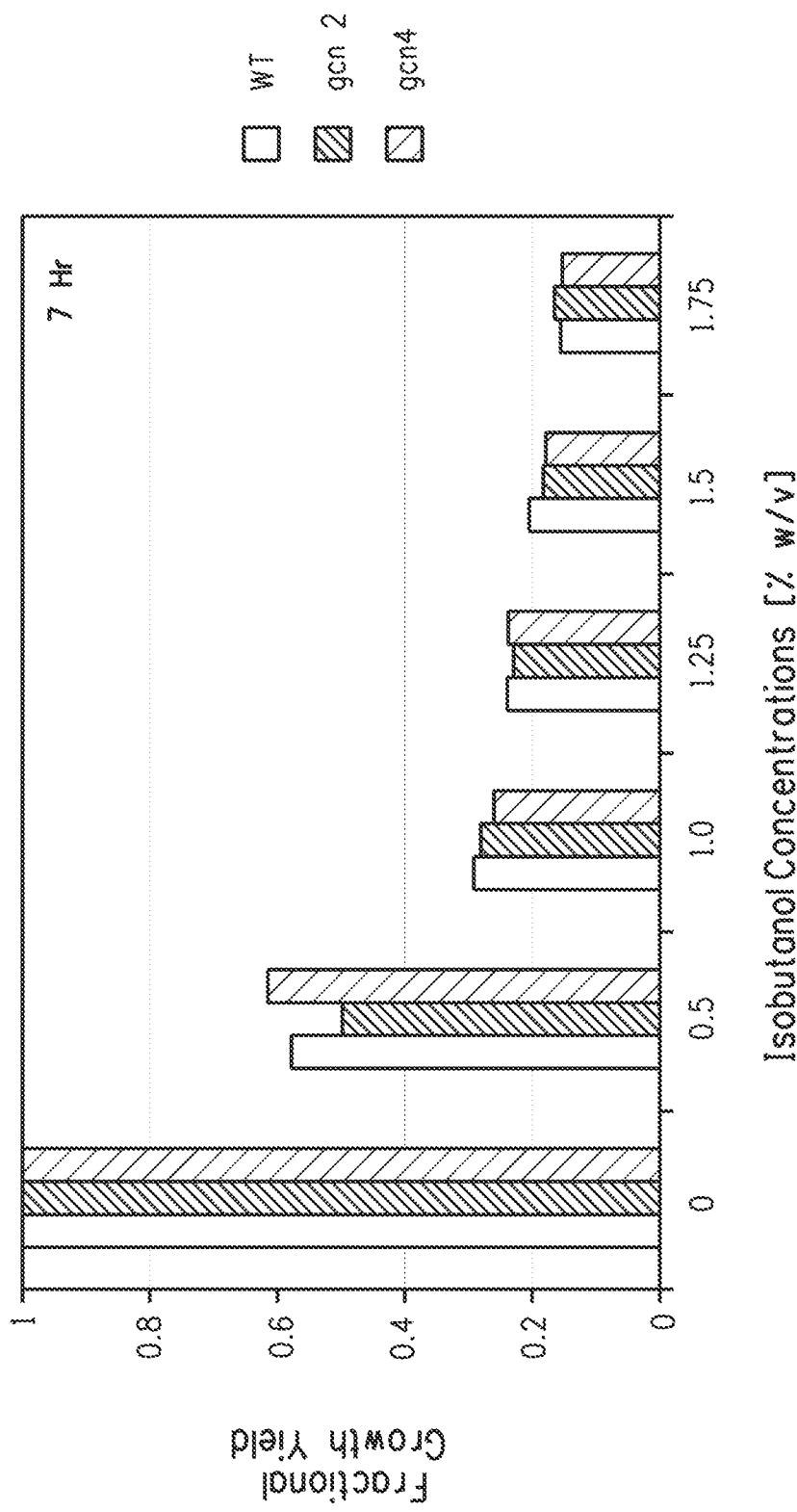
FIG. 2 shows fractional growth yields of wild type, mutant GCN2 and mutant GCN4 strains at 7 hr (A) and 23 hr (B) time points for growth in YPD containing different concentrations of isobutanol.
Figure 2B:
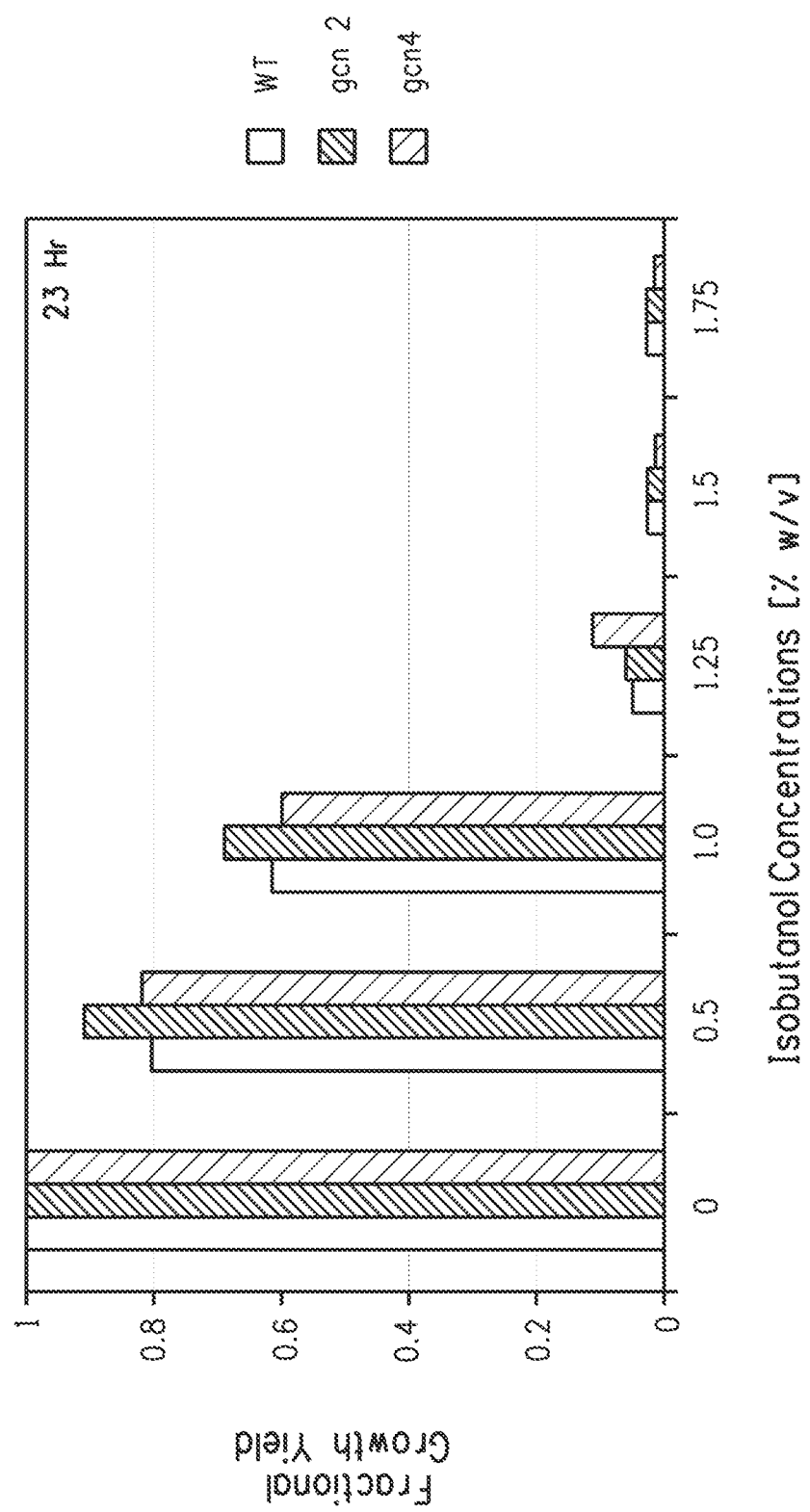

Using 7 and 23 hr time points for growth in YPD containing isobutanol, fractional growth yields were determined and results are given in FIG. 2. In these conditions improved tolerance was not observed at the short time point, and minimal improvement was seen with the GCN2 and GCN4 mutations in different isobutanol concentrations.

Example 2

Expression of Isobutanol Pathway Genes in Saccharomyces Cerevisiae

To express isobutanol pathway genes in Saccharomyces cerevisiae, a number of E. coli-yeast shuttle vectors were constructed. A PCR approach (Yu, et al. Fungal Genet. Biol. 41:973-981 (2004)) was used to fuse genes with yeast promoters and terminators. Specifically, the GPD promoter (SEQ ID NO:76) and CYC1 terminator (SEQ ID NO:77) were fused to the alsS gene from Bacillus subtilis (SEQ ID NO:41), the FBA promoter (SEQ ID NO:78) and CYC1 terminator were fused to the ILV5 gene from S. cerevisiae (SEQ ID NO:43), the ADH1 promoter (SEQ ID NO:79) and ADH1 terminator (SEQ ID NO:80) were fused to the ILV3 gene from S. cerevisiae (SEQ ID NO:47), and the GPM promoter (SEQ ID NO:81) and ADH1 terminator were fused to the kivD gene from Lactococcus lactis (SEQ ID NO:35). The primers, given in Table 5, were designed to include restriction sites for cloning promoter/gene/terminator products into E. coli-yeast shuttle vectors from the pRS400 series (Christianson et al. Gene 110:119-122 (1992)) and for exchanging promoters between constructs. Primers for the 5' ends of ILV5 and ILV3 (N138 and N155, respectively, given as SEQ ID NOs: 92 and 104, respectively) generated new start codons to eliminate mitochondrial targeting of these enzymes.

All fused PCR products were first cloned into pCR4-Blunt by TOPO cloning reaction (Invitrogen) and the sequences were confirmed (using M13 forward and reverse primers (Invitrogen) and the sequencing primers provided in Table 5. Two additional promoters (CUP1 and GAL1) were cloned by TOPO reaction into pCR4-Blunt and confirmed by sequencing; primer sequences are indicated in Table 5. The plasmids that were constructed are described in Table 6. The plasmids were transformed into either Saccharomyces cerevisiae BY4743 (ATCC 201390) or YJR148w (ATCC 4036939) to assess enzyme specific activities. For the determination of enzyme activities, cultures were grown to an OD$_{600}$ of 1.0 in synthetic complete medium (*Methods in Yeast Genetics*, 2005, Cold Spring Harbor Laboratory Press, Cold Spring Harbor, N.Y., pp. 201-202) lacking any metabolite(s) necessary for selection of the expression plasmid(s), harvested by centrifugation (2600×g for 8 min at 4° C.), washed with buffer, centrifuged again, and frozen at −80° C. The cells were thawed, resuspended in 20 mM Tris-HCl, pH 8.0 to a final volume of 2 mL, and then disrupted using a bead beater with 1.2 g of glass beads (0.5 mm size). Each sample was processed on high speed for 3 minutes total (with incubation on ice after each minute of beating). Extracts were cleared of cell debris by centrifugation (20,000×g for 10 min at 4° C.).

Acetolactate synthase activity in the cell free extracts is measured using the method described by Bauerle et al. (*Biochim. Biophys. Acta* 92(1):142-149 (1964)). Acetohydroxy acid reductoisomerase activity in the cell free extracts is measured using the method described by Arlin and Umbarger (*J. Biol. Chem.* 244(5):1118-1127 (1969)). Acetohydroxy acid dehydratase activity in the cell free extracts is measured using the method described by Flint et al. (*J. Biol. Chem.* 268(20): 14732-14742 (1993)). Branched-chain keto acid decarboxylase activity in the cell free extracts is measured using the method described by Smit et al. (*Appl. Microbiol. Biotechnol.* 64:396-402 (2003)), except that Purpald® reagent (Aldrich, Catalog No. 162892) is used to detect and quantify the aldehyde reaction products.

TABLE 5

Primer Sequences for Cloning and Sequencing of
S. cerevisiae Expression Vectors

| Name | Sequence | Description | SEQ ID NO: |
|---|---|---|---|
| N98SeqF1 | CGTGTTAGTCACATCAGGAC | *B. subtilis* alsS sequencing primer | 82 |
| N98SeqF2 | GGCCATAGCAAAAATCCAAACAGC | *B. subtilis* alsS sequencing primer | 83 |
| N98SeqF3 | CCACGATCAATCATATCGAACACG | *B. subtilis* alsS sequencing primer | 84 |
| N98SeqF4 | GGTTTCTGTCTCTGGTGACG | *B. subtilis* alsS sequencing primer | 85 |
| N99SeqR1 | GTCTGGTGATTCTACGCGCAAG | *B. subtilis* alsS sequencing primer | 86 |
| N99SeqR2 | CATCGACTGCATTACGCAACTC | *B. subtilis* alsS sequencing primer | 87 |
| N99SeqR3 | CGATCGTCAGAACAACATCTGC | *B. subtilis* alsS sequencing primer | 88 |
| N99SeqR4 | CCTTCAGTGTTCGCTGTCAG | *B. subtilis* alsS sequencing primer | 89 |
| N136 | CCGCGGATAGATCTGAAATGAATAACAATACTGACA | FBA promoter forward primer with SacII/BgIII sites | 90 |
| N137 | TACCACCGAAGTTGATTTGCTTCAACATCCTCAGCTCTAGATTTGAATATGTATTACTTGGTTAT | FBA promoter reverse primer with BbvCI site and ILV5-annealing region | 91 |
| N138 | ATGTTGAAGCAAATCAACTTCGGTGGTA | ILV5 forward primer (creates alternate start codon) | 92 |
| N139 | TTATTGGTTTTCTGGTCTCAAC | ILV5 reverse primer | 93 |
| N140 | AAGTTGAGACCAGAAAACCAATAATTAATTAATCATGTAATTAGTTATGTCACGCTT | CYC terminator forward primer with PacI site and ILV5-annealing region | 94 |
| N141 | GCGGCCGCCCGCAAATTAAAGCCTTCGAGC | CYC terminator reverse primer with NotI site | 95 |
| N142 | GGATCCGCATGCTTGCATTTAGTCGTGC | GPM promoter forward primer with BamHI site | 96 |
| N143 | CAGGTAATCCCCCACAGTATACATCCTCAGCTATTGTAATATGTGTGTTTGTTTGG | GPM promoter reverse primer with BbvCI site and kivD-annealing region | 97 |

TABLE 5-continued

Primer Sequences for Cloning and Sequencing of
S. cerevisiae Expression Vectors

| Name | Sequence | Description | SEQ ID NO: |
|---|---|---|---|
| N144 | ATGTATACTGTGGGGATTACC | kivD forward primer | 98 |
| N145 | TTAGCTTTTATTTTGCTCCGCA | kivD reverse primer | 99 |
| N146 | TTTGCGGAGCAAAATAAAAGCTAA TTAATTAAGAGTAAGCGAATTT CTTATGATTTA | ADH terminator forward primer with PacI site and kivD-annealing region | 100 |
| N147 | ACTAGTACCACAGGTGTTGTCCT CTGAG | ADH terminator reverse primer with SpeI site | 101 |
| N151 | CTAGAGAGCTTTCGTTTTCATG | alsS reverse primer | 102 |
| N152 | CTCATGAAAACGAAAGCTCTCTA GTTAATTAATCATGTAATTAGTTA TGTCACGCTT | CYC terminator forward primer with PacI site and alsS-annealing region | 103 |
| N155 | ATGGCAAAGAAGCTCAACAAGT ACT | ILV3 forward primer (alternate start codon) | 104 |
| N156 | TCAAGCATCTAAAACACAACCG | ILV3 reverse primer | 105 |
| N157 | AACGGTTGTGTTTTAGATGCTTG ATTAATTAAGAGTAAGCGAATTT CTTAGATTTA | ADH terminator forward primer with PacI site and ILV3-annealing region | 106 |
| N158 | GGATCCTTTTCTGGCAACCAAAC CCATA | ADH promoter forward primer with BamHI site | 107 |
| N159 | CGAGTACTTGTTGAGCTTCTTTG CCATCCTCAGCGAGATAGTTGA TTGTATGCTTG | ADH promoter reverse primer with BbvCI site and ILV3-annealing region | 108 |
| N160SeqF1 | GAAAACGTGGCATCCTCTC | FBA::ILV5::CYC sequencing primer | 109 |
| N160SeqF2 | GCTGACTGGCCAAGAGAAA | FBA::ILV5::CYC sequencing primer | 110 |
| N160SeqF3 | TGTACTTCTCCCACGGTTTC | FBA::ILV5::CYC sequencing primer | 111 |
| N160SeqF4 | AGCTACCCAATCTCTATACCCA | FBA::ILV5::CYC sequencing primer | 112 |
| N160SeqF5 | CCTGAAGTCTAGGTCCCTATTT | FBA::ILV5::CYC sequencing primer | 113 |
| N160SeqR1 | GCGTGAATGTAAGCGTGAC | FBA::ILV5::CYC sequencing primer | 114 |
| N160SeqR2 | CGTCGTATTGAGCCAAGAAC | FBA::ILV5::CYC sequencing primer | 115 |
| N160SeqR3 | GCATCGGACAACAAGTTCAT | FBA::ILV5::CYC sequencing primer | 116 |
| N160SeqR4 | TCGTTCTTGAAGTAGTCCAACA | FBA::ILV5::CYC sequencing primer | 117 |
| N160SeqR5 | TGAGCCCGAAAGAGAGGAT | FBA::ILV5::CYC sequencing primer | 118 |
| N161SeqF1 | ACGGTATACGGCCTTCCTT | ADH::ILV3::ADH sequencing primer | 119 |
| N161SeqF2 | GGGTTTGAAAGCTATGCAGT | ADH::ILV3::ADH sequencing primer | 120 |

TABLE 5-continued

Primer Sequences for Cloning and Sequencing of
S. cerevisiae Expression Vectors

| Name | Sequence | Description | SEQ ID NO: |
|---|---|---|---|
| N161SeqF3 | GGTGGTATGTATACTGCCAACA | ADH::ILV3::ADH sequencing primer | 121 |
| N161SeqF4 | GGTGGTACCCAATCTGTGATTA | ADH::ILV3::ADH sequencing primer | 122 |
| N161SeqF5 | CGGTTTGGGTAAAGATGTTG | ADH::ILV3::ADH sequencing primer | 123 |
| N161SeqF6 | AAACGAAAATTCTTATTCTTGA | ADH::ILV3::ADH sequencing primer | 124 |
| N161SeqR1 | TCGTTTTAAAACCTAAGAGTCA | ADH::ILV3::ADH sequencing primer | 125 |
| N161SeqR2 | CCAAACCGTAACCCATCAG | ADH::ILV3::ADH sequencing primer | 126 |
| N161SeqR3 | CACAGATTGGGTACCACCA | ADH::ILV3::ADH sequencing primer | 127 |
| N161SeqR4 | ACCACAAGAACCAGGACCTG | ADH:ILV3::ADH sequencing primer | 128 |
| N161SeqR5 | CATAGCTTTCAAACCCGCT | ADH::ILV3::ADH sequencing primer | 129 |
| N161SeqR6 | CGTATACCGTTGCTCATTAGAG | ADH::ILV3::ADH sequencing primer | 130 |
| N162 | ATGTTGACAAAAGCAACAAAAGA | alsS forward primer | 131 |
| N189 | ATCCGCGGATAGATCTAGTTCGAGTTTATCATTATCAA | GPD forward primer with SacII/BglII sites | 132 |
| N190.1 | TTCTTTTGTTGCTTTTGTCAACATCCTCAGCGTTTATGTGTGTTATTCGAAA | GPD promoter reverse primer with BbvCI site and alsS-annealing region | 133 |
| N176 | ATCCGCGGATAGATCTATTAGAAGCGCCGAGCGGGCG | GAL1 promoter forward primer with SacII/BglII sites | 134 |
| N177 | ATCCTCAGCTTTTCTCCTTGACGTTAAAGTA | GAL1 promoter reverse with BbvCI site | 135 |
| N191 | ATCCGCGGATAGATCTCCCATTACCGACATTTGGGCGC | CUP1 promoter forward primer with SacII/BglII sites | 136 |
| N192 | ATCCTCAGCGATGATTGATTGATTGATTGTA | CUP1 promoter reverse with BbvCI site | 137 |

TABLE 6

E. coli-Yeast Shuttle Vectors Carrying Isobutanol Pathway Genes

| Plasmid Name | Construction |
|---|---|
| pRS426 [ATCC No. 77107], URA3 selection | — |
| pRS426::GPD::alsS::CYC | GPD::alsS::CYC PCR product digested with SacII/NotI cloned into pRS426 digested with same |
| pRS426::FBA::ILV5::CYC | FBA::ILV5::CYC PCR product digested with SacII/NotI cloned into pRS426 digested with same |
| pRS425 [ATCC No. 77106], LEU2 selection | — |
| pRS425::ADH::ILV3::ADH | ADH::ILV3::ADH PCR product digested with BamHI/SpeI cloned into pRS425 digested with same |
| pRS425::GPM::kivD::ADH | GPM::kivD::ADH PCR product digested with BamHI/SpeI cloned into pRS425 digested with same |

TABLE 6-continued

E. coli-Yeast Shuttle Vectors Carrying Isobutanol Pathway Genes

| Plasmid Name | Construction |
| --- | --- |
| pRS426::CUP1::alsS | 7.7 kbp SacII/BbvCI fragment from pRS426::GPD::alsS::CYC ligated with SacII/BbvCI CUP1 fragment |
| pRS426::GAL1::ILV5 | 7 kbp SacII/BbvCI fragment from pRS426::FBA::ILV5::CYC ligated with SacII/BbvCI GAL1 fragment |
| pRS425::FBA::ILV3 | 8.9 kbp BamHI/BbvCI fragment from pRS425::ADH::ILV3::ADH ligated with 0.65 kbp BglII/BbvCI FBA fragment from pRS426::FBA::ILV5::CYC |
| pRS425::CUP1-alsS + FBA-ILV3 | 2.4 kbp SacII/NotI fragment from pRS426::CUP1::alsS cloned into pRS425::FBA::ILV3 cut with SacII/NotI |
| pRS426::FBA-ILV5 + GPM-kivD | 2.7 kbp BamHI/SpeI fragment from pRS425::GPM::kivD::ADH cloned into pRS426::FBA::ILV5::CYC cut with BamHI/SpeI |
| pRS426::GAL1-FBA + GPM-kivD | 8.5 kbp SacII/NotI fragment from pRS426:: FBA-ILV5 + GPM-kivD ligated with 1.8 kbp SacII/NotI fragment from pRS426::GAL1::ILV5 |
| pRS423 [ATCC No. 77104], HIS3 selection | — |
| pRS423::CUP1-alsS + FBA-ILV3 | 5.2 kbp SacI/SalI fragment from pRS425::CUP1-alsS + FBA-ILV3 ligated into pRS423 cut with SacI/SalI |
| pHR81 [ATCC No. 87541], URA3 and leu2-d selection | — |
| pHR81::FBA-ILV5 + GPM-kivD | 4.7 kbp SacI/BamHI fragment from pRS426::FBA-ILV5 + GPM-kivD ligated into pHR81 cut with SacI/BamHI |

Example 3

Prophetic

Production of Isobutanol Using Tolerant Saccharomyces cerevisiae Strain

The starting strain for this work is BY4741 (Brachmann, et al. Yeast. 14: 115-132 (1998)) and its Δbat2 derivative, YJR148W BY4741, mating type a (6939) available from the ATCC (#406939) with the genotype MATa his3delta1 leu2delta0 met15delta0 ura3delta0 deltaTWT2. bat2 encodes the cytosolic branched-chain amino acid aminotransferase, The deletion of bat2 in combination with the URA3 deletion allows growth in the absence of uracil to be used as a selection for the presence of a URA3 insertion.

First ΔGCN2 and ΔGCN4 derivatives are made using the ATCC strain #406939. This is accomplished by a gene replacement strategy commonly used in yeast in which a URA3+ allele is used as a selectable marker for a GCN insertion-deletion allele in which URA3+ is integrated in the genome along with flanking direct repeat sequences replacing the sequence targeted for deletion. Subsequently a recombination event between the direct repeats is selected by demanding fluoro-orotic acid (FOA) resistance which selects against URA3+ function.

The DNA fragment including a gene for URA3 expression and flanking direct repeats ("URA3 repeats" fragment; SEQ ID NO:138) includes the following (position numbers refer to position in the "URA3 repeats" fragment of SEQ ID NO:138):

1) primer binding sequences that bound the direct repeats flanking URA3+: gcattgcggattacgtattctaatg (position 1-25; SEQ ID NO:143) and gatgatacaacgagttagccaaggtg (position 1449-1474 of SEQ ID NO:144);
2) the direct repeat sequences that flank the promoter and coding sequence: ttcagcccgcggaacgccagcaaatcac-cacccatgcgcatgatactgagtcttgtacacgctgggcttcc agtg (position 26-100 of SEQ ID NO:145) and ttcagcccgcggaacgc-cagcaaatcaccacccatgcgcatgatactgagtcttgtacacgctgggcttcc agtg (position 1375-1449 of SEQ ID NO:146)
3) the promoter sequence:

```
tttttttattctttttttttgatttcggtttctttgaaattttttttgattc ggtaatctccgaacagaaggaagaacgaaggaaggagcacagacttaga ttggtatatatacgcatatgtagtgttgaagaaacatgaaattgcccag tattcttaacccaactgcacagaacaaaaacctgcaggaaacgaagata aatc (position 149-348 of SEQ ID NO: 147)
and
```

4) the coding region:

```
atgtcgaaagctacatataaggaacgtgctgctactcatcctagtcctg ttgctgccaagctatttaatatcatgcacgaaaagcaaacaaacttgtg tgcttcattggatgttcgtaccaccaaggaattactggagttagttgaa gcattaggtcccaaaatttgtttactaaaaacacatgtggatatcttga ctgattttccatggagggcacagttaagccgctaaaggcattatccgc caagtacaattttttactcttcgaagacagaaaatttgctgacattggt aatacagtcaaattgcagtactctgcgggtgtatacagaatagcagaat gggcagacattacgaatgcacacggtgtggtgggcccaggtattgttag cggtttgaagcaggcggcagaagaagtaacaaaggaacctagaggcctt ttgatgttagcagaattgtcatgcaagggctccctatctactggagaat atactaagggtactgttgacattgcgaagagcgacaaagattttgttat cggcttattgctcaaagagacatgggtggaagagatgaaggttacgat tggttgattatgacacccggtgtgggtttagatgacaagggagacgcat
```

-continued

```
tgggtcaacagtatagaaccgtggatgatgtggtctctacaggatctga cattattattgttggaagaggactatttgcaaagggaagggatgctaag gtagagggtgaacgttacagaaaagcaggctgggaagcatatttgagaa gatgcggccagcaaaactaa (position 349-1152 of SEQ ID

NO: 148).
```

A DNA fragment containing a 50 bp sequence that is 100 bp upstream of the GCN2 coding region, the URA3 repeats fragment described above, and a 50 bp sequence that is 100 bp downstream of the GCN2 coding region is prepared using PCR. The 5' primer is a chimeric sequence containing 50 bp of sequence upstream of GCN2 and the position 1-25 primer binding sequence above in (1): 50 (GCN2 5' flanking)+5' ura3 primer (I) (SEQ ID NO:139). The 3' primer is a chimeric sequence containing the complement of 50 bp of sequence downstream of GCN2 and the position 1449-1474 primer binding sequence complement: 50 (reverse compl of GCN2 3' flanking)+3' ura3 primer (reverse compl) (II) (SEQ ID NO:140).

The PCR reaction is a 50 µl reaction mixture of 1 µl of template DNA (50 ng total), 1 µl of each primer at 20 µM, 25 µl of 2× TaKaRa Ex Taq premix, 22 µl water. The template is pUC19-URA3 repeat, a pUC19 (Yanisch-Perron et al. (1985) Gene, 33:103-119) derivative into which the "URA3 repeat" has been inserted at the multi-cloning site. The PCR condition used is:
94° C. 1 min, then 30 cycles of 94° C. 20 sec, 55° C. 20 sec and 72° C. 2 min, followed by 7 min at 72° C. The extension time is 1 min per kb.

The resulting PCR product, a ΔGCN2::URA3$^+$ fragment, is purified using a Qiagen PCR purification kit.

A similar DNA fragment is prepared as above but using primers containing sequences upstream and downstream of the GCN4 coding region: 50 (GCN4 5' flanking)+5' ura3 primer (III) (SEQ ID NO:141) and 50 (reverse compl. of GCN4 3' flanking)+3' ura3 primer (reverse compl) (GCN4) (IV) (SEQ ID NO:142).

The resulting PCR product, a ΔGCN4::URA3$^+$ fragment, is purified using a Qiagen PCR purification kit.

The PCR products are used to transform the strain ATCC #406939. Integrants are selected for growth in the absence of uracil. Integrant strains with insertion of "URA3 repeats" and deletion of GCN2 or GCN4 are called, respectively:
DYW1: MATa his3delta1 leu2delta0 met15delta0 ura3delta0 deltaTWT2 Δgcn2::URA3$^+$ and
DYW2: MATa his3delta1 leu2delta0 met15delta0 ura3delta0 deltaTWT2 Δgcn4::URA3$^+$.

Using 5-FOA selection to select for elimination of the URA3$^+$ allele, strains with recombination between the direct repeats are obtained and called:
DYW3: MATa his3delta1 leu2delta0 met15delta0 ura3delta0 deltaTWT2 Δgcn2 and
DYW4: MATa his3delta1 leu2delta0 met15delta0 ura3delta0 deltaTWT2 Δgcn4

Plasmids pRS423::CUP1-alsS+FBA-ILV3 and pHR81::FBA-ILV5+ GPM-kivD (described in Example 2) are transformed into Saccharomyces cerevisiae DYW3 and DYW4 to produce strains DYW3 (Δgcn2)/pRS423::CUP1-alsS+FBA-ILV3/pHR81::FBA-ILV5+ GPM-kivD and DYW4 (Δgcn4)/pRS423::CUP1-alsS+FBA-ILV3/pHR81::FBA-ILV5+ GPM-kivD. A control strain is prepared by transforming vectors pRS423 and pHR81 (described in Example 2) into Saccharomyces cerevisiae (ATCC strain #406939) [strain 406939 (GCN2$^+$ GCN4$^+$)/pRS423/pHR811. Strains are maintained on standard S. cerevisiae synthetic complete medium (Methods in Yeast Genetics, 2005, Cold Spring Harbor Laboratory Press, Cold Spring Harbor, N.Y., pp. 201-202) containing either 2% glucose or sucrose but lacking uracil and histidine to ensure maintenance of plasmids.

For isobutanol production, cells are transferred to synthetic complete medium lacking uracil, histidine and leucine. Removal of leucine from the medium is intended to trigger an increase in copy number of the pHR81-based plasmid due to poor transcription of the leu2-d allele (Erhart and Hollenberg, J. Bacteriol. 156:625-635 (1983)). Aerobic cultures are grown in 175 mL capacity flasks containing 50 mL of medium in an Innova4000 incubator (New Brunswick Scientific, Edison, N.J.) at 30° C. and 200 rpm. Low oxygen cultures are prepared by adding 45 mL of medium to 60 mL serum vials that are sealed with crimped caps after inoculation and kept at 30° C. Sterile syringes are used for sampling and addition of inducer, as needed. Approximately 24 h after inoculation, the inducer CuSO$_4$ is added to a final concentration of 0.03 mM. Control cultures for each strain without CuSO$_4$ addition are also prepared. Culture supernatants are analyzed 18 or 19 h and 35 h after CuSO$_4$ addition by both HPLC (Shodex Sugar SH1011 column (Showa Denko America, Inc. NY) with refractive index (RI) detection) and GC (Varian CP-WAX 58(FFAP) CB, 0.25 mm×0.2 µm×25 m (Varian, Inc., Palo Alto, Calif.) with flame ionization detection (FID)) for isobutanol content, as described in the General Methods section. Production of isobutanol is enhanced by the presence of the mutant gcn alleles. In general, higher levels of isobutanol per optical density unit are produced by the GCN mutants.

What is claimed is:

1. A recombinant yeast host cell having the following characteristics:
   a) the yeast host cell produces a butanol when grown in a medium containing a carbon substrate;
   b) the yeast host cell comprises at least one genetic modification which reduces the response in the general control response to amino acid starvation, wherein the target for said genetic modification is a gene encoding the General Control Nonderepressible (Gcn) protein Gcn2p; and
   c) the yeast host cell comprises a recombinant biosynthetic pathway selected from the group consisting of:
      i) a 1-butanol biosynthetic pathway;
      ii) a 2-butanol biosynthetic pathway; and
      iii) an isobutanol biosynthetic pathway.

2. The yeast cell of claim 1, wherein the at least one genetic modification reduces production of Gcn2p.

3. The yeast cell of claim 2, wherein the at least one genetic modification is a disruption in an endogenous gene encoding.

4. The yeast cell of claim 1, wherein the cell is a member of the genus *Saccharomyces*.

5. The yeast of claim 1, where the cell is *Saccharomyces cerevisiae* comprising a disruption in an endogenous gene encoding.

6. The recombinant yeast cell of claim 1, wherein the host cell comprises an isobutanol biosynthetic pathway comprising:
   a) at least one gene encoding an acetolactate synthase;
   b) at least one gene encoding acetohydroxy acid isomeroreductase;
   c) at least one gene encoding acetohydroxy acid dehydratase;
   d) at least one gene encoding branched-chain keto acid decarboxylase; and
   e) at least one gene encoding branched-chain alcohol dehydrogenase.

7. A process for production of a butanol from recombinant yeast cell comprising:
   (a) providing the recombinant teast host cell of claim 1;
   (b) culturing the host cell of step (a), wherein the butanol is produced; and
   (c) recovering the butanol made in step (b).

8. The process of claim 7, wherein the host cell comprises an isobutanol biosynthetic pathway comprising:
   a) at least one gene encoding an acetolactate synthase;
   b) at least one gene encoding acetohydroxy acid isomeroreductase;
   c) at least one gene encoding acetohydroxy acid dehydratase;
   d) at least one gene encoding branched-chain keto acid decarboxylase; and
   e) at least one gene encoding branched-chain alcohol dehydrogenase.

9. The process of claim 7, wherein the at least one genetic modification reduces production of Gcn2p.

10. The recombinant yeast cell of claim 1, wherein the yeast cell comprises a 1-butanol biosynthetic pathway comprising:
    a) at least one gene encoding an acetyl-CoA acetyltransferase;
    b) at least one gene encoding a 3-hydroxybutyryl-CoA dehydrogenase;
    c) at least one gene encoding a crotonase;
    d) at least one gene encoding a butyryl-CoA dehydrogenase;
    e) at least one gene encoding a butyraldehyde dehydrogenase; and
    f) at least one gene encoding a 1-butanol dehydrogenase.

11. The recombinant yeast cell of claim 1, wherein the yeast cell comprises a 2-butanol biosynthetic pathway comprising:
    a) at least one gene encoding an acetolactate synthase;
    b) at least one gene encoding an acetolactate decarboxylase;
    c) at least one gene encoding a butanediol dehydrogenase;
    d) at least one gene encoding a butanediol dehydratase; and
    e) at least one gene encoding a 2-butanol dehydrogenase.

12. The process of claim 7, wherein the yeast host cell comprises a 1-butanol biosynthetic pathway comprising:
    a) at least one gene encoding an acetyl-CoA acetyltransferase;
    b) at least one gene encoding a 3-hydroxybutyryl-CoA dehydrogenase;
    c) at least one gene encoding a crotonase;
    d) at least one gene encoding a butyryl-CoA dehydrogenase;
    e) at least one gene encoding a butyraldehyde dehydrogenase; and
    f) at least one gene encoding a 1-butanol dehydrogenase.

13. The process of claim 7, wherein the yeast host cell comprises a 2-butanol biosynthetic pathway comprising:
    a) at least one gene encoding an acetolactate synthase;
    b) at least one gene encoding an acetolactate decarboxylase;
    c) at least one gene encoding a butanediol dehydrogenase;
    d) at least one gene encoding a butanediol dehydratase; and
    e) at least one gene encoding a 2-butanol dehydrogenase.

* * * * *

SEQUENCE LISTING

<160> NUMBER OF SEQ ID NOS: 148

<210> SEQ ID NO 1
<211> LENGTH: 1179
<212> TYPE: DNA
<213> ORGANISM: Clostridium acetobutylicum

<400> SEQUENCE: 1

```
atgaaagaag ttgtaatagc tagtgcagta agaacagcga ttggatctta tggaaagtct      60
cttaaggatg taccagcagt agatttagga gctacagcta taaggaagc agttaaaaaa     120 gcaggaataa aaccagagga tgttaatgaa gtcattttag gaaatgttct tcaagcaggt    180
```

| | |
|---|---|
| ttaggacaga atccagcaag acaggcatct tttaaagcag gattaccagt tgaaattcca | 240 |
| gctatgacta ttaataaggt ttgtggttca ggacttagaa cagttagctt agcagcacaa | 300 |
| attataaaag caggagatgc tgacgtaata atagcaggtg gtatggaaaa tatgtctaga | 360 |
| gctccttact tagcgaataa cgctagatgg ggatatagaa tgggaaacgc taaatttgtt | 420 |
| gatgaaatga tcactgacgg attgtgggat gcatttaatg attaccacat gggaataaca | 480 |
| gcagaaaaca tagctgagag atggaacatt tcaagagaag aacaagatga gtttgctctt | 540 |
| gcatcacaaa aaaagctga agaagctata aaatcaggtc aatttaaaga tgaaatagtt | 600 |
| cctgtagtaa ttaaaggcag aaaggggaaa actgtagttg atacagatga gcacccctaga | 660 |
| tttggatcaa ctatagaagg acttgcaaaa ttaaaacctg ccttcaaaaa agatggaaca | 720 |
| gttacagctg gtaatgcatc aggattaaat gactgtgcag cagtacttgt aatcatgagt | 780 |
| gcagaaaaag ctaaagagct tggagtaaaa ccacttgcta agatagtttc ttatggttca | 840 |
| gcaggagttg acccagcaat aatgggatat ggaccttttct atgcaacaaa agcagctatt | 900 |
| gaaaagcag gttggacagt tgatgaatta gatttaatag aatcaaatga agcttttgca | 960 |
| gctcaaagtt tagcagtagc aaaagattta aaatttgata tgaataaagt aaatgtaaat | 1020 |
| ggaggagcta ttgcccttgg tcatccaatt ggagcatcag gtgcaagaat actcgttact | 1080 |
| cttgtacacg caatgcaaaa aagagatgca aaaaaaggct tagcaacttt atgtataggt | 1140 |
| ggcggacaag gaacagcaat attgctagaa aagtgctag | 1179 |

<210> SEQ ID NO 2
<211> LENGTH: 392
<212> TYPE: PRT
<213> ORGANISM: Clostridium acetobutylicum

<400> SEQUENCE: 2

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys 195                 200                 205
Gly Glu Thr Val Val Asp Thr Asp Glu His Pro Arg Phe Gly Ser Thr
            210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 3
<211> LENGTH: 1179
<212> TYPE: DNA
<213> ORGANISM: Clostridium acetobutylicum

<400> SEQUENCE: 3
atgagagatg tagtaatagt aagtgctgta agaactgcaa taggagcata tggaaaaaca      60
ttaaaggatt tacctgcaac agagttagga gctatagtaa taaggaagc tgtaagaaga     120 gctaatataa atccaaatga gattaatgaa gttattttg gaaatgtact tcaagctgga     180
ttaggccaaa acccagcaag acaagcagca gtaaaagcag gattaccttt agaaacacct     240
gcgtttacaa tcaataaggt ttgtggttca ggtttaagat ctataagttt agcagctcaa     300
attataaaag ctggagatgc tgataccatt gtagtaggtg gtatggaaaa atatgtctaga    360 tcaccatatt tgattaacaa tcagagatgg ggtcaaagaa tgggagatag tgaattagtt    420
gatgaaatga taaaggatgg tttgtgggat gcatttaatg atatcatat gggagtaact     480 gcagaaaata ttgcagaaca atggaatata caagagaag agcaagatga attttcactt    540
atgtcacaac aaaaagctga aaaagccatt aaaaatggag aatttaagga tgaaatagtt    600
cctgtattaa taaagactaa aaaaggtgaa atagtctttg atcaagatga atttcctaga    660
ttcggaaaca ctattgaagc attaagaaaa cttaaaccta ttttcaagga aaatggtact    720
gttacagcag gtaatgcatc cggattaaat gatggagctg cagcactagt aataatgagc    780
gctgataaag ctaacgctct cggaataaaa ccacttgcta agattacttc ttacggatca    840
tatgggggta gatccatcaa tatgggatat ggagcttttt atgcaactaa agctgcctta    900
gataaaatta tttaaaaccc tgaagactta gatttaattg aagctaacga ggcatatgct    960
tctcaaagta tagcagtaac tagagattta aatttagata tgagtaaagt taatgttaat   1020

-continued

```
ggtggagcta tagcacttgg acatccaata ggtgcatctg gtgcacgtat tttagtaaca    1080
ttactatacg ctatgcaaaa aagagattca aaaaaggtc ttgctactct atgtattggt    1140
ggaggtcagg gaacagctct cgtagttgaa agagactaa                          1179
```

<210> SEQ ID NO 4
<211> LENGTH: 392
<212> TYPE: PRT
<213> ORGANISM: Clostridium acetobutylicum

<400> SEQUENCE: 4

| | | | | | | | | | | | | | | |
|---|---|---|---|---|---|---|---|---|---|---|---|---|---|---|
| Met | Arg | Asp | Val | Val | Ile | Val | Ser | Ala | Val | Arg | Thr | Ala | Ile | Gly | Ala |
| 1 | | | | 5 | | | | | 10 | | | | | 15 | |
| Tyr | Gly | Lys | Thr | Leu | Lys | Asp | Val | Pro | Ala | Thr | Glu | Leu | Gly | Ala | Ile |
| | | | 20 | | | | | 25 | | | | | 30 | | |
| Val | Ile | Lys | Glu | Ala | Val | Arg | Arg | Ala | Asn | Ile | Asn | Pro | Asn | Glu | Ile |
| | | 35 | | | | | 40 | | | | | 45 | | | |
| Asn | Glu | Val | Ile | Phe | Gly | Asn | Val | Leu | Gln | Ala | Gly | Leu | Gly | Gln | Asn |
| | 50 | | | | | 55 | | | | | 60 | | | | |
| Pro | Ala | Arg | Gln | Ala | Ala | Val | Lys | Ala | Gly | Leu | Pro | Leu | Glu | Thr | Pro |
| 65 | | | | | 70 | | | | | 75 | | | | | 80 |
| Ala | Phe | Thr | Ile | Asn | Lys | Val | Cys | Gly | Ser | Gly | Leu | Arg | Ser | Ile | Ser |
| | | | | 85 | | | | | 90 | | | | | 95 | |
| Leu | Ala | Ala | Gln | Ile | Ile | Lys | Ala | Gly | Asp | Ala | Asp | Thr | Ile | Val | Val |
| | | | 100 | | | | | 105 | | | | | 110 | | |
| Gly | Gly | Met | Glu | Asn | Met | Ser | Arg | Ser | Pro | Tyr | Leu | Ile | Asn | Asn | Gln |
| | | 115 | | | | | 120 | | | | | 125 | | | |
| Arg | Trp | Gly | Gln | Arg | Met | Gly | Asp | Ser | Glu | Leu | Val | Asp | Glu | Met | Ile |
| | 130 | | | | | 135 | | | | | 140 | | | | |
| Lys | Asp | Gly | Leu | Trp | Asp | Ala | Phe | Asn | Gly | Tyr | His | Met | Gly | Val | Thr |
| 145 | | | | | 150 | | | | | 155 | | | | | 160 |
| Ala | Glu | Asn | Ile | Ala | Glu | Gln | Trp | Asn | Ile | Thr | Arg | Glu | Glu | Gln | Asp |
| | | | | 165 | | | | | 170 | | | | | 175 | |
| Glu | Phe | Ser | Leu | Met | Ser | Gln | Gln | Lys | Ala | Glu | Lys | Ala | Ile | Lys | Asn |
| | | | 180 | | | | | 185 | | | | | 190 | | |
| Gly | Glu | Phe | Lys | Asp | Glu | Ile | Val | Pro | Val | Leu | Ile | Lys | Thr | Lys | Lys |
| | | 195 | | | | | 200 | | | | | 205 | | | |
| Gly | Glu | Ile | Val | Phe | Asp | Gln | Asp | Glu | Phe | Pro | Arg | Phe | Gly | Asn | Thr |
| | 210 | | | | | 215 | | | | | 220 | | | | |
| Ile | Glu | Ala | Leu | Arg | Lys | Leu | Lys | Pro | Ile | Phe | Lys | Glu | Asn | Gly | Thr |
| 225 | | | | | 230 | | | | | 235 | | | | | 240 |
| Val | Thr | Ala | Gly | Asn | Ala | Ser | Gly | Leu | Asn | Asp | Gly | Ala | Ala | Ala | Leu |
| | | | | 245 | | | | | 250 | | | | | 255 | |
| Val | Ile | Met | Ser | Ala | Asp | Lys | Ala | Asn | Ala | Leu | Gly | Ile | Lys | Pro | Leu |
| | | | 260 | | | | | 265 | | | | | 270 | | |
| Ala | Lys | Ile | Thr | Ser | Tyr | Gly | Ser | Tyr | Gly | Val | Asp | Pro | Ser | Ile | Met |
| | | 275 | | | | | 280 | | | | | 285 | | | |
| Gly | Tyr | Gly | Ala | Phe | Tyr | Ala | Thr | Lys | Ala | Ala | Leu | Asp | Lys | Ile | Asn |
| | 290 | | | | | 295 | | | | | 300 | | | | |
| Leu | Lys | Pro | Glu | Asp | Leu | Asp | Leu | Ile | Glu | Ala | Asn | Glu | Ala | Tyr | Ala |
| 305 | | | | | 310 | | | | | 315 | | | | | 320 |
| Ser | Gln | Ser | Ile | Ala | Val | Thr | Arg | Asp | Leu | Asn | Leu | Asp | Met | Ser | Lys |
| | | | | 325 | | | | | 330 | | | | | 335 | |
| Val | Asn | Val | Asn | Gly | Gly | Ala | Ile | Ala | Leu | Gly | His | Pro | Ile | Gly | Ala |

Ser Gly Ala Arg Ile Leu Val Thr Leu Leu Tyr Ala Met Gln Lys Arg
          355                 360                 365

Asp Ser Lys Lys Gly Leu Ala Thr Leu Cys Ile Gly Gly Gln Gly
        370                 375                 380

Thr Ala Leu Val Val Glu Arg Asp
385                 390

<210> SEQ ID NO 5
<211> LENGTH: 849
<212> TYPE: DNA
<213> ORGANISM: Clostridium acetobutylicum

<400> SEQUENCE: 5

```
atgaaaaagg tatgtgttat aggtgcaggt actatgggtt caggaattgc tcaggcattt    60
gcagctaaag gatttgaagt agtattaaga gatattaaag atgaatttgt tgatagagga   120
ttagatttta tcaataaaaa tctttctaaa ttagttaaaa aaggaaagat agaagaagct   180
actaaagttg aaatcttaac tagaattttcc ggaacagttg accttaatat ggcagctgat   240
tgcgatttag ttatagaagc agctgttgaa agaatggata ttaaaaagca gattttttgct   300
gacttagaca atatatgcaa gccagaaaca attcttgcat caaatacatc atcactttca   360
ataacagaag tggcatcagc aactaaaaga cctgataagg ttataggtat gcatttcttt   420
aatccagctc ctgttatgaa gcttgtagag gtaataagag aatagctac atcacaagaa   480
actttgatg cagttaaaga gacatctata gcaataggaa aagatcctgt agaagtagca   540
gaagcaccag gatttgttgt aaatagaata ttaataccaa tgattaatga agcagttggt   600
atattagcag aaggaatagc ttcagtagaa gacatagata agctatgaa acttggagct   660
aatcacccaa tgggaccatt agaattaggt gattttatag gtcttgatat atgtcttgct   720
ataatggatg tttttatactc agaaactgga gattctaagt atagaccaca tacattactt   780
aagaagtatg taagagcagg atggcttgga agaaaatcag gaaaaggttt ctacgattat   840
tcaaaataa                                                           849
```

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr

```
            115                 120                 125
Lys Arg Pro Asp Lys Val Ile Gly Met His Phe Phe Asn Pro Ala Pro
        130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280

<210> SEQ ID NO 7
<211> LENGTH: 786
<212> TYPE: DNA
<213> ORGANISM: Clostridium acetobutylicum

<400> SEQUENCE: 7
atggaactaa acaatgtcat ccttgaaaag gaaggtaaag ttgctgtagt taccattaac      60
agacctaaag cattaaatgc gttaaatagt gatacactaa agaaatggga ttatgttata     120
ggtgaaattg aaaatgatag cgaagtactt gcagtaattt taactggagc aggagaaaaa     180
tcatttgtag caggagcaga tatttctgag atgaaggaaa tgaataccat tgaaggtaga     240
aaattcggga tacttggaaa taagtgtttt agaagattag aacttcttga aaagcctgta     300
atagcagctg ttaatggttt tgcttttagga ggcggatgcg aaatagctat gtcttgtgat     360
ataagaatag cttcaagcaa cgcaagattt ggtcaaccag aagtaggtct cggaataaca     420
cctggttttg gtggtacaca aagactttca agattagttg aatgggcat ggcaaagcag     480 cttatattta ctgcacaaaa tataaaggca gatgaagcat taagaatcgg acttgtaaat     540
aaggtagtag aacctagtga attaatgaat acagcaaaag aaattgcaaa caaaattgtg     600
agcaatgctc cagtagctgt taagttaagc aaacaggcta ttaatagagg aatgcagtgt     660
gatattgata ctgctttagc atttgaatca gaagcatttg gagaatgctt ttcaacagag     720
gatcaaaagg atgcaatgac agctttcata gagaaaagaa aaattgaagg cttcaaaaat     780
agatag                                                                 786

<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15
```

```
Val Thr Ile Asn Arg Pro Lys Ala Leu Asn Ala Leu Asn Ser Asp Thr
             20                  25                  30

Leu Lys Glu Met Asp Tyr Val Ile Gly Glu Ile Glu Asn Asp Ser Glu
         35                  40                  45

Val Leu Ala Val Ile Leu Thr Gly Ala Gly Glu Lys Ser Phe Val Ala
     50                  55                  60

Gly Ala Asp Ile Ser Glu Met Lys Glu Met Asn Thr Ile Glu Gly Arg
 65                  70                  75                  80

Lys Phe Gly Ile Leu Gly Asn Lys Val Phe Arg Leu Glu Leu Leu
                 85                  90                  95

Glu Lys Pro Val Ile Ala Ala Val Asn Gly Phe Ala Leu Gly Gly Gly
             100                 105                 110

Cys Glu Ile Ala Met Ser Cys Asp Ile Arg Ile Ala Ser Ser Asn Ala
         115                 120                 125

Arg Phe Gly Gln Pro Glu Val Gly Leu Gly Ile Thr Pro Gly Phe Gly
     130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
             165                 170                 175

Gly Leu Val Asn Lys Val Val Glu Pro Ser Glu Leu Met Asn Thr Ala
         180                 185                 190

Lys Glu Ile Ala Asn Lys Ile Val Ser Asn Ala Pro Val Ala Val Lys
     195                 200                 205

Leu Ser Lys Gln Ala Ile Asn Arg Gly Met Gln Cys Asp Ile Asp Thr
 210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
             245                 250                 255

Gly Phe Lys Asn Arg
             260

<210> SEQ ID NO 9
<211> LENGTH: 1197
<212> TYPE: DNA
<213> ORGANISM: Clostridium acetobutylicum

<400> SEQUENCE: 9
atgatagtaa aagcaaagtt tgtaaaagga tttatcagag atgtacatcc ttatggttgc      60
agaagggaag tactaaatca aatagattat tgtaagaagg ctattgggtt tagggaccca     120
aagaaggttt taattgttgg agcctcatct gggtttggtc ttgctactag aatttcagtt     180
gcatttggag gtccagaagc tcacacaatt ggagtatcct atgaaacagg agctacagat     240
agaagaatag aacagcggga tggtataat aacatatttt ttaaagaatt tgctaaaaaa     300
aaaggattag ttgcaaaaaa cttcattgag gatgcctttt ctaatgaaac caaagataaa     360
gttattaagt atataaagga tgaatttggt aaaatagatt tatttgttta gtttagct     420 gcgcctagga gaaaggacta taaaactgga atgttata cttcaagaat aaaaacaatt     480
ttaggagatt ttgagggacc gactattgat gttgaaagag acgagattac tttaaaaaag     540
gttagtagtg ctagcattga gaaattgaa gaaactagaa aggtaatggg tggagaggat     600
tggcaagagt ggtgtgaaga gctgcttat gaagattgtt tttcggataa agcaactacc     660
atagcatact cgtatatagg atccccaaga acctacaaga tatatagaga aggtactata     720
```

```
ggaatagcta aaaaggatct tgaagataag gctaagctta taaatgaaaa acttaacaga    780
gttataggtg gtagagcctt tgtgtctgtg aataaagcat tagttacaaa agcaagtgca    840
tatattccaa cttttcctct ttatgcagct attttatata aggtcatgaa agaaaaaaat    900
attcatgaaa attgtattat gcaaattgag agaatgtttt ctgaaaaaat atattcaaat    960
gaaaaaatac aatttgatga caagggaaga ttaaggatgg acgatttaga gcttagaaaa   1020
gacgttcaag acgaagttga tagaatatgg agtaatatta ctcctgaaaa ttttaaggaa   1080
ttatctgatt ataagggata caaaaaagaa ttcatgaact taaacggttt tgatctagat   1140
ggggttgatt atagtaaaga cctggatata gaattattaa gaaaattaga accttaa     1197
```

<210> SEQ ID NO 10
<211> LENGTH: 398
<212> TYPE: PRT
<213> ORGANISM: Clostridium acetobutylicum

<400> SEQUENCE: 10

```
Met Ile Val Lys Ala Lys Phe Val Lys Gly Phe Ile Arg Asp Val His
  1               5                  10                  15

Pro Tyr Gly Cys Arg Arg Glu Val Leu Asn Gln Ile Asp Tyr Cys Lys
             20                  25                  30

Lys Ala Ile Gly Phe Arg Gly Pro Lys Lys Val Leu Ile Val Gly Ala
         35                  40                  45

Ser Ser Gly Phe Gly Leu Ala Thr Arg Ile Ser Val Ala Phe Gly Gly
     50                  55                  60

Pro Glu Ala His Thr Ile Gly Val Ser Tyr Glu Thr Gly Ala Thr Asp
 65                  70                  75                  80

Arg Arg Ile Gly Thr Ala Gly Trp Tyr Asn Asn Ile Phe Phe Lys Glu
                 85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285
```

```
Ala Ala Ile Leu Tyr Lys Val Met Lys Glu Lys Asn Ile His Glu Asn
    290                 295                 300

Cys Ile Met Gln Ile Glu Arg Met Phe Ser Lys Ile Tyr Ser Asn
305                 310                 315                 320

Glu Lys Ile Gln Phe Asp Asp Lys Gly Arg Leu Arg Met Asp Leu
                325                 330                 335

Glu Leu Arg Lys Asp Val Gln Asp Glu Val Asp Arg Ile Trp Ser Asn
            340                 345                 350

Ile Thr Pro Glu Asn Phe Lys Glu Leu Ser Asp Tyr Lys Gly Tyr Lys
                355                 360                 365

Lys Glu Phe Met Asn Leu Asn Gly Phe Asp Leu Asp Gly Val Asp Tyr
    370                 375                 380

Ser Lys Asp Leu Asp Ile Glu Leu Leu Arg Lys Leu Glu Pro
385                 390                 395

<210> SEQ ID NO 11
<211> LENGTH: 1407
<212> TYPE: DNA
<213> ORGANISM: Clostridium beijerinckii

<400> SEQUENCE: 11
atgaataaag acacactaat acctacaact aaagatttaa agtaaaaac aaatggtgaa        60 aacattaatt taagaactaa caaggataat tcttcatgtt tcggagtatt cgaaaatgtt      120
gaaaatgcta taagcagcgc tgtacacgca caaagatat ataccccttca ttatacaaaa     180 gagcaaagag aaaaaatcat aactgagata agaaaggccg cattacaaaa taagagggtc     240
ttggctacaa tgattctaga agaaacacat atgggaagat atgaggataa aatattaaaa     300
catgaattgg tagctaaata tactcctggt acagaagatt taactactac tgcttggtca     360
ggtgataatg gtcttacagt tgtagaaatg tctccatatg gtgttatagg tgcaataact     420
ccttctacga atccaactga aactgtaata tgtaatagca taggcatgat agctgctgga     480
aatgctgtag tatttaacgg acacccatgc gctaaaaaat gtgttgcctt tgctgttgaa     540 atgataaaata aggcaattat ttcatgtggc ggtcctgaaa atctagtaac aactataaaa     600
aatccaacta tggagtctct agatgcaatt attaagcatc cttcaataaa acttcttgc      660 ggaactgggg gtccaggaat ggtaaaaacc ctcttaaatt ctggtaagaa agctataggt     720
gctggtgctg gaaatccacc agttattgta gatgatactg ctgatataga aaaggctggt     780
aggagcatca ttgaaggctg ttcttttgat aataaattac cttgtattgc agaaaaagaa     840
gtatttgttt ttgagaatgt tgcagatgat ttaatatcta acatgctaaa aaataatgct     900
gtaattataa atgaagatca agtatcaaaa ttaatagatt tagtattaca aaaaataat    960 gaaactcaag atactttat aaacaaaaaa tgggtaggaa agatgcaaa attattctta      1020 gatgaaatag atgttgagtc tccttcaaat gttaaatgca taatctgcga gtaaatgca     1080 atcatccat ttgttatgac agaactcatg atgccaatat tgccaattgt aagagttaaa    1140
gatatagatg aagctattaa atatgcaaag atagcagaac aaaatagaaa acatagtgcc    1200
tatatttatt ctaaaaatat agacaaccta aatagatttg aaagagaaat agatactact    1260
atttttgtaa agaatgctaa atcttttgct ggtgttggtt atgaagcaga aggatttaca    1320
actttcacta ttgctggatc tactggtgag ggaataaccct ctgcaaggaa ttttacaaga    1380
caaagaagat gtgtacttgc cggctaa                                         1407

<210> SEQ ID NO 12
```

```
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
```

```
                385                 390                 395                 400
Tyr Ile Tyr Ser Lys Asn Ile Asp Asn Leu Asn Arg Phe Glu Arg Glu
                    405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaatttttt tcggtaaaga taagataaat      60
gtacttggaa gagagcttaa aaaatatggt tctaaagtgc ttatagttta tggtggagga     120
agtataaaga gaaatggaat atatgataaa gctgtaagta tacttgaaaa aacagtatt     180 aaattttatg aacttgcagg agtagagcca aatccaagag taactacagt tgaaaaagga     240
gttaaaatat gtagagaaaa tggagttgaa gtagtactag ctataggtgg aggaagtgca     300
atagattgcg caaggttat agcagcagca tgtgaatatg atggaaatcc atgggatatt     360
gtgttagatg gctcaaaaat aaaaagggtg cttcctatag ctagtatatt aaccattgct     420
gcaacaggat cagaaatgga tacgtgggca gtaataaata tatggatac aaacgaaaaa     480 ctaattgcgg cacatccaga tatggctcct aagttttcta tattagatcc aacgtatacg     540
tataccgtac ctaccaatca aacagcagca ggaacagctg atattatgag tcatatattt     600
gaggtgtatt ttagtaatac aaaaacagca tatttgcagg atagaatggc agaagcgtta     660
ttaagaactt gtattaaata tggaggaata gctcttgaga agccggatga ttatgaggca     720
agagccaatc taatgtgggc ttcaagtctt gcgataaatg acttttaac atatggtaaa     780 gacactaatt ggagtgtaca cttaatggaa catgaattaa gtgcttatta cgacataaca     840
cacggcgtag gcttgcaat tttaacacct aattggatgg agtatatttt aaataatgat     900
acagtgtaca gtttgttga atatggtgta aatgtttggg aatagacaa agaaaaaaat     960 cactatgaca tagcacatca agcaatacaa aaaacaagag attactttgt aaatgtacta    1020
ggtttaccat ctagactgag agatgttgga attgaagaag aaaaattgga cataatggca    1080
aaggaatcag taaagcttac aggaggaacc ataggaaacc taagaccagt aaacgcctcc    1140
gaagtcctac aaatattcaa aaaatctgtg taaaacgcct ccgaagtcct acaaatattc    1200
aaaaaatctg tgtaa                                                     1215

<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
```

```
            20                  25                  30
Val Leu Ile Val Tyr Gly Gly Ser Ile Lys Arg Asn Gly Ile Tyr
         35                  40                  45

Asp Lys Ala Val Ser Ile Leu Glu Lys Asn Ser Ile Lys Phe Tyr Glu
 50                  55                  60

Leu Ala Gly Val Glu Pro Asn Pro Arg Val Thr Val Glu Lys Gly
 65                  70                  75                  80

Val Lys Ile Cys Arg Glu Asn Gly Val Glu Val Leu Ala Ile Gly
                     85                  90                  95

Gly Gly Ser Ala Ile Asp Cys Ala Lys Val Ile Ala Ala Cys Glu
                100                 105                 110

Tyr Asp Gly Asn Pro Trp Asp Ile Val Leu Asp Gly Ser Lys Ile Lys
                115                 120                 125

Arg Val Leu Pro Ile Ala Ser Ile Leu Thr Ile Ala Thr Gly Ser
130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
                180                 185                 190

Ala Asp Ile Met Ser His Ile Phe Glu Val Tyr Phe Ser Asn Thr Lys
                195                 200                 205

Thr Ala Tyr Leu Gln Asp Arg Met Ala Glu Ala Leu Leu Arg Thr Cys
                210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
                260                 265                 270

Leu Ser Ala Tyr Tyr Asp Ile Thr His Gly Val Gly Leu Ala Ile Leu
                275                 280                 285

Thr Pro Asn Trp Met Glu Tyr Ile Leu Asn Asn Asp Thr Val Tyr Lys
                290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
                340                 345                 350

Glu Glu Lys Leu Asp Ile Met Ala Lys Glu Ser Val Lys Leu Thr Gly
                355                 360                 365

Gly Thr Ile Gly Asn Leu Arg Pro Val Asn Ala Ser Glu Val Leu Gln
                370                 375                 380

Ile Phe Lys Lys Ser Val
385                 390

<210> SEQ ID NO 15
<211> LENGTH: 1170
<212> TYPE: DNA
<213> ORGANISM: Clostridium acetobutylicum

<400> SEQUENCE: 15
```

```
atgctaagtt ttgattattc aataccaact aaagttttt ttggaaaagg aaaaatagac    60
gtaattggag aagaaattaa gaaatatggc tcaagagtgc ttatagttta tggcggagga   120
agtataaaaa ggaacggtat atatgataga gcaacagcta tattaaaaga aaacaatata   180
gctttctatg aactttcagg agtagagcca atcctaggaa taacaacagt aaaaaaaggc   240
atagaaatat gtagagaaaa taatgtggat ttagtattag caatagggggg aggaagtgca   300
atagactgtt ctaaggtaat tgcagctgga gtttattatg atggcgatac atgggacatg   360
gttaaagatc catctaaaat aactaaagtt cttccaattg caagtatact tactctttca   420
gcaacagggt ctgaaatgga tcaaattgca gtaatttcaa atatggagac taatgaaaag   480
cttggagtag gacatgatga tatgagacct aaattttcag tgttagatcc tacatatact   540
tttacagtac ctaaaaatca aacagcagcg ggaacagctg acattatgag tcacaccttt   600
gaatcttact ttagtggtgt tgaaggtgct tatgtgcagg acggtatagc agaagcaatc   660
ttaagaacat gtaaagta tggaaaaata gcaatggaga agactgatga ttacgaggct   720
agagctaatt tgatgtgggc ttcaagttta gctataaatg gtctattatc acttggtaag   780
gatagaaaat ggagttgtca tcctatggaa cacgagttaa gtgcatatta tgatataaca   840
catggtgtag acttgcaat tttaacaccctt aattggatgg aatatattct aaatgacgat   900
acacttcata atttgtttc ttatggaata aatgtttggg aatagacaa gaacaaagat   960
aactatgaaa tagcacgaga ggctattaaa atacgagaa atactttaa ttcattgggt  1020
attcctcaa agcttagaga agttggaata ggaaaagata aactagaact aatggcaaag  1080
caagctgtta gaaattctgg aggaacaata ggaagtttaa gaccaataaa tgcagaggat  1140
gttcttgaga tatttaaaaa atcttattaa                                   1170
```

<210> SEQ ID NO 16
<211> LENGTH: 389
<212> TYPE: PRT
<213> ORGANISM: Clostridium acetobutylicum

<400> SEQUENCE: 16

```
Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Val Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
```

```
                    165                 170                 175
Pro Thr Tyr Thr Phe Thr Val Pro Lys Asn Gln Thr Ala Ala Gly Thr
                180                 185                 190

Ala Asp Ile Met Ser His Thr Phe Glu Ser Tyr Phe Ser Gly Val Glu
            195                 200                 205

Gly Ala Tyr Val Gln Asp Gly Ile Ala Glu Ala Ile Leu Arg Thr Cys
        210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
                260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asp Asp Thr Leu His Lys
        290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
                340                 345                 350

Asp Lys Leu Glu Leu Met Ala Lys Gln Ala Val Arg Asn Ser Gly Gly
            355                 360                 365

Thr Ile Gly Ser Leu Arg Pro Ile Asn Ala Glu Asp Val Leu Glu Ile
        370                 375                 380

Phe Lys Lys Ser Tyr
385

<210> SEQ ID NO 17
<211> LENGTH: 780
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcg gacctgctga acacggcga tttcggcctc     180 ggcaccttta atgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480
atgaccgacg tcctcgacga tcagccggtg ttccgcttta accagcgcga aggggtgctg     540
gtcggcttcc ggaccccgca gcatatgcag gggatcaacg tcgccgggta tcacgagcac     600
tttattaccg atgaccgcaa aggcggcggt cacctgctgg attaccagct cgaccatggg     660
gtgctgacct cggcgaaat tcacaagctg atgatcgacc tgcccgccga cagcgcgttc     720
ctgcaggcta atctgcatcc cgataatctc gatgccgcca tccgttccgt agaaagttaa     780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60

Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag    60
ctggaagctc agggagtacg ccaggtgttc ggcatccccg gcgccaaaat tgacaaggtc   120
ttcgactcac tgctggattc ctcgattcgc attattccgg tacgccacga agccaacgcc   180
gcgtttatgg ccgccgccgt cggacgcatt accggcaaag cgggcgtggc gctggtcacc   240
tccggtccgg gctgttccaa cctgatcacc ggcatggcca ccgcgaacag cgaaggcgac   300
ccggtggtgg ccctgggcgg cgcggtaaaa cgcgccgata agcgaagcca ggtccaccag   360
agtatggata cggtggcgat gttcagcccg gtcaccaaat acgccgtcga ggtgacggcg   420
```

```
ccggatgcgc tggcggaagt ggtctccaac gccttccgcg ccgccgagca gggccggccg    480
ggcagcgcgt tcgttagcct gccgcaggat gtggtcgatg cccggtcag cggcaaagtg      540
ctgccggcca gcggggcccc gcagatgggc gccgcgccgg atgatgccat cgaccaggtg    600
gcgaagctta tcgcccaggc gaagaacccg atcttcctgc tcggcctgat ggccagccag    660
ccggaaaaca gcaaggcgct cgccgtttg ctggagacca gccatattcc agtcaccagc    720
acctatcagg ccgccggagc ggtgaatcag gataacttct ctcgcttcgc cggccgggtt    780
gggctgttta caaccaggc cggggaccgt ctgctgcagc tcgccgacct ggtgatctgc    840
atcggctaca gcccggtgga atacgaaccg gcgatgtgga acagcggcaa cgcgacgctg    900
gtgcacatcg acgtgctgcc cgcctatgaa gagcgcaact acaccccgga tgtcgagctg    960
gtgggcgata tcgccggcac tctcaacaag ctggcgcaaa atatcgatca tcggctggtg   1020
ctctccccgc aggcggcgga gatcctccgc gaccgccagc accagcgcga gctgctggac   1080
cgccgcggcg cgcagctgaa ccagtttgcc ctgcatccgc tgcgcatcgt tcgcgccatg   1140
caggacatcg tcaacagcga cgtcacgttg accgtgaca tgggcagctt ccatatctgg    1200
attgcccgct acctgtacag cttccgcgcc cgtcaggtga tgatctccaa cggccagcag   1260
accatgggcg tcgccctgcc ctgggctatc ggcgcctggc tggtcaatcc tgagcgaaaa   1320
gtggtctccg tctccggcga cggcggcttc ctgcagtcga gcatggagct ggagaccgcc   1380
gtccgcctga agccaacgt actgcacctg atctgggtcg ataacggcta caacatggtg    1440
gccattcagg aagagaaaaa ataccagcgc ctgtccggcg tcgagttcgg gccgatggat   1500
tttaaagcct atgccgaatc cttcggcgcg aaagggtttg ccgtggaaag cgccgaggcg   1560
ctggagccga ccctgcacgc ggcgatggac gtcgacggcc cggcggtggt ggccattccg   1620
gtggattatc gcgataaccc gctgctgatg ggccagctgc atctgagtca gattctgtaa   1680

<210> SEQ ID NO 20
<211> LENGTH: 559
<212> TYPE: PRT
<213> ORGANISM: Klebsiella pneumoniae

<400> SEQUENCE: 20

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
                20                  25                  30

Pro Gly Ala Lys Ile Asp Lys Val Phe Asp Ser Leu Leu Asp Ser Ser
            35                  40                  45

Ile Arg Ile Ile Pro Val Arg His Glu Ala Asn Ala Ala Phe Met Ala
        50                  55                  60

Ala Ala Val Gly Arg Ile Thr Gly Lys Ala Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160
```

```
Gly Ser Ala Phe Val Ser Leu Pro Gln Asp Val Val Gly Pro Val
            165                 170                 175

Ser Gly Lys Val Leu Pro Ala Ser Gly Ala Pro Gln Met Gly Ala Ala
        180                 185                 190

Pro Asp Asp Ala Ile Asp Gln Val Ala Lys Leu Ile Ala Gln Ala Lys
            195                 200                 205

Asn Pro Ile Phe Leu Leu Gly Leu Met Ala Ser Gln Pro Glu Asn Ser
210                 215                 220

Lys Ala Leu Arg Arg Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
            260                 265                 270

Gln Leu Ala Asp Leu Val Ile Cys Ile Gly Tyr Ser Pro Val Glu Tyr
        275                 280                 285

Glu Pro Ala Met Trp Asn Ser Gly Asn Ala Thr Leu Val His Ile Asp
290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
530                 535                 540

Asp Asn Pro Leu Leu Met Gly Gln Leu His Leu Ser Gln Ile Leu
545                 550                 555

<210> SEQ ID NO 21
<211> LENGTH: 771
```

```
<212> TYPE: DNA
<213> ORGANISM: Klebsiella pneumoniae

<400> SEQUENCE: 21
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
gccggccacg tcggcaaccc ggagctggcg gtgtatagct ccagtaaatt cgcggtacgc     480
ggcttaaccc agaccgccgc tcgcgacctc gcgccgctgg gcatcacggt caacggctac     540
tgcccgggga ttgtcaaaac gccaatgtgg gccgaaattg accgccaggt gtccgaagcc     600
gccggtaaac cgctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg gtcagtcgtt gctgatcgac ggcgggatgg tatttaacta a              771

<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
```

|        |     |     |     |     | 210 |     |     |     |     | 215 |     |     |     |     | 220 |     |     |     |
|--------|-----|-----|-----|-----|-----|-----|-----|-----|-----|-----|-----|-----|-----|-----|-----|-----|-----|-----|
| Glu    | Asp | Val | Ala | Ala | Cys | Val | Ser | Tyr | Leu | Ala | Ser | Pro | Asp | Ser | Asp |
| 225    |     |     |     |     | 230 |     |     |     |     | 235 |     |     |     |     | 240 |

Tyr Met Thr Gly Gln Ser Leu Leu Ile Asp Gly Gly Met Val Phe Asn
                245                 250                 255

<210> SEQ ID NO 23
<211> LENGTH: 1665
<212> TYPE: DNA
<213> ORGANISM: Klebsiella oxytoca

<400> SEQUENCE: 23

```
atgagatcga aaagatttga agcactggcg aaacgccctg tgaatcagga cggcttcgtt      60
aaggagtgga tcgaagaagg ctttatcgcg atggaaagcc cgaacgaccc aaaaccgtcg     120
attaaaatcg ttaacggcgc ggtgaccgag ctggacggga accggtaagc gattttgac      180
ctgatcgacc actttatcgc ccgctacggt atcaacctga accgcgccga agaagtgatg     240
gcgatggatt cggtcaagct ggccaacatg ctgtgcgatc gaacgttaa acgcagcgaa      300
atcgtcccgc tgaccaccgc gatgacgccg gcgaaaattg tcgaagtggt ttcgcatatg     360
aacgtcgtcg agatgatgat ggcgatgcag aaaatgcgcg cccgccgcac cccgtcccag     420
caggcgcacg tcaccaacgt caaagataac ccggtacaga ttgccgccga cgccgccgaa     480
ggggcatggc gcggatttga cgaacaggaa accaccgttg cggtagcgcg ctatgcgccg     540
ttcaacgcca tcgcgctgct ggtgggctcg caggtaggcc gtccgggcgt gctgacgcag     600
tgctcgctgg aagaagccac cgagctgaag ctcggcatgc tgggccacac ctgctacgcc     660
gaaaccatct ccgtctacgg caccgagccg gtctttaccg acggcgacga cacgccgtgg     720
tcgaagggct tcctcgcctc gtcctacgcc tctcgcgggc tgaaaatgcg ctttacctcc     780
ggctccggct cggaagtgca gatgggctac gccgaaggca atccatgct ttatctggaa      840
gcgcgctgca tctacatcac caaagccgcg ggcgtacagg tctgcaaaa cggttccgta      900
agctgcatcg gcgtgccgtc tgcggtgcct tccggcattc gcgcggtgct ggcggaaaac     960
ctgatctgtt cgtcgctgga tctggagtgc cctccagca acgaccagac cttcaccccac   1020
tccgatatgc gtcgtaccgc gcgcctgctg atgcagttcc tgccgggcac cgactttatc    1080
tcctccggtt attccgcggt gccgaactac gacaacatgt cgccggctc caacgaagat     1140
gccgaagact ttgacgacta caacgtcatc cagcgcgacc tgaaggtgga cggcggtttg    1200
cgtccggttc gcgaagagga cgtcatcgcc atccgtaaca aagccgcccg cgcgctgcag    1260
gccgtgtttg ccggaatggg gctgccgccg attaccgatg aagaagttga agccgcgacc    1320
tacgcccacg gttcgaaaga tatgccggag cgcaacatcg tcgaagacat caagttcgcc    1380
caggaaatca tcaataaaaa ccgcaacggt ctggaagtgg tgaaagcgct ggcgcagggc    1440
ggattcaccg acgtggccca ggacatgctc aacatccaga aagctaagct gaccggggac    1500
tacctgcata cctccgcgat tatcgtcggc gacgggcagg tgctgtcagc cgtcaacgac    1560
gtcaacgact atgccggtcc ggcaacgggc tatcgcctgc agggcgaacg ctgggaagag    1620
attaaaaaca tccctggcgc tcttgatccc aacgagattg attaa                     1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
                20                  25                  30

Ser Pro Asn Asp Pro Lys Pro Ser Ile Lys Ile Val Asn Gly Ala Val
            35                  40                  45

Thr Glu Leu Asp Gly Lys Pro Val Ser Asp Phe Asp Leu Ile Asp His
        50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415
```

```
Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Ile Lys Asn Ile
    530                 535                 540

Pro Gly Ala Leu Asp Pro Asn Glu Ile Asp
545                 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag      60
ggcagcgata aaccggtctc gtttaatgcg ccggcggcct ccgcggcgcc ccaggccacg     120
ccgcccgccg gcgacggctt cctgacggaa gtgggcgaag cgcgtcaggg aacccagcag     180
gacgaagtga ttatcgccgt cggcccggct tcggcctggc gcagaccgt caatatcgtc      240 ggcatcccgc ataagagcat tttgcgcgaa gtcattgccg gtattgaaga agaaggcatt     300
aaggcgcgcg tgattcgctg ctttaaatcc tccgacgtgg ccttcgtcgc cgttgaaggt     360
aatcgcctga gcggctccgg catctctatc ggcatccagt cgaaaggcac cacggtgatc     420
caccagcagg ggctgccgcc gctctctaac ctggagctgt tcccgcaggc gccgctgctg     480
accctggaaa cctatcgcca gatcggcaaa aacgccgccc gctatgcgaa acgcgaatcg     540
ccgcagccgg tcccgacgct gaatgaccag atggcgcggc cgaagtacca ggcgaaatcg     600
gccattttgc acattaaaga gaccaagtac gtggtgacgg gcaaaaaccc gcaggaactg     660
cgcgtggcgc tttga                                                      675

<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1               5                   10                  15

Ser Glu Met Lys Gly Ser Asp Lys Pro Val Ser Phe Asn Ala Pro Ala
            20                  25                  30

Ala Ser Ala Ala Pro Gln Ala Thr Pro Pro Ala Gly Asp Gly Phe Leu
        35                  40                  45

Thr Glu Val Gly Glu Ala Arg Gln Gly Thr Gln Gln Asp Glu Val Ile
    50                  55                  60
```

```
Ile Ala Val Gly Pro Ala Phe Gly Leu Ala Gln Thr Val Asn Ile Val
 65                  70                  75                  80

Gly Ile Pro His Lys Ser Ile Leu Arg Glu Val Ile Ala Gly Ile Glu
                 85                  90                  95

Glu Glu Gly Ile Lys Ala Arg Val Ile Arg Cys Phe Lys Ser Ser Asp
            100                 105                 110

Val Ala Phe Val Ala Val Glu Gly Asn Arg Leu Ser Gly Ser Gly Ile
            115                 120                 125

Ser Ile Gly Ile Gln Ser Lys Gly Thr Thr Val Ile His Gln Gln Gly
130                 135                 140

Leu Pro Pro Leu Ser Asn Leu Glu Leu Phe Pro Gln Ala Pro Leu Leu
145                 150                 155                 160

Thr Leu Glu Thr Tyr Arg Gln Ile Gly Lys Asn Ala Ala Arg Tyr Ala
                165                 170                 175

Lys Arg Glu Ser Pro Gln Pro Val Pro Thr Leu Asn Asp Gln Met Ala
            180                 185                 190

Arg Pro Lys Tyr Gln Ala Lys Ser Ala Ile Leu His Ile Lys Glu Thr
            195                 200                 205

Lys Tyr Val Val Thr Gly Lys Asn Pro Gln Glu Leu Arg Val Ala Leu
    210                 215                 220

<210> SEQ ID NO 27
<211> LENGTH: 522
<212> TYPE: DNA
<213> ORGANISM: Klebsiella oxytoca

<400> SEQUENCE: 27
atgaataccg acgcaattga atcgatggta cgcgacgtat tgagccgcat gaacagcctg      60
cagggcgagg cgcctgcggc ggctccggcg gctggcggcg cgtcccgtag cgccagggtc     120
agcgactacc cgctggcgaa caagcacccg gaatgggtga aaaccgccac aataaaacg      180 ctggacgact ttacgctgga aaacgtgctg agcaataaag tcaccgccca ggatatgcgt     240
attaccccgg aaaccctgcg cttacaggct tctattgcca agacgcgggg ccgcgaccgg     300
ctggcgatga acttcgagcg cgccgccgag ctgaccgcgg taccggacga tcgcattctt     360
gaaatctaca cgccctccg ccctatcgc tcgacgaaag aggagctgct ggcgatcgcc       420
gacgatctcg aaagccgcta tcaggcgaag atttgcgccg ctttcgttcg cgaagcggcc     480
acgctgtacg tcgagcgtaa aaaactcaaa ggcgacgatt aa                        522

<210> SEQ ID NO 28
<211> LENGTH: 173
<212> TYPE: PRT
<213> ORGANISM: Klebsiella oxytoca

<400> SEQUENCE: 28

Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
                20                  25                  30

Gly Ala Ser Arg Ser Ala Arg Val Ser Asp Tyr Pro Leu Ala Asn Lys
            35                  40                  45

His Pro Glu Trp Val Lys Thr Ala Thr Asn Lys Thr Leu Asp Asp Phe
        50                  55                  60

Thr Leu Glu Asn Val Leu Ser Asn Lys Val Thr Ala Gln Asp Met Arg
65                  70                  75                  80
```

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170

<210> SEQ ID NO 29
<211> LENGTH: 1041
<212> TYPE: DNA
<213> ORGANISM: Rhodococcus ruber

<400> SEQUENCE: 29
atgaaagccc tccagtacac cgagatcggc tccgagccgg tcgtcgtcga cgtccccacc      60
ccggcgcccg gccgggtga gatcctgctg aaggtcaccg cggccggctt gtgccactcg     120
gacatcttcg tgatggacat gccggcagag cagtacatct acggtcttcc cctcaccctc     180
ggccacgagg gcgtcggcac cgtcgccgaa ctcggcgccg cgtcaccgg attcgagacg      240 ggggacgccg tcgccgtgta cgggccgtgg gggtgcggtg cgtgccacgc gtgcgcgcgc     300
ggccgggaga actactgcac ccgcgccgcc gagctgggca tcaccccgcc cggtctcggc     360
tcgcccgggt cgatggccga gtacatgatc gtcgactcgg cgccacct cgtcccgatc      420 ggggacctcg accccgtcgc ggcggttccg ctcaccgacg cgggcctgac gccgtaccac     480
gcgatctcgc gggtcctgcc cctgctggga cccggctcga ccgcggtcgt catcggggtc     540
ggcggactcg gcacgtcgg catccagatc ctgcgcgccg tcagcgcggc ccgcgtgatc     600
gccgtcgatc tcgacgacga ccgactcgcg ctcgcccgcg aggtcggcgc cgacgcggcg     660
gtgaagtcgg cgccggggc ggcggacgcg atccgggagc tgaccggcgg tgagggcgcg     720
acggcggtgt cgacttcgt cggcgcccag tcgacgatcg acacggcgca gcaggtggtc     780
gcgatcgacg ggcacatctc ggtggtcggc atccatgccg cgcccacgc caaggtcggc     840 ttcttcatga tcccgttcgg cgcgtccgtc gtgacgccgt actggggcac gcggtccgag     900
ctgatggacg tcgtggacct ggccgtgccc ggccggctcg acatccacac cgagacgttc     960
accctcgacg agggacccac ggcctaccgg cggctacgcg agggcagcat ccgcggccgc    1020
ggggtggtcg tcccgggctg a                                              1041

<210> SEQ ID NO 30
<211> LENGTH: 346
<212> TYPE: PRT
<213> ORGANISM: Rhodococcus ruber

<400> SEQUENCE: 30

Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
 50                  55                  60

Val Gly Thr Val Ala Glu Leu Gly Ala Gly Val Thr Gly Phe Glu Thr
 65                  70                  75                  80

Gly Asp Ala Val Ala Val Tyr Gly Pro Trp Gly Cys Gly Ala Cys His
                 85                  90                  95

Ala Cys Ala Arg Gly Arg Glu Asn Tyr Cys Thr Arg Ala Ala Glu Leu
             100                 105                 110

Gly Ile Thr Pro Pro Gly Leu Gly Ser Pro Gly Ser Met Ala Glu Tyr
         115                 120                 125

Met Ile Val Asp Ser Ala Arg His Leu Val Pro Ile Gly Asp Leu Asp
130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Val Lys Ser Gly
210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345

<210> SEQ ID NO 31
<211> LENGTH: 1476
<212> TYPE: DNA
<213> ORGANISM: Escherichia coli

<400> SEQUENCE: 31
atggctaact acttcaatac actgaatctg cgccagcagc tggcacagct gggcaaatgt      60
cgctttatgg ccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420

-continued

```
gagcagatcc gtaaagatat caccgtagtg atggttgcgc cgaaatgccc aggcaccgaa      480
gtgcgtgaag agtacaaacg tgggttcggc gtaccgacgc tgattgccgt tcacccggaa      540
aacgatccga aaggcgaagg catggcgatt gccaaagcct gggcggctgc aaccggtggt      600
caccgtgcgg gtgtgctgga atcgtccttc gttgcggaag tgaaatctga cctgatgggc      660
gagcaaacca tcctgtgcgg tatgttgcag gctggctctc tgctgtgctt cgacaagctg      720
gtggaagaag gtaccgatcc agcatacgca gaaaaactga ttcagttcgg ttgggaaacc      780
atcaccgaag cactgaaaca gggcggcatc accctgatga tggaccgtct ctctaacccg      840
gcgaaactgc gtgcttatgc gctttctgaa cagctgaaag agatcatggc accccctgttc     900 cagaaacata tggacgacat catctccggc gaattctctt ccggtatgat ggcggactgg      960
gccaacgatg ataagaaact gctgacctgg cgtgaagaga ccggcaaaac cgcgtttgaa     1020
accgcgccgc agtatgaagg caaaatcggc gagcaggagt acttcgataa aggcgtactg     1080
atgattgcga tggtgaaagc gggcgttgaa ctggcgttcg aaaccatggt cgattccggc     1140
atcattgaag agtctgcata ttatgaatca ctgcacgagc tgccgctgat tgccaacacc     1200
atcgcccgta agcgtctgta cgaaatgaac gtggttatct ctgataccgc tgagtacggt     1260
aactatctgt tctcttacgc ttgtgtgccg ttgctgaaac cgtttatggc agagctgcaa     1320
ccgggcgacc tgggtaaagc tattccggaa ggcgcggtag ataacgggca actgcgtgat     1380
gtgaacgaag cgattcgcag ccatgcgatt gagcaggtag gtaagaaact gcgcggctat     1440
atgacagata tgaaacgtat tgctgttgcg ggttaa                              1476
```

<210> SEQ ID NO 32
<211> LENGTH: 491
<212> TYPE: PRT
<213> ORGANISM: Escherichia coli

<400> SEQUENCE: 32

```
Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190
```

```
Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
        210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 33
<211> LENGTH: 1851
<212> TYPE: DNA
<213> ORGANISM: Escherichia coli

<400> SEQUENCE: 33
atgcctaagt accgttccgc caccaccact catggtcgta atatggcggg tgctcgtgcg      60
ctgtggcgcg ccaccggaat gaccgacgcc gatttcggta agccgattat cgcggttgtg     120
aactcgttca cccaatttgt accgggtcac gtccatctgc gcgatctcgg taaactggtc     180
gccgaacaaa ttgaagcggc tggcggcgtt gccaaagagt caacaccat gcggtggat      240 gatgggattg ccatgggcca cgggggatg ctttattcac tgccatctcg cgaactgatc     300
gctgattccg ttgagtatat ggtcaacgcc cactgcgccg acgccatggt ctgcatctct     360
aactgcgaca aaatcacccc ggggatgctg atggcttccc tgcgcctgaa attccggtg     420
```

```
atctttgttt ccggcggccc gatggaggcc gggaaaacca aactttccga tcagatcatc    480
aagctcgatc tggttgatgc gatgatccag ggcgcagacc cgaaagtatc tgactcccag    540
agcgatcagg ttgaacgttc gcgtgtccg acctgcggtt cctgctccgg gatgtttacc    600
gctaactcaa tgaactgcct gaccgaagcg ctgggcctgt cgcagccggg caacggctcg    660
ctgctggcaa cccacgccga ccgtaagcag ctgttcctta tgctggtaa cgcattgtt     720
gaattgacca aacgttatta cgagcaaaac gacgaaagtg cactgccgcg taatatcgcc    780
agtaaggcgg cgtttgaaaa cgccatgacg ctggatatcg cgatgggtgg atcgactaac    840
accgtacttc acctgctggc ggcggcgcag gaagcggaaa tcgacttcac catgagtgat    900
atcgataagc tttcccgcaa ggttccacag ctgtgtaaag ttgcgccgag cacccagaaa    960
taccatatgg aagatgttca ccgtgctggt ggtgttatcg gtattctcgg cgaactggat   1020
cgcgcgggt tactgaaccg tgatgtgaaa aacgtacttg gcctgacgtt gccgcaaacg    1080
ctggaacaat acgacgttat gctgaccag gatgacgcgg taaaaatat gttccgcgca     1140
ggtcctgcag gcattcgtac cacacaggca ttctcgcaag attgccgttg ggatacgctg   1200
gacgacgatc gcgccaatgg ctgtatccgc tcgctggaac acgcctacag caaagacggc   1260
ggcctggcgg tgctctacgg taactttgcg gaaaacggct gcatcgtgaa acggcaggc    1320
gtcgatgaca gcatcctcaa attcaccggc ccggcgaaa tgtacgaaag ccaggacgat    1380
gcggtagaag cgattctcgg cggtaaagtt gtcgccggag atgtggtagt aattcgctat    1440
gaaggcccga aggcggtcc ggggatgcag gaaatgctct acccaaccag cttcctgaaa    1500
tcaatgggtc tcggcaaagc ctgtgcgctg atcaccgacg tcgtttctc tggtggcacc    1560
tctggtcttt ccatcggcca cgtctcaccg gaagcggcaa gcggcggcag cattggcctg   1620
attgaagatg gtgacctgat cgctatcgac atcccgaacc gtggcattca gttacaggta   1680
agcgatgccg aactggcggc gcgtcgtgaa gcgcaggacg ctcgaggtga caaagcctgg   1740
acgccgaaaa atcgtgaacg tcaggtctcc tttgccctgc gtgcttatgc cagcctggca   1800
accagcgccg acaaaggcgc ggtgcgcgat aaatcgaaac tgggggttta a            1851
```

<210> SEQ ID NO 34
<211> LENGTH: 616
<212> TYPE: PRT
<213> ORGANISM: Escherichia coli

<400> SEQUENCE: 34

```
Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
```

-continued

```
            115                 120                 125
Met Leu Met Ala Ser Leu Arg Leu Asn Ile Pro Val Ile Phe Val Ser
        130                 135                 140
Gly Gly Pro Met Glu Ala Gly Lys Thr Lys Leu Ser Asp Gln Ile Ile
145                 150                 155                 160
Lys Leu Asp Leu Val Asp Ala Met Ile Gln Gly Ala Asp Pro Lys Val
                165                 170                 175
Ser Asp Ser Gln Ser Asp Gln Val Glu Arg Ser Ala Cys Pro Thr Cys
                180                 185                 190
Gly Ser Cys Ser Gly Met Phe Thr Ala Asn Ser Met Asn Cys Leu Thr
        195                 200                 205
Glu Ala Leu Gly Leu Ser Gln Pro Gly Asn Gly Ser Leu Leu Ala Thr
        210                 215                 220
His Ala Asp Arg Lys Gln Leu Phe Leu Asn Ala Gly Lys Arg Ile Val
225                 230                 235                 240
Glu Leu Thr Lys Arg Tyr Tyr Glu Gln Asn Asp Glu Ser Ala Leu Pro
                245                 250                 255
Arg Asn Ile Ala Ser Lys Ala Ala Phe Glu Asn Ala Met Thr Leu Asp
                260                 265                 270
Ile Ala Met Gly Gly Ser Thr Asn Thr Val Leu His Leu Leu Ala Ala
            275                 280                 285
Ala Gln Glu Ala Glu Ile Asp Phe Thr Met Ser Asp Ile Asp Lys Leu
        290                 295                 300
Ser Arg Lys Val Pro Gln Leu Cys Lys Val Ala Pro Ser Thr Gln Lys
305                 310                 315                 320
Tyr His Met Glu Asp Val His Arg Ala Gly Val Ile Gly Ile Leu
                325                 330                 335
Gly Glu Leu Asp Arg Ala Gly Leu Leu Asn Arg Asp Val Lys Asn Val
                340                 345                 350
Leu Gly Leu Thr Leu Pro Gln Thr Leu Glu Gln Tyr Asp Val Met Leu
            355                 360                 365
Thr Gln Asp Asp Ala Val Lys Asn Met Phe Arg Ala Gly Pro Ala Gly
        370                 375                 380
Ile Arg Thr Thr Gln Ala Phe Ser Gln Asp Cys Arg Trp Asp Thr Leu
385                 390                 395                 400
Asp Asp Asp Arg Ala Asn Gly Cys Ile Arg Ser Leu Glu His Ala Tyr
                405                 410                 415
Ser Lys Asp Gly Gly Leu Ala Val Leu Tyr Gly Asn Phe Ala Glu Asn
                420                 425                 430
Gly Cys Ile Val Lys Thr Ala Gly Val Asp Asp Ser Ile Leu Lys Phe
            435                 440                 445
Thr Gly Pro Ala Lys Val Tyr Glu Ser Gln Asp Ala Val Glu Ala
        450                 455                 460
Ile Leu Gly Gly Lys Val Val Ala Gly Asp Val Val Ile Arg Tyr
465                 470                 475                 480
Glu Gly Pro Lys Gly Gly Pro Gly Met Gln Glu Met Leu Tyr Pro Thr
                485                 490                 495
Ser Phe Leu Lys Ser Met Gly Leu Gly Lys Ala Cys Ala Leu Ile Thr
                500                 505                 510
Asp Gly Arg Phe Ser Gly Gly Thr Ser Gly Leu Ser Ile Gly His Val
            515                 520                 525
Ser Pro Glu Ala Ala Ser Gly Gly Ser Ile Gly Leu Ile Glu Asp Gly
        530                 535                 540
```

```
Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
            565                 570                 575

Asp Lys Ala Trp Thr Pro Lys Asn Arg Glu Arg Gln Val Ser Phe Ala
        580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
        610                 615

<210> SEQ ID NO 35
<211> LENGTH: 1662
<212> TYPE: DNA
<213> ORGANISM: Lactococcus lactis

<400> SEQUENCE: 35
tctagacata tgtatactgt gggggattac ctgctggatc gcctgcacga actggggatt      60
gaagaaattt tcggtgtgcc aggcgattat aacctgcagt tcctggacca gattatctcg     120
cacaaagata tgaagtgggt cggtaacgcc aacgaactga cgcgagcta tatggcagat     180 ggttatgccc gtaccaaaaa agctgctgcg tttctgacga cctttggcgt tggcgaactg     240
agcgccgtca acggactggc aggaagctac gccgagaacc tgccagttgt cgaaattgtt     300
gggtcgccta cttctaaggt tcagaatgaa ggcaaatttg tgcaccatac tctggctgat     360
ggggatttta aacatttat gaaaatgcat gaaccggtta ctgcggcccg cacgctgctg     420
acagcagaga tgctacggt tgagatcgac cgcgtcctgt ctgcgctgct gaaagagcgc     480
aagccggtat atatcaatct gcctgtcgat gttgccgcag cgaaagccga aaagccgtcg     540
ctgccactga aaaagaaaa cagcacctcc aatacatcgg accaggaaat tctgaataaa     600
atccaggaat cactgaagaa tgcgaagaaa ccgatcgtca tcaccggaca tgagatcatc     660
tcttttggcc tggaaaaaac ggtcacgcag ttcatttcta agaccaaact gcctatcacc     720
accctgaact tcggcaaatc tagcgtcgat gaagcgctgc cgagttttct gggtatctat     780
aatggtaccc tgtccgaacc gaacctgaaa gaattcgtcg aaagcgcgga ctttatcctg     840
atgctgggcg tgaaactgac ggatagctcc acaggcgcat ttacccacca tctgaacgag     900
aataaaatga tttccctgaa atcgacgaa ggcaaaatct taacgagcg catccagaac     960 ttcgatttg aatctctgat tagttcgctg ctggatctgt ccgaaattga gtataaaggt    1020
aaatatattg ataaaaaaca ggaggatttt gtgccgtcta atgcgctgct gagtcaggat    1080
cgtctgtggc aagccgtaga aaacctgaca cagtctaatg aaacgattgt tgcggaacag    1140
ggaacttcat ttttcggcgc ctcatccatt tttctgaaat ccaaaagcca tttcattggc    1200
caaccgctgt gggggagtat tggttatacc tttccggcgg cgctgggttc acagattgca    1260
gataaggaat cacgccatct gctgtttatt ggtgacggca gcctgcagct gactgtccag    1320
gaactggggc tggcgatccg tgaaaaaatc aatccgattt gctttatcat caataacgac    1380
ggctacaccg tcgaacgcga aattcatgga ccgaatcaaa gttacaatga catcccgatg    1440
tggaactata gcaaactgcc ggaatccttt ggcgcgacag aggatcgcgt ggtgagtaaa    1500
attgtgcgta cggaaaacga atttgtgtcg gttatgaaag aagcgcaggc tgacccgaat    1560
cgcatgtatt ggattgaact gatcctggca aagaaggcg caccgaaagt tctgaaaaag    1620
atggggaaac tgtttgcgga gcaaaataaa agctaaggat cc                      1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
```

| | | | | | | | | | | | | |
|---|---|---|---|---|---|---|---|---|---|---|---|---|
| | | 370 | | | 375 | | | 380 | | | | |
| Ser | Ser | Ile | Phe | Leu | Lys | Ser | Lys | Ser | His | Phe | Ile | Gly | Gln | Pro | Leu |
| 385 | | | | | 390 | | | | | 395 | | | | | 400 |

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 37
<211> LENGTH: 1164
<212> TYPE: DNA
<213> ORGANISM: Escherichia coli

<400> SEQUENCE: 37

```
atgaacaact ttaatctgca caccccaacc cgcattctgt ttggtaaagg cgcaatcgct    60
ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctg   180
gaatttggcg gtattgagcc aaacccggct tatgaaacgc tgatgaacgc cgtgaaactg   240
gttcgcgaac agaaagtgac tttcctgctg gcggttggcg gcggttctgt actggacggc   300
accaaattta tcgccgcagc ggctaactat ccggaaaata tcgatccgtg cacattctg    360
caaacgggcg taaagagat aaaagcgcc atcccgatgg ctgtgtgct gacgctgcca    420
gcaaccggtt cagaatccaa cgcaggcgcg gtgatctccc gtaaaaccac aggcgacaag   480
caggcgttcc attctgccca tgttcagccg gtatttgccg tgctcgatcc ggtttatacc   540
tacaccctgc cgccgcgtca ggtggctaac ggcgtagtgg acgcctttgt acacaccgtg   600
gaacagtatg ttaccaaacc ggttgatgcc aaaattcagg accgtttcgc agaaggcatt   660
ttgctgacgc taatcgaaga tggtccgaaa gccctgaaag agccagaaaa ctacgatgtg   720
cgcgccaacg tcatgtgggc ggcgactcag cgctgaacg gtttgattgg cgctggcgta   780
ccgcaggact gggcaacgca tatgctgggc acgaactga ctgcgatgca cggtctggat   840
cacgcgcaaa cactggctat cgtcctgcct gcactgtgga tgaaaaacg cgataccaag   900
cgcgctaagc tgctgcaata tgctgaacgc gtctggaaca tcactgaagg ttccgatgat   960
gagcgtattg acgccgcgat tgccgcaacc cgcaatttct ttgagcaatt aggcgtgccg  1020
acccacctct ccgactacgg tctggacggc agctccatcc cggctttgct gaaaaaactg  1080
```

-continued

```
gaagagcacg gcatgaccca actgggcgaa aatcatgaca ttacgttgga tgtcagccgc    1140
cgtatatacg aagccgcccg ctaa                                           1164
```

<210> SEQ ID NO 38
<211> LENGTH: 387
<212> TYPE: PRT
<213> ORGANISM: Escherichia coli

<400> SEQUENCE: 38

```
Met Asn Asn Phe Asn Leu His Thr Pro Thr Arg Ile Leu Phe Gly Lys
1               5                  10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
```

```
                355                 360                 365
Gly Glu Asn His Asp Ile Thr Leu Asp Val Ser Arg Arg Ile Tyr Glu
    370                 375                 380

Ala Ala Arg
385

<210> SEQ ID NO 39
<211> LENGTH: 1197
<212> TYPE: DNA
<213> ORGANISM: Saccharomyces cerevisiae

<400> SEQUENCE: 39
atgtctcaga acgtttacat tgtatcgact gccagaaccc caattggttc attccagggt     60
tctctatcct ccaagacagc agtggaattg ggtgctgttg ctttaaaagg cgccttggct    120
aaggttccag aattggatgc atccaaggat tttgacgaaa ttattttttgg taacgttctt   180 tctgccaatt tgggccaagc tccggccaga caagttgctt tggctgccgg tttgagtaat    240
catatcgttg caagcacagt taacaaggtc tgtgcatccg ctatgaaggc aatcattttg    300
ggtgctcaat ccatcaaatg tggtaatgct gatgttgtcg tagctggtgg ttgtgaatct    360
atgactaacg caccatacta catgccagca gcccgtgcgg gtgccaaatt tggccaaact    420
gttcttgttg atggtgtcga agagatgggg ttgaacgatg cgtacgatgg tctagccatg    480
ggtgtacacg cagaaaagtg tgcccgtgat tgggatatta ctagagaaca acaagacaat    540
tttgccatcg aatcctacca aaaatctcaa aaatctcaaa aggaaggtaa attcgacaat    600
gaaattgtac ctgttaccat taagggattt agaggtaagc ctgatactca agtcacgaag    660
gacgaggaac ctgctagatt acacgttgaa aaattgagat ctgcaaggac tgttttccaa    720
aaagaaaacg gtactgttac tgccgctaac gcttctccaa tcaacgatgg tgctgcagcc    780
gtcatcttgg tttccgaaaa agttttgaag gaaaagaatt tgaagccttt ggctattatc    840
aaaggttggg gtgaggccgc tcatcaacca gctgatttta catgggctcc atctcttgca    900
gttccaaagg ctttgaaaca tgctggcatc gaagacatca attctgttga ttactttgaa    960
ttcaatgaag ccttttcggt tgtcggtttg gtgaacacta gattttgaa gctagaccca   1020 tctaaggtta atgtatatgg tggtgctgtt gctctaggtc acccattggg ttgttctggt   1080
gctagagtgg ttgttacact gctatccatc ttacagcaag aaggaggtaa gatcggtgtt   1140
gccgccattt gtaatggtgg tggtggtgct tcctctattg tcattgaaaa gatatga     1197

<210> SEQ ID NO 40
<211> LENGTH: 398
<212> TYPE: PRT
<213> ORGANISM: Saccharomyces cerevisiae

<400> SEQUENCE: 40

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80
```

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395

<210> SEQ ID NO 41
<211> LENGTH: 1716
<212> TYPE: DNA
<213> ORGANISM: Bacillus subtilis

<400> SEQUENCE: 41
atgttgacaa agcaacaaa agaacaaaaa tcccttgtga aaacagagg ggcggagctt    60 gttgttgatt gcttagtgga gcaaggtgtc acacatgtat ttggcattcc aggtgcaaaa   120
attgatgcgg tatttgacgc tttacaagat aaaggacctg aaattatcgt tgcccggcac   180
gaacaaaacg cagcattcat ggcccaagca gtcggccgtt taactggaaa accgggagtc   240
gtgttagtca catcaggacc gggtgcctct aacttggcaa caggcctgct gacagcgaac   300
actgaaggag accctgtcgt tgcgcttgct ggaaacgtga tccgtgcaga tcgttttaaa   360

```
cggacacatc aatctttgga taatgcggcg ctattccagc cgattacaaa atacagtgta      420
gaagttcaag atgtaaaaaa tataccggaa gctgttacaa atgcatttag gatagcgtca      480
gcagggcagg ctggggccgc ttttgtgagc tttccgcaag atgttgtgaa tgaagtcaca      540
aatacgaaaa acgtgcgtgc tgttcagcg ccaaaactcg gtcctgcagc agatgatgca       600
atcagtgcgg ccatagcaaa aatccaaaca gcaaaacttc ctgtcgtttt ggtcggcatg      660
aaaggcggaa gaccggaagc aattaaagcg gttcgcaagc ttttgaaaaa ggttcagctt      720
ccatttgttg aaacatatca agctgccggt acccttccta gagatttaga ggatcaatat      780
tttggccgta tcggtttgtt ccgcaaccag cctggcgatt tactgctaga gcaggcagat      840
gttgttctga cgatcggcta tgacccgatt gaatatgatc cgaaattctg aatatcaat       900 ggagaccgga caattatcca tttagacgag attatcgctg acattgatca tgcttaccag      960
cctgatcttg aattgatcgg tgacattccg tccacgatca atcatatcga acacgatgct     1020
gtgaaagtgg aatttgcaga gcgtgagcag aaaatccttt ctgatttaaa acaatatatg     1080
catgaaggtg agcaggtgcc tgcagattgg aaatcagaca gagcgcaccc tcttgaaatc     1140
gttaaagagt tgcgtaatgc agtcgatgat catgttacag taacttgcga tatcggttcg     1200
cacgccattt ggatgtcacg ttatttccgc agctacgagc cgttaacatt aatgatcagt     1260
aacggtatgc aaacactcgg cgttgcgctt ccttgggcaa tcggcgcttc attggtgaaa     1320
ccgggagaaa aagtggtttc tgtctctggt gacgcggtt tcttattctc agcaatggaa      1380
ttagagacag cagttcgact aaaagcacca attgtacaca ttgtatggaa cgacagcaca     1440
tatgacatgg ttgcattcca gcaattgaaa aaatataacc gtacatctgc ggtcgatttc     1500
ggaaatatcg atatcgtgaa atatgcggaa agcttcggag caactggctt gcgcgtagaa     1560
tcaccagacc agctggcaga tgttctgcgt caaggcatga acgctgaagg tcctgtcatc     1620
atcgatgtcc cggttgacta cagtgataac attaatttag caagtgacaa gcttccgaaa     1680
gaattcgggg aactcatgaa aacgaaagct ctctag                               1716
```

<210> SEQ ID NO 42
<211> LENGTH: 571
<212> TYPE: PRT
<213> ORGANISM: Bacillus subtilis

<400> SEQUENCE: 42

Met Leu Thr Lys Ala Thr Lys Glu Gln Lys Ser Leu Val Lys Asn Arg
1               5                   10                  15

Gly Ala Glu Leu Val Val Asp Cys Leu Val Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

-continued

```
Ala Ala Leu Phe Gln Pro Ile Thr Lys Tyr Ser Val Glu Val Gln Asp
        130                 135                 140

Val Lys Asn Ile Pro Glu Ala Val Thr Asn Ala Phe Arg Ile Ala Ser
145                 150                 155                 160

Ala Gly Gln Ala Gly Ala Phe Val Ser Phe Pro Gln Asp Val Val
                165                 170                 175

Asn Glu Val Thr Asn Thr Lys Asn Val Arg Ala Val Ala Ala Pro Lys
                180                 185                 190

Leu Gly Pro Ala Ala Asp Asp Ala Ile Ser Ala Ala Ile Ala Lys Ile
                195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
                260                 265                 270

Asp Leu Leu Leu Glu Gln Ala Asp Val Val Leu Thr Ile Gly Tyr Asp
                275                 280                 285

Pro Ile Glu Tyr Asp Pro Lys Phe Trp Asn Ile Asn Gly Asp Arg Thr
                290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
                340                 345                 350

Leu Ser Asp Leu Lys Gln Tyr Met His Glu Gly Glu Gln Val Pro Ala
                355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
                420                 425                 430

Ala Ile Gly Ala Ser Leu Val Lys Pro Gly Glu Lys Val Val Ser Val
                435                 440                 445

Ser Gly Asp Gly Gly Phe Leu Phe Ser Ala Met Glu Leu Glu Thr Ala
                450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
                500                 505                 510

Gly Ala Thr Gly Leu Arg Val Glu Ser Pro Asp Gln Leu Ala Asp Val
                515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
```

```
545                 550                 555                 560

Glu Phe Gly Glu Leu Met Lys Thr Lys Ala Leu
                565                 570
```

<210> SEQ ID NO 43
<211> LENGTH: 1188
<212> TYPE: DNA
<213> ORGANISM: Saccharomyces cerevisiae

<400> SEQUENCE: 43

```
atgttgagaa ctcaagccgc cagattgatc tgcaactccc gtgtcatcac tgctaagaga     60
acctttgctt tggccacccg tgctgctgct tacagcagac cagctgcccg tttcgttaag    120
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc aggcaagaa cttgttcact gttgaagatg ctatcaagag aggtagttac    420
gttatgaact tgttgtccga tgccgctcaa tcagaaaccct ggcctgctat caagccattg    480
ttgaccaagg gtaagacttt gtacttctcc cacggtttct ccccagtctt caaggacttg    540
actcacgttg aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact ccccatctga agctttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa              1188
```

<210> SEQ ID NO 44
<211> LENGTH: 395
<212> TYPE: PRT
<213> ORGANISM: Saccharomyces cerevisiae

<400> SEQUENCE: 44

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
                20                  25                  30

Arg Pro Ala Ala Arg Phe Val Lys Pro Met Ile Thr Thr Arg Gly Leu
            35                  40                  45

Lys Gln Ile Asn Phe Gly Gly Thr Val Glu Thr Val Tyr Glu Arg Ala
        50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95
```

Arg Asp Asn Gly Leu Asn Val Ile Ile Gly Val Arg Lys Asp Gly Ala
              100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
        130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395

```
<210> SEQ ID NO 45
<211> LENGTH: 1476
<212> TYPE: DNA
<213> ORGANISM: Bacillus subtilis

<400> SEQUENCE: 45
atggctaact acttcaatac actgaatctg cgccagcagc tggcacagct gggcaaatgt      60
cgctttatgg gccgcgatga attcgccgat ggcgcgagct accttcaggg taaaaaagta     120
gtcatcgtcg gctgtggcgc acagggtctg aaccagggcc tgaacatgcg tgattctggt     180
ctcgatatct cctacgctct gcgtaaagaa gcgattgccg agaagcgcgc gtcctggcgt     240
aaagcgaccg aaaatggttt taaagtgggt acttacgaag aactgatccc acaggcggat     300
ctggtgatta acctgacgcc ggacaagcag cactctgatg tagtgcgcac cgtacagcca     360
ctgatgaaag acggcgcggc gctgggctac tcgcacggtt tcaacatcgt cgaagtgggc     420
```

-continued

```
gagcagatcc gtaaagatat caccgtagtg atggttgcgc cgaaatgccc aggcaccgaa    480
gtgcgtgaag agtacaaacg tgggttcggc gtaccgacgc tgattgccgt tcacccggaa    540
aacgatccga aggcgaagg catggcgatt gccaaagcct gggcggctgc aaccggtggt    600
caccgtgcgg gtgtgctgga atcgtccttc gttgcggaag tgaaatctga cctgatgggc    660
gagcaaacca tcctgtgcgg tatgttgcag gctggctctc tgctgtgctt cgacaagctg    720
gtggaagaag gtaccgatcc agcatacgca gaaaaactga ttcagttcgg ttgggaaacc    780
atcaccgaag cactgaaaca gggcggcatc accctgatga tggaccgtct ctctaacccg    840
gcgaaactgc gtgcttatgc gctttctgaa cagctgaaag agatcatggc acccctgttc    900
cagaaacata tggacgacat catctccggc gaattctctt ccggtatgat ggcggactgg    960
gccaacgatg ataagaaact gctgacctgg cgtgaagaga ccggcaaaac cgcgtttgaa   1020
accgcgccgc agtatgaagg caaaatcggc gagcaggagt acttcgataa aggcgtactg   1080
atgattgcga tggtgaaagc gggcgttgaa ctggcgttcg aaaccatggt cgattccggc   1140
atcattgaag agtctgcata ttatgaatca ctgcacgagc tgccgctgat tgccaacacc   1200
atcgcccgta agcgtctgta cgaaatgaac gtggttatct ctgataccgc tgagtacggt   1260
aactatctgt tctcttacgc ttgtgtgccg ttgctgaaac cgtttatggc agagctgcaa   1320
ccgggcgacc tgggtaaagc tattccggaa ggcgcggtag ataacgggca actgcgtgat   1380
gtgaacgaag cgattcgcag ccatgcgatt gagcaggtag gtaagaaact gcgcggctat   1440
atgacagata tgaaacgtat tgctgttgcg ggttaa                             1476
```

<210> SEQ ID NO 46
<211> LENGTH: 342
<212> TYPE: PRT
<213> ORGANISM: Bacillus subtilis

<400> SEQUENCE: 46

Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Lys Val Tyr Glu Ala Glu Ile Lys Asp Glu
            85                  90                  95

Leu Thr Ala Gly Lys Ser Leu Val Phe Ala His Gly Phe Asn Val His
        100                 105                 110

Phe His Gln Ile Val Pro Pro Ala Asp Val Asp Val Phe Leu Val Ala
    115                 120                 125

Pro Lys Gly Pro Gly His Leu Val Arg Arg Thr Tyr Glu Gln Gly Ala
130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
            165                 170                 175

Gly Val Leu Glu Thr Thr Phe Lys Glu Glu Thr Glu Thr Asp Leu Phe
        180                 185                 190

```
Gly Glu Gln Ala Val Leu Cys Gly Gly Leu Ser Ala Leu Val Lys Ala
            195                 200                 205
Gly Phe Glu Thr Leu Thr Glu Ala Gly Tyr Gln Pro Glu Leu Ala Tyr
        210                 215                 220
Phe Glu Cys Leu His Glu Leu Lys Leu Ile Val Asp Leu Met Tyr Glu
225                 230                 235                 240
Glu Gly Leu Ala Gly Met Arg Tyr Ser Ile Ser Asp Thr Ala Gln Trp
                245                 250                 255
Gly Asp Phe Val Ser Gly Pro Arg Val Val Asp Ala Lys Val Lys Glu
            260                 265                 270
Ser Met Lys Glu Val Leu Lys Asp Ile Gln Asn Gly Thr Phe Ala Lys
        275                 280                 285
Glu Trp Ile Val Glu Asn Gln Val Asn Arg Pro Arg Phe Asn Ala Ile
    290                 295                 300
Asn Ala Ser Glu Asn Glu His Gln Ile Glu Val Val Gly Arg Lys Leu
305                 310                 315                 320
Arg Glu Met Met Pro Phe Val Lys Gln Gly Lys Lys Glu Ala Val
                325                 330                 335
Val Ser Val Ala Gln Asn
            340

<210> SEQ ID NO 47
<211> LENGTH: 1758
<212> TYPE: DNA
<213> ORGANISM: Saccharomyces cerevisiae

<400> SEQUENCE: 47
atgggcttgt taacgaaagt tgctacatct agacaattct ctacaacgag atgcgttgca      60
aagaagctca acaagtactc gtatatcatc actgaaccta agggccaagg tgcgtcccag     120
gccatgcttt atgccaccgg tttcaagaag gaagatttca agaagcctca gtcggggtt     180 ggttcctgtt ggtggtccgg taacccatgt aacatgcatc tattggactt gaataacaga     240
tgttctcaat ccattgaaaa agcgggtttg aaagctatgc agttcaacac catcggtgtt     300
tcagacggta tctctatggg tactaaaggt atgagatact cgttacaaag tagagaaatc     360
attgcagact cctttgaaac catcatgatg gcacaacact acgatgctaa catcgccatc     420
ccatcatgtg acaaaaacat gcccggtgtc atgatggcca tgggtagaca taacagacct     480
tccatcatgg tatatggtgg tactatcttg cccggtcatc aacatgtgg ttcttcgaag     540 atctctaaaa acatcgatat cgtctctgcg ttccaatcct acggtgaata tatttccaag     600
caattcactg aagaagaaag agaagatgtt gtggaacatg catgcccagg tcctggttct     660
tgtggtggta tgtatactgc caacacaatg gcttctgccg ctgaagtgct aggttttgacc     720 attccaaaact cctcttcctt cccagccgtt tccaaggaga agttagctga gtgtgacaac     780
attggtgaat acatcaagaa gacaatggaa ttgggtatt tacctcgtga tatcctcaca     840
aaagaggctt ttgaaaacgc cattacttat gtcgttgcaa ccggtgggtc cactaatgct     900
gttttgcatt tggtggctgt tgctcactct gcgggtgtca gttgtcacc agatgatttc     960 caaagaatca gtgatactac accattgatc ggtgacttca aaccttctgg taaatacgtc    1020
atggccgatt tgattaacgt tggtggtacc caatctgtga ttaagtatct atatgaaaac    1080
aacatgttgc acggtaacac aatgactgtt accggtgaca ctttggcaga acgtgcaaag    1140
aaagcaccaa gcctacctga aggacaagag attattaagc cactctccca cccaatcaag    1200
```

-continued

```
gccaacggtc acttgcaaat tctgtacggt tcattggcac caggtggagc tgtgggtaaa    1260
attaccggta aggaaggtac ttacttcaag ggtagagcac gtgtgttcga agaggaaggt    1320
gcctttattg aagccttgga aagaggtgaa atcaagaagg gtgaaaaaac cgttgttgtt    1380
atcagatatg aaggtccaag aggtgcacca ggtatgcctg aaatgctaaa gccttcctct    1440
gctctgatgg gttacggttt gggtaaagat gttgcattgt tgactgatgg tagattctct    1500
ggtggttctc acgggttctt aatcggccac attgttcccg aagccgctga aggtggtcct    1560
atcgggttgg tcagagacgg cgatgagatt atcattgatg ctgataataa caagattgac    1620
ctattagtct ctgataagga aatggctcaa cgtaaacaaa gttgggttgc acctccacct    1680
cgttacacaa gaggtactct atccaagtat gctaagttgg tttccaacgc ttccaacggt    1740
tgtgttttag atgcttga                                                  1758
```

<210> SEQ ID NO 48
<211> LENGTH: 585
<212> TYPE: PRT
<213> ORGANISM: Saccharomyces cerevisiae

<400> SEQUENCE: 48

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270
```

Ile Leu Pro Arg Asp Ile Leu Thr Lys Glu Ala Phe Glu Asn Ala Ile
            275                 280                 285

Thr Tyr Val Val Ala Thr Gly Gly Ser Thr Asn Ala Val Leu His Leu
        290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
        435                 440                 445

Gly Glu Ile Lys Lys Gly Glu Lys Thr Val Val Ile Arg Tyr Glu
        450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510

Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585

<210> SEQ ID NO 49
<211> LENGTH: 8019
<212> TYPE: DNA
<213> ORGANISM: Saccharomyces cerevisiae

<400> SEQUENCE: 49
atgacagcta tcttaaactg ggaagatata tcccctgttt tagagaaagg cacccgcgaa      60
tcacacgtgt ctaaaagagt tccctttttg caagatatat cacaattagt tcgtcaagaa     120
acattggaaa aacctcaatt atctgaaatt gctttcgttt tattgaatac cttcacgatt     180
tacgaagaca ataggtctaa aagtttggta acttcaatat tgcttgacat cttaaatcta     240
gagccatgtc tcctagaaaa ctttatccga ttcatttccg acgtggtcat cagtaatccg     300
gctaccaaag cagtcgctga ttaccttaat ttgttagatt ggattaattc tttcttgatt     360

```
tttgtgtcgc ataattctaa tttatttgaa gagtacattc caaaattgtt ggtcgcccat    420
tcttatgcaa cgttcggtgt ggaaactatt cttgacaatc aagaagaagg caagaaatcc    480
caagataagc agaaccagca tagaaagaga attcgttatt gcattttcca acaacggtc     540 aaagcattcc ttaagtgctt gaaggataat gacgacagta tttccttcat gaagatttca    600
attaaaactg tactggagag ctactctaag ctgaagataa ccagtgttgg agtagttatg    660
ataatgggtg cactaactca ggctgcactt cagttattat cgaggcaacc agctctgcac    720
tccgttttaa aggaaaattc tgcagagaaa tattgcgaat atttgggcaa agaagtgttt    780
ttaggcaaaa acccaccatc ttccttttgc ttagagattg gtttgaagcc attttttaaa    840
gaatttgttt cacaagagtt attcattaag ttttttcatcc ctaatattga aaaagcagtt    900
ttaagatctc ctgaggttgg ttttttcgatt ttatctgagt tatatgctgg tgtttctcct    960
gaaaaagtaa atctcttaaa tgcctttgct tcctcgaaac tgattaatca atacttctcg   1020
tcatttaaaa gctcaaaaga ggtagttaga tccgtctcgc ttcagtctat gataatctta   1080
ttgagaaaaa tttccaatac tgacactacc ttggaagatt tgaccaagct tattgacgaa   1140
atatttaaga acatcaaatc gaacttaaat gcagattaca aatcacttat ttccaaaatt   1200
ctcatagaaa taccottaac gcactatgag gtttcagaaa aaatctgcaa agggctgtcc   1260
ccatatattg gtaaagaagg taatgaagca gccttgactc taatgcttaa cgcttttttt   1320
gttcattatt ttagtctggg caaacctatt gaagacttgg ataaaattat atcagctggt   1380
tttgcagata aaaaacctgc tttgaaaaaa tgctggtttg ccgcattttt gaacaattcc   1440
aatgctgcct ctgaagaggt gattttaaac tttatagacg gttgtttgga atttgtgaaa   1500
gactccatca tacattatca gactcacggg catgcatgta ttctagcatc aattgaattt   1560
acaaacaaaa ttttggcatt ggacaatact gagctaaatg atcgtgttat gcagctcata   1620
gaaacccttc ctgaaaattc ttcgataggt gatgctatct taactgctgc attatcaaca   1680
gagctatcca tcgaaaaccg tattcatgct gttaatttac tacaagaatt gttctacaag   1740
aaacccgaat ttattgggtt tagcgtgatt gatgcaattg aaggagaat gcgtgtccaa    1800 gaattaatac ctcaacaaaa tacatccttt aaatatgtca cttctgtact actgccatt    1860 acgtctgagt tacctgacaa ggaagcctcg ataaaggtat taatcaatgc tctggtcata   1920
gcgcaatgga atattttcaa cattaagaat ggctgggctg gtttagtttt acgtgcaagg   1980
cttgatccag ctgaagttgt caaagaacat gctagcgtta tcatggagaa gattcttgaa   2040
atcacaggta gttgtgaatg gatagataca atttatggtg catgcggttt gcaagcagct   2100
gcctatgcag catttattca gcctaatgag ttcacaccga tcctttgtaa gactatcgaa   2160
gcagatttaa ccgcgatga tttctcacgt ttatctgaag aggacttcga atttttgca    2220 ggagaggaag gtgttctggt ggttgacgtc ctggaagaaa gcatgaataa gaaactttcc   2280
aataaaaatt ctaaagagta cgaaactcta atgtgggaac aaaaaataag gaaggagcaa   2340
gccaaaaaga atgtgaaaaa actttcaaaa gaggaacaag agctcgttaa tgaacagtta   2400
gcgaaagaat ctgcagttag atcacacgtt tcggaaattt ccactcgttt aaagcgtggt   2460
attagattgg tatctgaact ttccaaagct gcttgcttaa tccaaaatgg catcgctact   2520
tggttcccct tggcagtcac aaagcttttg tacctatgct cggaaccaaa tatttcaaag   2580
ctaacagagg atgtaaataa tgtgttcttg cagcttctc aaaatgtctc cgagagatta    2640
ggtaatatca gacttttctt aggtttggcg actttgcgtg tgcacaatgc taatggcatc   2700
```

```
tcgcaagatt atttacaaga accactggtt gaattactta caagagttct ttttaggatc    2760
aagttcgtct ccaaccaagc agcaatagat tccatcagtt tgacatatat tttaccattg    2820
ttgattaatg ttttagaaaa gggtaaggcg attgcattaa agaatgcgga caagcctgtt    2880
gttaaggctg agtttgttga agaagatgaa gaagaagaac atctgttact ggccatggaa    2940
attatttctg tacacgctga agcttttgag gatccttcca ttccgagaat ttccattgtt    3000
gaagtgttac tatctcttct atctttaccc tcaaaagcga agattgctaa agattgtttc    3060
aacgctctgt gccaaagcat atctgttgca ccaaatcaag aagaccttga tatgatacta    3120
tcaaatttac tatcaccaaa tcaatttgtc cgttcaacaa tattagaaac tcttgataac    3180
gaattcgaat tagaaccttt tatgaaatat tcacctgaag ttttcatttg cagatttgat    3240
tcggatcctt ccaaccgcga gattgcagat ttcatttggg agttcaacaa atttgtagtc    3300
aacgatgaat tactaaaaag cttattccca ctattcaatc aggatgatag tggcttgaga    3360
ttatttgcgg caaacgcgta cgcatttggt gcggtaagtc tgtttacctc tgaagagaac    3420
tcctcgaaag attacttaaa tgatttgctg aacttttata agaaaaggc aaagccattg    3480 gagccaattc ttgatcaatt tggcttggtt cttgtttctg cgagtgaaca aaaagatcca    3540
tggcaaggaa gaagtaccgt tgctattaca ttaaaaatca tggctaaggc ttttctgca    3600 gaggatgata ctgtcgttaa cattataaaa ttttggtcg atgatggagg tctagtagac    3660
agagagccta ttgttcgtca agaaatgaaa gaagctggtg ttgaattaat tacgttacat    3720
ggctcacaaa actcgaagga tttaattcct atatttgaag aagcattaag ctccagtacg    3780
gacagtgcct taaagagaa cgttattatt ttgtatggta cattagcaag acatttacag    3840
caaagtgatg caaggattca cacgatcatt gaaagattgc tttcaacttt ggatactcct    3900
tctgcggata ttcaacaggc tgtgtcggct tgtatagcac cactagtttt ccagttcaaa    3960
caaaaagttg gtgattactt gggtatccta atggagaaac tgctgaatcc aactgttgct    4020
tcttctatgc ggaaaggtgc cgcttggggt atcgctggtt tagtgaaagg ttacggtatc    4080
tcggctctct cggagtttga cattattcgc aacctcatcg aagctgcaga agataaaaag    4140
gagccaaaaa gacgtgaatc tgttggcttc tgcttcaat atttgtctga atctctagga    4200
aagttttttg aaccatatgt gatagaaatt cttccaaata ttttaaagaa tttaggggat    4260
gctgttcctg aagttagaga tgcaaccgct cgtgccacta aggctataat ggcgcatact    4320
acaggttacg gtgttaaaaa gttaattcca gttgctgttt ctaatttgga tgaaattgct    4380
tggagaacta agagggggctc tgttcaattg ttgggtaata tggcttattt agatcctact    4440
caattgtcag cttctttgtc caccattgtc ccagaaattg ttggtgtatt gaacgactct    4500
cacaaagagg tgcgtaaggc cgctgatgaa tccttgaaaa gattcggtga agttatcaga    4560
aatccggaaa ttcagaaatt ggtgcccgta cttttgcaag ctatcggtga tccaacaaaa    4620
tacactgaag aggccttgga ttcgttaatt caaacacaat tgtccattta tattgatggt    4680
ccttcactag cactaattat tcatatatt catcgtggta tgcatgatag atctgccaac    4740
attaagagga aagcatgtaa gatcgtgggc aatatggcca ttttggttga taccaaagat    4800
ctcatcccat atttacaaca gctgatagat gaagtggaga ttgctatggt ggatccagtt    4860
ccaaatacta gagccacagc agcacgtgct ttgggtgctt tggtagaaag gttaggtgaa    4920
gagcaattcc cagatttgat tcctcgtcta ctagatacct taagtgacga atcaaaatct    4980
ggtgatcgtc tcggttctgc tcaagctcta gctgaagtta ttagtggctt gggcttgacc    5040
aagttggatg agatgttacc aaccattttg gctggtgtaa ccaattttcg tgcttatatc    5100
```

```
agggaaggat tcatgccttt gctgcttttc cttcctgttt gttttggatc acaatttgct    5160
ccatacatta atcagattat tcagcctatt ctttccggat tggccgataa tgatgaaaat    5220
attcgcgata ctgctttgaa ggctggtaaa ttaattgtca aaaactacgc tacaaaggcc    5280
gttgatttgt tgttgcctga attagaaagg ggtatgttcg atgaaaatga cagaattcgc    5340
ttatcttctg ttcaattaac cggagaacta ttgttccaag ttactggtat ttcctccagg    5400 aacgaattt ctgaggaaga tggtgatcat aatggtgaat tctctggtaa attggtcgat    5460
gtacttggcc aagaccgtcg tgatagaatt ttagccgcat tatttgtatg caggaacgac    5520
acttctggta tcgtacgtgc tacgacggtt gacatttgga aggcattggt tccaaatact    5580
ccaagagctg tgaaagagat ccttccaaca ttgactggta tgatagtcac tcacttggct    5640
tcatcatcca atgtattacg caacattgct gctcagacct taggtgatct tgtccgtcgt    5700
gtaggtggta atgctttgtc ccaactgtta ccaagtttgg aggaatcttt gatagaaaca    5760
tcaaactcag attcgagaca aggtgtttgt attgctcttt atgagttaat tgaatcggct    5820
tctacggaaa cgatatcaca gttccaatct accatcgtta acattattcg tacggcatta    5880
attgatgagt cggctactgt cagagaagcg gctgcattat cttttgatgt attccaagat    5940
gttgtaggaa aaactgctgt tgatgaagtt ttaccatatt tgttgcatat gcttgaatct    6000
tctgataatt ctgactttgc tttgttaggt ttacaagaaa ttatgtcgaa gaagtccgac    6060
gtaatcttcc aatttttaat tccaacccta ttagcccctc aatagacgc cttcagggct    6120 tctgctttag gttctttggc ggaagttgct ggctcagcct tatacaagcg tttatcaatt    6180
ataatcaacg cactagtgga tgcaatcata ggtacttctg aagatgaatc gaccaagggt    6240
gcattagaac ttgcattaga cagggtattc ttatctgtga atgatgacga aggtcttcac    6300
ccattacttc aacagattat gtcactacta aagagtgata atatagagaa acgcatagct    6360
gttttagaac gtttgccaaa tttcttcgat aagactgttc ttgattttga tgtctatatt    6420
ccgaactttg tctctcacgc aatttttatca ttagatgatg aagatcaaag ggttgttaat    6480
ggtaacttca atgctttgtc tactttgttg aagaaggttg ataagcccac cttagaaaaa    6540
ttagttaagc ctgctaaaca gtcattggca ttaacaggca ggcaaggtca agatgtcgct    6600
gcatttaagc ttccaagagg ccctaactgt gttttgccta ttttcttgca tggtttgatg    6660
tatggttcga atgatgaaag ggaagaatct gcattagcca ttgctgacgt tgtttcgaag    6720
acccctgccg ctaacttgaa gccatttgtg agcgtaatta ctggtccatt aattcgtgtc    6780
gtgggtgaaa gatttagtag tgatatcaaa gcagcaattt tatttgcact taatgtgcta    6840
ttcattaaga ttccaatgtt cttgaggcct tttatccctc aattacaaag aacatttgtt    6900
aaatccttgt ctgacgctac caatgaaacg ttacgtctcc gcgccgcaaa ggctcttggt    6960
gccctgattg aacatcagcc tcgtgttgac cctctagtca ttgaactggt gacaggtgcc    7020
aagcaagcca cagatgaagg tgtcaagact gcgatgctta agctttact ggaagttatt    7080 atgaaggctg gttccaaatt aaacgaaaat tctaagacaa acattgtcaa tttagttgag    7140
gaagaaatgt tgggtagcaa tgacaaattg gcagttgctt acgctaaatt aatcggatcg    7200
ttatcagaga ttttgtcgaa cgacgaagcc cacaagatat tgcaagacaa ggttttgaat    7260
gcagatctag atggagaaac cggtaagttt gctattctga ctttgaattc cttttttgaaa    7320 gatgcaccaa cacatatatt caatacgggc ttgatagacg aatttgtaag ttacattttg    7380
aatgcaatcc gttcccctga tgtttacttc ggagaaaatg gtaccattgc tgctggtaaa    7440
```

-continued

```
ttactttat tagaaggaga aaagaggtct ccatttgtta aaaaggatgc tgcagaacca    7500
ttcaaaattg gcgatgaaaa catcaatctg ttaattaatg agttgagcaa agctgtctta    7560
caaccagcca gtaattctac ggatgtaaga aggttggcct tggtggttat aagaacacta    7620
gccagattca aatttgacga gtgcattaag caatacttcg atgtagtagg accatctgta    7680
ttttcttgct tgcgtgatcc tgttatccca attaagctcg cagcagaaaa agcatattta    7740
gctttgttca aattggttga agaagatgac atgcatactt tcaacgagtg gtttgctaaa    7800
atttcagatc gcggtaacag catcgaaact gtcacaggta ctacaattca attacggtct    7860
gttggggact ataccaagag ggttggtaaa aggttagcaa atgtcgaaag agaaaggatt    7920
gctgccggag gagacgcgga acaatgtttt agtgacagat ttgaagatga agagaaata    7980 tgggctgtcg gaggtgttga attaaccact gatatttga                          8019
```

<210> SEQ ID NO 50
<211> LENGTH: 2672
<212> TYPE: PRT
<213> ORGANISM: Saccharomyces cerevisiae

<400> SEQUENCE: 50

```
Met Thr Ala Ile Leu Asn Trp Glu Asp Ile Ser Pro Val Leu Glu Lys
1               5                   10                  15

Gly Thr Arg Glu Ser His Val Ser Lys Arg Val Pro Phe Leu Gln Asp
            20                  25                  30

Ile Ser Gln Leu Val Arg Gln Glu Thr Leu Glu Lys Pro Gln Leu Ser
        35                  40                  45

Glu Ile Ala Phe Val Leu Leu Asn Thr Phe Thr Ile Tyr Glu Asp Asn
    50                  55                  60

Arg Ser Lys Ser Leu Val Thr Ser Ile Leu Leu Asp Ile Leu Asn Leu
65                  70                  75                  80

Glu Pro Cys Leu Leu Glu Asn Phe Ile Arg Phe Ile Ser Asp Val Val
                85                  90                  95

Ile Ser Asn Pro Ala Thr Lys Ala Val Ala Asp Tyr Leu Asn Leu Leu
            100                 105                 110

Asp Trp Ile Asn Ser Phe Leu Ile Phe Val Ser His Asn Ser Asn Leu
        115                 120                 125

Phe Glu Glu Tyr Ile Pro Lys Leu Leu Val Ala His Ser Tyr Ala Thr
    130                 135                 140

Phe Gly Val Glu Thr Ile Leu Asp Asn Gln Glu Glu Gly Lys Lys Ser
145                 150                 155                 160

Gln Asp Lys Gln Asn Gln His Arg Lys Arg Ile Arg Tyr Cys Ile Phe
                165                 170                 175

Gln Thr Thr Val Lys Ala Phe Leu Lys Cys Leu Lys Asp Asn Asp Asp
            180                 185                 190

Ser Ile Ser Phe Met Lys Ile Ser Ile Lys Thr Val Leu Glu Ser Tyr
        195                 200                 205

Ser Lys Leu Lys Ile Thr Ser Val Gly Val Val Met Ile Met Gly Ala
    210                 215                 220

Leu Thr Gln Ala Ala Leu Gln Leu Leu Ser Arg Gln Pro Ala Leu His
225                 230                 235                 240

Ser Val Leu Lys Glu Asn Ser Ala Glu Lys Tyr Cys Glu Tyr Leu Gly
                245                 250                 255

Lys Glu Val Phe Leu Gly Lys Asn Pro Pro Ser Ser Phe Cys Leu Glu
            260                 265                 270
```

```
Ile Gly Leu Lys Pro Phe Leu Lys Glu Phe Val Ser Gln Glu Leu Phe
            275                 280                 285

Ile Lys Phe Phe Ile Pro Asn Ile Glu Lys Ala Val Leu Arg Ser Pro
    290                 295                 300

Glu Val Gly Phe Ser Ile Leu Ser Glu Leu Tyr Ala Gly Val Ser Pro
305                 310                 315                 320

Glu Lys Val Asn Leu Leu Asn Ala Phe Ala Ser Ser Lys Leu Ile Asn
                325                 330                 335

Gln Tyr Phe Ser Ser Phe Lys Ser Ser Lys Glu Val Val Arg Ser Val
            340                 345                 350

Ser Leu Gln Ser Met Ile Ile Leu Leu Arg Lys Ile Ser Asn Thr Asp
        355                 360                 365

Thr Thr Leu Glu Asp Leu Thr Lys Leu Ile Asp Glu Ile Phe Lys Asn
    370                 375                 380

Ile Lys Ser Asn Leu Asn Ala Asp Tyr Lys Ser Leu Ile Ser Lys Ile
385                 390                 395                 400

Leu Ile Glu Ile Pro Leu Thr His Tyr Glu Val Ser Glu Lys Ile Cys
                405                 410                 415

Lys Gly Leu Ser Pro Tyr Ile Gly Lys Glu Gly Asn Glu Ala Ala Leu
            420                 425                 430

Thr Leu Met Leu Asn Ala Phe Phe Val His Tyr Phe Ser Leu Gly Lys
        435                 440                 445

Pro Ile Glu Asp Leu Asp Lys Ile Ile Ser Ala Gly Phe Ala Asp Lys
    450                 455                 460

Lys Pro Ala Leu Lys Lys Cys Trp Phe Ala Phe Leu Asn Asn Ser
465                 470                 475                 480

Asn Ala Ala Ser Glu Glu Val Ile Leu Asn Phe Ile Asp Gly Cys Leu
                485                 490                 495

Glu Phe Val Lys Asp Ser Ile Ile His Tyr Gln Thr His Gly His Ala
            500                 505                 510

Cys Ile Leu Ala Ser Ile Glu Phe Thr Asn Lys Ile Leu Ala Leu Asp
        515                 520                 525

Asn Thr Glu Leu Asn Asp Arg Val Met Gln Leu Ile Glu Thr Leu Pro
    530                 535                 540

Glu Asn Ser Ser Ile Gly Asp Ala Ile Leu Thr Ala Ala Leu Ser Thr
545                 550                 555                 560

Glu Leu Ser Ile Glu Asn Arg Ile His Ala Val Asn Leu Leu Gln Glu
                565                 570                 575

Leu Phe Tyr Lys Lys Pro Glu Phe Ile Gly Phe Ser Val Ile Asp Ala
            580                 585                 590

Ile Glu Arg Arg Met Arg Val Gln Glu Leu Ile Pro Gln Gln Asn Thr
        595                 600                 605

Ser Phe Lys Tyr Val Thr Ser Val Leu Leu Ala Ile Thr Ser Glu Leu
    610                 615                 620

Pro Asp Lys Glu Ala Ser Ile Lys Val Leu Ile Asn Ala Leu Val Ile
625                 630                 635                 640

Ala Gln Trp Asn Ile Phe Asn Ile Lys Asn Gly Trp Ala Gly Leu Val
                645                 650                 655

Leu Arg Ala Arg Leu Asp Pro Ala Glu Val Val Lys Glu His Ala Ser
            660                 665                 670

Val Ile Met Glu Lys Ile Leu Glu Ile Thr Gly Ser Cys Glu Trp Ile
        675                 680                 685

Asp Thr Ile Tyr Gly Ala Cys Gly Leu Gln Ala Ala Ala Tyr Ala Ala
```

```
                    690               695               700
        Phe Ile Gln Pro Asn Glu Phe Thr Pro Ile Leu Cys Lys Thr Ile Glu
        705               710               715               720

Ala Asp Leu Thr Ala Asp Asp Phe Ser Arg Leu Ser Glu Glu Asp Phe
                        725               730               735

Glu Ile Phe Ala Gly Glu Gly Val Leu Val Val Asp Val Leu Glu
                    740               745               750

Glu Ser Met Asn Lys Lys Leu Ser Asn Lys Asn Ser Lys Glu Tyr Glu
                    755               760               765

Thr Leu Met Trp Glu Gln Lys Ile Arg Lys Glu Gln Ala Lys Lys Asn
                    770               775               780

Val Lys Lys Leu Ser Lys Glu Glu Gln Glu Leu Val Asn Glu Gln Leu
        785               790               795               800

Ala Lys Glu Ser Ala Val Arg Ser His Val Ser Glu Ile Ser Thr Arg
                        805               810               815

Leu Lys Arg Gly Ile Arg Leu Val Ser Glu Leu Ser Lys Ala Ala Cys
                    820               825               830

Leu Val Gln Asn Gly Ile Ala Thr Trp Phe Pro Leu Ala Val Thr Lys
                    835               840               845

Leu Leu Tyr Leu Cys Ser Glu Pro Asn Ile Ser Lys Leu Thr Glu Asp
        850               855               860

Val Asn Asn Val Phe Leu Gln Leu Ser Gln Asn Val Ser Glu Arg Leu
        865               870               875               880

Gly Asn Ile Arg Leu Phe Leu Gly Leu Ala Thr Leu Arg Val His Asn
                        885               890               895

Ala Asn Gly Ile Ser Gln Asp Tyr Leu Gln Glu Pro Leu Val Glu Leu
                    900               905               910

Leu Thr Arg Val Leu Phe Arg Ile Lys Phe Val Ser Asn Gln Ala Ala
                    915               920               925

Ile Asp Ser Ile Ser Leu Thr Tyr Ile Leu Pro Leu Leu Ile Asn Val
                    930               935               940

Leu Glu Lys Gly Lys Ala Ile Ala Leu Lys Asn Ala Asp Lys Pro Val
        945               950               955               960

Val Lys Ala Glu Phe Val Glu Glu Asp Glu Glu Glu His Leu Leu
                        965               970               975

Leu Ala Met Glu Ile Ile Ser Val His Ala Gly Ala Phe Glu Asp Pro
                    980               985               990

Ser Ile Pro Arg Ile Ser Ile Val Glu Val Leu Leu Ser Leu Leu Ser
                    995               1000              1005

Leu Pro Ser Lys Ala Lys Ile Ala Lys Asp Cys Phe Asn Ala Leu
        1010              1015              1020

Cys Gln Ser Ile Ser Val Ala Pro Asn Gln Glu Asp Leu Asp Met
        1025              1030              1035

Ile Leu Ser Asn Leu Leu Ser Pro Asn Gln Phe Val Arg Ser Thr
        1040              1045              1050

Ile Leu Glu Thr Leu Asp Asn Glu Phe Glu Leu Glu Pro Phe Met
        1055              1060              1065

Lys Tyr Ser Pro Glu Val Phe Ile Cys Arg Phe Asp Ser Asp Pro
        1070              1075              1080

Ser Asn Arg Glu Ile Ala Asp Phe Ile Trp Glu Phe Asn Lys Phe
        1085              1090              1095

Val Val Asn Asp Glu Leu Leu Lys Ser Leu Phe Pro Leu Phe Asn
        1100              1105              1110
```

```
Gln Asp Asp Ser Gly Leu Arg Leu Phe Ala Ala Asn Ala Tyr Ala
    1115            1120                1125

Phe Gly Ala Val Ser Leu Phe Thr Ser Glu Glu Asn Ser Ser Lys
    1130            1135                1140

Asp Tyr Leu Asn Asp Leu Leu Asn Phe Tyr Lys Glu Lys Ala Lys
    1145            1150                1155

Pro Leu Glu Pro Ile Leu Asp Gln Phe Gly Leu Val Leu Val Ser
    1160            1165                1170

Ala Ser Glu Gln Lys Asp Pro Trp Gln Gly Arg Ser Thr Val Ala
    1175            1180                1185

Ile Thr Leu Lys Ile Met Ala Lys Ala Phe Ser Ala Glu Asp Asp
    1190            1195                1200

Thr Val Val Asn Ile Ile Lys Phe Leu Val Asp Asp Gly Gly Leu
    1205            1210                1215

Val Asp Arg Glu Pro Ile Val Arg Gln Glu Met Lys Glu Ala Gly
    1220            1225                1230

Val Glu Leu Ile Thr Leu His Gly Ser Gln Asn Ser Lys Asp Leu
    1235            1240                1245

Ile Pro Ile Phe Glu Glu Ala Leu Ser Ser Thr Asp Ser Ala
    1250            1255                1260

Leu Lys Glu Asn Val Ile Ile Leu Tyr Gly Thr Leu Ala Arg His
    1265            1270                1275

Leu Gln Gln Ser Asp Ala Arg Ile His Thr Ile Ile Glu Arg Leu
    1280            1285                1290

Leu Ser Thr Leu Asp Thr Pro Ser Ala Asp Ile Gln Gln Ala Val
    1295            1300                1305

Ser Ala Cys Ile Ala Pro Leu Val Phe Gln Phe Lys Gln Lys Val
    1310            1315                1320

Gly Asp Tyr Leu Gly Ile Leu Met Glu Lys Leu Leu Asn Pro Thr
    1325            1330                1335

Val Ala Ser Ser Met Arg Lys Gly Ala Ala Trp Gly Ile Ala Gly
    1340            1345                1350

Leu Val Lys Gly Tyr Gly Ile Ser Ala Leu Ser Glu Phe Asp Ile
    1355            1360                1365

Ile Arg Asn Leu Ile Glu Ala Ala Glu Asp Lys Lys Glu Pro Lys
    1370            1375                1380

Arg Arg Glu Ser Val Gly Phe Cys Phe Gln Tyr Leu Ser Glu Ser
    1385            1390                1395

Leu Gly Lys Phe Phe Glu Pro Tyr Val Ile Glu Ile Leu Pro Asn
    1400            1405                1410

Ile Leu Lys Asn Leu Gly Asp Ala Val Pro Glu Val Arg Asp Ala
    1415            1420                1425

Thr Ala Arg Ala Thr Lys Ala Ile Met Ala His Thr Thr Gly Tyr
    1430            1435                1440

Gly Val Lys Lys Leu Ile Pro Val Ala Val Ser Asn Leu Asp Glu
    1445            1450                1455

Ile Ala Trp Arg Thr Lys Arg Gly Ser Val Gln Leu Leu Gly Asn
    1460            1465                1470

Met Ala Tyr Leu Asp Pro Thr Gln Leu Ser Ala Ser Leu Ser Thr
    1475            1480                1485

Ile Val Pro Glu Ile Val Gly Val Leu Asn Asp Ser His Lys Glu
    1490            1495                1500
```

```
Val Arg Lys Ala Ala Asp Glu Ser Leu Lys Arg Phe Gly Glu Val
1505                1510                1515

Ile Arg Asn Pro Glu Ile Gln Lys Leu Val Pro Val Leu Leu Gln
1520                1525                1530

Ala Ile Gly Asp Pro Thr Lys Tyr Thr Glu Ala Leu Asp Ser
1535                1540                1545

Leu Ile Gln Thr Gln Phe Val His Tyr Ile Asp Gly Pro Ser Leu
1550                1555                1560

Ala Leu Ile Ile His Ile Ile His Arg Gly Met His Asp Arg Ser
1565                1570                1575

Ala Asn Ile Lys Arg Lys Ala Cys Lys Ile Val Gly Asn Met Ala
1580                1585                1590

Ile Leu Val Asp Thr Lys Asp Leu Ile Pro Tyr Leu Gln Gln Leu
1595                1600                1605

Ile Asp Glu Val Glu Ile Ala Met Val Asp Pro Val Pro Asn Thr
1610                1615                1620

Arg Ala Thr Ala Ala Arg Ala Leu Gly Ala Leu Val Glu Arg Leu
1625                1630                1635

Gly Glu Glu Gln Phe Pro Asp Leu Ile Pro Arg Leu Leu Asp Thr
1640                1645                1650

Leu Ser Asp Glu Ser Lys Ser Gly Asp Arg Leu Gly Ser Ala Gln
1655                1660                1665

Ala Leu Ala Glu Val Ile Ser Gly Leu Gly Leu Thr Lys Leu Asp
1670                1675                1680

Glu Met Leu Pro Thr Ile Leu Ala Gly Val Thr Asn Phe Arg Ala
1685                1690                1695

Tyr Ile Arg Glu Gly Phe Met Pro Leu Leu Phe Leu Pro Val
1700                1705                1710

Cys Phe Gly Ser Gln Phe Ala Pro Tyr Ile Asn Gln Ile Ile Gln
1715                1720                1725

Pro Ile Leu Ser Gly Leu Ala Asp Asn Asp Glu Asn Ile Arg Asp
1730                1735                1740

Thr Ala Leu Lys Ala Gly Lys Leu Ile Val Lys Asn Tyr Ala Thr
1745                1750                1755

Lys Ala Val Asp Leu Leu Leu Pro Glu Leu Glu Arg Gly Met Phe
1760                1765                1770

Asp Glu Asn Asp Arg Ile Arg Leu Ser Ser Val Gln Leu Thr Gly
1775                1780                1785

Glu Leu Leu Phe Gln Val Thr Gly Ile Ser Ser Arg Asn Glu Phe
1790                1795                1800

Ser Glu Glu Asp Gly Asp His Asn Gly Glu Phe Ser Gly Lys Leu
1805                1810                1815

Val Asp Val Leu Gly Gln Asp Arg Arg Asp Arg Ile Leu Ala Ala
1820                1825                1830

Leu Phe Val Cys Arg Asn Asp Thr Ser Gly Ile Val Arg Ala Thr
1835                1840                1845

Thr Val Asp Ile Trp Lys Ala Leu Val Pro Asn Thr Pro Arg Ala
1850                1855                1860

Val Lys Glu Ile Leu Pro Thr Leu Thr Gly Met Ile Val Thr His
1865                1870                1875

Leu Ala Ser Ser Ser Asn Val Leu Arg Asn Ile Ala Ala Gln Thr
1880                1885                1890

Leu Gly Asp Leu Val Arg Arg Val Gly Gly Asn Ala Leu Ser Gln
```

```
                1895                1900                1905
Leu Leu Pro Ser Leu Glu Glu Ser Leu Ile Glu Thr Ser Asn Ser
        1910                1915                1920

Asp Ser Arg Gln Gly Val Cys Ile Ala Leu Tyr Glu Leu Ile Glu
        1925                1930                1935

Ser Ala Ser Thr Glu Thr Ile Ser Gln Phe Gln Ser Thr Ile Val
        1940                1945                1950

Asn Ile Ile Arg Thr Ala Leu Ile Asp Glu Ser Ala Thr Val Arg
        1955                1960                1965

Glu Ala Ala Ala Leu Ser Phe Asp Val Phe Gln Asp Val Val Gly
        1970                1975                1980

Lys Thr Ala Val Asp Glu Val Leu Pro Tyr Leu Leu His Met Leu
        1985                1990                1995

Glu Ser Ser Asp Asn Ser Asp Phe Ala Leu Leu Gly Leu Gln Glu
        2000                2005                2010

Ile Met Ser Lys Lys Ser Asp Val Ile Phe Pro Ile Leu Ile Pro
        2015                2020                2025

Thr Leu Leu Ala Pro Pro Ile Asp Ala Phe Arg Ala Ser Ala Leu
        2030                2035                2040

Gly Ser Leu Ala Glu Val Ala Gly Ser Ala Leu Tyr Lys Arg Leu
        2045                2050                2055

Ser Ile Ile Ile Asn Ala Leu Val Asp Ala Ile Ile Gly Thr Ser
        2060                2065                2070

Glu Asp Glu Ser Thr Lys Gly Ala Leu Glu Leu Ala Leu Asp Arg
        2075                2080                2085

Val Phe Leu Ser Val Asn Asp Asp Glu Gly Leu His Pro Leu Leu
        2090                2095                2100

Gln Gln Ile Met Ser Leu Leu Lys Ser Asp Asn Ile Glu Lys Arg
        2105                2110                2115

Ile Ala Val Leu Glu Arg Leu Pro Asn Phe Phe Asp Lys Thr Val
        2120                2125                2130

Leu Asp Phe Asp Val Tyr Ile Pro Asn Phe Val Ser His Ala Ile
        2135                2140                2145

Leu Ser Leu Asp Asp Glu Asp Gln Arg Val Val Asn Gly Asn Phe
        2150                2155                2160

Asn Ala Leu Ser Thr Leu Leu Lys Lys Val Asp Lys Pro Thr Leu
        2165                2170                2175

Glu Lys Leu Val Lys Pro Ala Lys Gln Ser Leu Ala Leu Thr Gly
        2180                2185                2190

Arg Gln Gly Gln Asp Val Ala Ala Phe Lys Leu Pro Arg Gly Pro
        2195                2200                2205

Asn Cys Val Leu Pro Ile Phe Leu His Gly Leu Met Tyr Gly Ser
        2210                2215                2220

Asn Asp Glu Arg Glu Glu Ser Ala Leu Ala Ile Ala Asp Val Val
        2225                2230                2235

Ser Lys Thr Pro Ala Ala Asn Leu Lys Pro Phe Val Ser Val Ile
        2240                2245                2250

Thr Gly Pro Leu Ile Arg Val Val Gly Glu Arg Phe Ser Ser Asp
        2255                2260                2265

Ile Lys Ala Ala Ile Leu Phe Ala Leu Asn Val Leu Phe Ile Lys
        2270                2275                2280

Ile Pro Met Phe Leu Arg Pro Phe Ile Pro Gln Leu Gln Arg Thr
        2285                2290                2295
```

```
Phe Val Lys Ser Leu Ser Asp Ala Thr Asn Glu Thr Leu Arg Leu
    2300            2305                2310

Arg Ala Ala Lys Ala Leu Gly Ala Leu Ile Glu His Gln Pro Arg
    2315            2320                2325

Val Asp Pro Leu Val Ile Glu Leu Val Thr Gly Ala Lys Gln Ala
    2330            2335                2340

Thr Asp Glu Gly Val Lys Thr Ala Met Leu Lys Ala Leu Leu Glu
    2345            2350                2355

Val Ile Met Lys Ala Gly Ser Lys Leu Asn Glu Asn Ser Lys Thr
    2360            2365                2370

Asn Ile Val Asn Leu Val Glu Glu Met Leu Gly Ser Asn Asp
    2375            2380                2385

Lys Leu Ala Val Ala Tyr Ala Lys Leu Ile Gly Ser Leu Ser Glu
    2390            2395                2400

Ile Leu Ser Asn Asp Glu Ala His Lys Ile Leu Gln Asp Lys Val
    2405            2410                2415

Leu Asn Ala Asp Leu Asp Gly Glu Thr Gly Lys Phe Ala Ile Leu
    2420            2425                2430

Thr Leu Asn Ser Phe Leu Lys Asp Ala Pro Thr His Ile Phe Asn
    2435            2440                2445

Thr Gly Leu Ile Asp Glu Phe Val Ser Tyr Ile Leu Asn Ala Ile
    2450            2455                2460

Arg Ser Pro Asp Val Tyr Phe Gly Glu Asn Gly Thr Ile Ala Ala
    2465            2470                2475

Gly Lys Leu Leu Leu Leu Gly Glu Lys Arg Ser Pro Phe Val
    2480            2485                2490

Lys Lys Asp Ala Ala Glu Pro Phe Lys Ile Gly Asp Glu Asn Ile
    2495            2500                2505

Asn Leu Leu Ile Asn Glu Leu Ser Lys Ala Val Leu Gln Pro Ala
    2510            2515                2520

Ser Asn Ser Thr Asp Val Arg Arg Leu Ala Leu Val Val Ile Arg
    2525            2530                2535

Thr Leu Ala Arg Phe Lys Phe Asp Glu Cys Ile Lys Gln Tyr Phe
    2540            2545                2550

Asp Val Val Gly Pro Ser Val Phe Ser Cys Leu Arg Asp Pro Val
    2555            2560                2565

Ile Pro Ile Lys Leu Ala Ala Glu Lys Ala Tyr Leu Ala Leu Phe
    2570            2575                2580

Lys Leu Val Glu Glu Asp Asp Met His Thr Phe Asn Glu Trp Phe
    2585            2590                2595

Ala Lys Ile Ser Asp Arg Gly Asn Ser Ile Glu Thr Val Thr Gly
    2600            2605                2610

Thr Thr Ile Gln Leu Arg Ser Val Gly Asp Tyr Thr Lys Arg Val
    2615            2620                2625

Gly Lys Arg Leu Ala Asn Val Glu Arg Glu Arg Ile Ala Ala Gly
    2630            2635                2640

Gly Asp Ala Glu Thr Met Phe Ser Asp Arg Phe Glu Asp Glu Arg
    2645            2650                2655

Glu Ile Trp Ala Val Gly Gly Val Glu Leu Thr Thr Asp Ile
    2660            2665                2670

<210> SEQ ID NO 51
<211> LENGTH: 4980
```

<212> TYPE: DNA
<213> ORGANISM: Saccharomyces cerevisiae

<400> SEQUENCE: 51

| | | | | | |
|---|---|---|---|---|---|
| atgtcattga | gtcatctcac | tttagatcaa | tattatgaaa | tacagtgcaa | cgaacttgaa | 60 |
| gcgatacgtt | ccatttatat | ggatgacttt | actgacttaa | ctaaaagaaa | gtctagctgg | 120 |
| gataagcagc | cacagattat | attcgaaatt | acgcttcgat | ctgttgacaa | agagccggtt | 180 |
| gaatcttcta | taacattaca | ttttgcgatg | accccaatgt | atccttatac | cgctccagaa | 240 |
| atagaattca | aaatgtaca | aaatgtaatg | gatagtcaat | tgcaaatgct | gaaaagtgaa | 300 |
| tttaagaaaa | tccacaacac | ctcccgaggc | caagagatta | tatttgaaat | tacatctttt | 360 |
| actcaagaaa | aactggacga | atttcaaaat | gtggtaaata | cacagtcctt | ggaagatgat | 420 |
| cgattacaaa | gaatcaaaga | aactaaagaa | caattagaaa | aggaagaaag | agaaaaacaa | 480 |
| caggaaacaa | taaaaaaag | atcagatgag | cagcgaagga | tagatgaaat | tgttcaaaga | 540 |
| gagttggaga | aaagacaaga | tgatgatgat | gatttgctat | tcaacagaac | aacccagtta | 600 |
| gatttacaac | caccttcaga | atgggttgca | tcaggtgaag | ctattgtctt | ttcaaaaact | 660 |
| ataaaggcaa | aattgcctaa | taactcaatg | ttcaagttta | aagcagttgt | aaatcctaag | 720 |
| ccaataaaac | tgacatcaga | tatatttagt | ttttccaaac | aatttcttgt | gaagccttat | 780 |
| ataccaccag | aatctccgtt | ggcagatttt | ttaatgtctt | ctgaaatgat | ggaaaatttc | 840 |
| tactatttgc | tatctgaaat | tgaattggat | aatagctatt | tcaacacaag | taatggaaaa | 900 |
| aaagaaatag | caaatttaga | gaaagagtta | gagacggtgt | tgaaagctaa | gcatgacaat | 960 |
| gtgaatcgat | tgttcggtta | tacggtggag | cgcatgggga | gaaataatgc | aacgtttgtt | 1020 |
| tggaaaataa | gactcttgac | agagtactgt | aactactatc | cattgggaga | tttgatacaa | 1080 |
| tctgttggat | ttgttaactt | agcaacagcg | cgtatttgga | tgattagatt | gcttgaagga | 1140 |
| ttggaggcca | tacacaaatt | gggaattgtt | cataaatgta | tcaacttaga | aaccgtgatc | 1200 |
| ctggtgaagg | atgcagattt | tggaagcact | attcccaagt | tagttcactc | cacttatggc | 1260 |
| tacactgttt | tgaatatgct | atcgagatat | ccaaataaaa | atggttcttc | ggttgagtta | 1320 |
| tctccaagta | catggatagc | ccctgagttg | ttgaaattca | ataacgccaa | acctcaaaga | 1380 |
| ttaactgata | tttggcaact | tggtgttttg | tttatccaga | taatcagtgg | atctgatata | 1440 |
| gtgatgaatt | ttgaaacgcc | tcaagaattc | ctagattcaa | caagtatgga | tgaaacttta | 1500 |
| tatgatcttc | tttcgaaaat | gcttaataac | gatccgaaga | aaagattagg | aacattagaa | 1560 |
| ctactgccca | tgaaattctt | aaggaccaat | attgactcta | caatcaatcg | atttaactta | 1620 |
| gtttccgaaa | gtgtcaattc | taattccttg | gagttaactc | ctggagatac | cataaccgtt | 1680 |
| cggggcaatg | gaggtagaac | actttcacaa | tcgagtatac | gaagaagatc | atttaatgtt | 1740 |
| ggttccagat | tctcttctat | aaatcctgca | acgcgatcac | gatatgcttc | tgactttgaa | 1800 |
| gagattgcag | ttttaggcca | gggcgcattt | ggacaagttg | tcaaggcacg | taatgctctc | 1860 |
| gatagcagat | actatgcgat | caagaagatt | agacatacag | aagaaaagtt | atctactata | 1920 |
| ttgagtgaag | taatgctgtt | agcaagctta | aatcatcaat | atgttgtgcg | ttactatgct | 1980 |
| gcatggttag | aagaagacag | tatggatgaa | acgttttttg | aatcaactga | tgaagaaagt | 2040 |
| gacttgagcg | aatcttcctc | tgattttgag | gaaaatgatt | tattagatca | aagcagtatt | 2100 |
| tttaaaaata | gaacaaatca | cgatttggat | aatagtaact | gggatttcat | atcggggtca | 2160 |
| ggatatccgg | atattgtctt | tgaaaatagt | tctcgtgatg | atgaaaatga | agatctagac | 2220 |

```
catgatactt cctcgacttc ctcgagcgaa agtcaagatg atactgataa agaatcaaag    2280
agtatccaga acgttccaag aaggaggaat tttgtaaaac cgatgactgc tgttaagaag    2340
aaaagtacgc ttttattca aatggagtac tgtgaaaata gaacgctata tgatttgatc    2400
cattctgaaa atttaaatca acaacgtgat gaatattgga ggttatttcg acaaattttg    2460
gaagcactga gttatataca ttcccagggt atcattcata gggatctgaa gccaatgaat    2520 attttatag atgaatcgag aaatgttaaa atcggtgatt ttgggttagc taagaacgtc    2580
catagatctc tggatatact taagctagat tcacagaatt tgccaggcag ctcagataat    2640
ttaacatccg ccattggtac agcaatgtat gttgctactg aagttttaga tggtacaggt    2700
cactataatg aaaagattga tatgtattca cttggaatca ttttttttga aatgatctat    2760
cctttcagta caggtatgga gagagttaat attttgaaaa agttacgatc agtgtcgata    2820
gaatttcctc ctgatttcga cgataataag atgaaagttg aaagaaaat tataaggtta    2880 ctcatagacc atgatcccaa taaaaggcct ggtgctagga cattattaaa tagtggttgg    2940
cttcctgtga agcatcagga tgaagtaatc aaagaggctt taaaaagttt gtcgaatcct    3000
tcatccccct ggcaacagca agttcgagaa agtttattta accaatctta cagtctaaca    3060
aatgatattc tatttgataa ctcagttcca acatccactc ctttcgcaaa cattctcagg    3120
tcccaaatga cagaagaggt agttaaaatt ttcaggaaac atggaggaat tgaaaataat    3180
gctcctccga ggattttcc aaaggccccc atatacggta cgcagaatgt atatgaagtg    3240
cttgacaagg gcggtaccgt cttgcagtta caatatgatt taacttatcc tatggctagg    3300
tatctatcta aaaatccaag tctgatttct aagcaatata ggatgcagca cgtttaccga    3360
cctcctgatc attcaaggtc aagtttggaa cctagaaagt ttggtgagat tgacttcgac    3420
ataatttcaa aatcttcctc agagtcagga ttttatgatg cagaaagctt gaaaattatc    3480
gatgaaatat taaccgtatt tcctgtattt gagaaaacaa acactttttt catattaaat    3540
catgctgata ttttggagag tgtttttcaac tttacaaata ttgataaagc ccaaaggcct    3600
ctagtttcac gaatgttgtc gcaagtaggc tttgcaaggt ccttcaagga agtaaagaat    3660
gaactaaagg cgcaactgaa catatcttct acggcattga atgatttgga gttatttgat    3720
tttagactgg acttcgaagc agccaaaaaa cgcctgtata aattgatgat tgatagtccg    3780
catctaaaaa aaattgagga ctcttttgtcc catatatcaa aggttctcag ttacctaaaa    3840 ccccttagaag ttgcaagaaa tgttgtgata tctcctttga gtaactacaa tagcgctttt    3900
tacaaaggag gtatcatgtt tcatgcagtt tatgacgatg gatcctcacg taatatgata    3960
gctgctggag ggaggtatga cactttgata tccttttttg ccagaccatc aggaaaaaag    4020
agcagcaata ctcgtaaggc tgtaggtttc aacttagcgt gggaaacaat attcggtata    4080
gcccaaaact atttcaaact cgcttctgga aataggataa agaagagaaa taggttttg    4140 aaagatacag ctgttgattg gaagccaagc aggtgtgatg tattgatatc gagttttcg    4200 aactctttgt tggacacaat cggggttaca atactgaata cattgtggaa gcaaaacatt    4260
aaagcggata tgttaaggga ttgttcctcg gtggatgatg tcgttactgg cgctcaacag    4320
gatggtatag actggatttt gctgattaag caacaagcgt atccactaac caatcacaag    4380
agaaagtaca agccattaaa aataaaaaaa ttgagcacta atgttgacat agatttagat    4440
cttgatgagt ttttaacctt gtaccaacaa gaaactggta taaatctttt gatcaacgat    4500
agtctcactt tgggcgataa ggctgatgaa ttttaaagat gggatgaaaa cagcagtgcc    4560
ggtagtagtc aagaaggtga catagatgat gttgttgctg gttcgactaa taatcaaaag    4620
```

```
gtaatttatg ttccaaacat ggctacaaga tctaagaaag ctaataaaag ggaaaagtgg    4680
gtttatgagg atgcagccag aaattcttcg aatatgatat tacacaattt atccaatgca    4740
ccaattatca ctgttgatgc cttaagagat gaaactttag aaataatctc aattacttct    4800
ttggctcaga aggaagaatg gctgagaaaa gtttttgggt caggtaataa ctcgactcct    4860
agaagctttg ccacgagcat ttataataac ctctccaaag aggctcataa agggaatagg    4920
tgggcaatat tatactgcca caaaaccgga aaatcatctg ttatcgattt acagaggtag    4980
```

<210> SEQ ID NO 52
<211> LENGTH: 1659
<212> TYPE: PRT
<213> ORGANISM: Saccharomyces cerevisiae

<400> SEQUENCE: 52

```
Met Ser Leu Ser His Leu Thr Leu Asp Gln Tyr Tyr Glu Ile Gln Cys
1               5                   10                  15

Asn Glu Leu Glu Ala Ile Arg Ser Ile Tyr Met Asp Asp Phe Thr Asp
            20                  25                  30

Leu Thr Lys Arg Lys Ser Ser Trp Asp Lys Gln Pro Gln Ile Ile Phe
        35                  40                  45

Glu Ile Thr Leu Arg Ser Val Asp Lys Glu Pro Val Glu Ser Ser Ile
    50                  55                  60

Thr Leu His Phe Ala Met Thr Pro Met Tyr Pro Tyr Thr Ala Pro Glu
65                  70                  75                  80

Ile Glu Phe Lys Asn Val Gln Asn Val Met Asp Ser Gln Leu Gln Met
                85                  90                  95

Leu Lys Ser Glu Phe Lys Lys Ile His Asn Thr Ser Arg Gly Gln Glu
            100                 105                 110

Ile Ile Phe Glu Ile Thr Ser Phe Thr Gln Glu Lys Leu Asp Glu Phe
        115                 120                 125

Gln Asn Val Val Asn Thr Gln Ser Leu Glu Asp Asp Arg Leu Gln Arg
    130                 135                 140

Ile Lys Glu Thr Lys Glu Gln Leu Glu Lys Glu Glu Arg Glu Lys Gln
145                 150                 155                 160

Gln Glu Thr Ile Lys Lys Arg Ser Asp Glu Gln Arg Arg Ile Asp Glu
                165                 170                 175

Ile Val Gln Arg Glu Leu Glu Lys Arg Gln Asp Asp Asp Asp Leu
            180                 185                 190

Leu Phe Asn Arg Thr Thr Gln Leu Asp Leu Gln Pro Pro Ser Glu Trp
        195                 200                 205

Val Ala Ser Gly Glu Ala Ile Val Phe Ser Lys Thr Ile Lys Ala Lys
    210                 215                 220

Leu Pro Asn Asn Ser Met Phe Lys Phe Lys Ala Val Val Asn Pro Lys
225                 230                 235                 240

Pro Ile Lys Leu Thr Ser Asp Ile Phe Ser Phe Ser Lys Gln Phe Leu
                245                 250                 255

Val Lys Pro Tyr Ile Pro Pro Glu Ser Pro Leu Ala Asp Phe Leu Met
            260                 265                 270

Ser Ser Glu Met Met Glu Asn Phe Tyr Tyr Leu Leu Ser Glu Ile Glu
        275                 280                 285

Leu Asp Asn Ser Tyr Phe Asn Thr Ser Asn Gly Lys Lys Glu Ile Ala
    290                 295                 300

Asn Leu Glu Lys Glu Leu Glu Thr Val Leu Lys Ala Lys His Asp Asn
```

-continued

```
            305                 310                 315                 320
Val Asn Arg Leu Phe Gly Tyr Thr Val Glu Arg Met Gly Arg Asn Asn
                    325                 330                 335

Ala Thr Phe Val Trp Lys Ile Arg Leu Leu Thr Glu Tyr Cys Asn Tyr
                    340                 345                 350

Tyr Pro Leu Gly Asp Leu Ile Gln Ser Val Gly Phe Val Asn Leu Ala
                    355                 360                 365

Thr Ala Arg Ile Trp Met Ile Arg Leu Leu Glu Gly Leu Glu Ala Ile
                    370                 375                 380

His Lys Leu Gly Ile Val His Lys Cys Ile Asn Leu Glu Thr Val Ile
385                 390                 395                 400

Leu Val Lys Asp Ala Asp Phe Gly Ser Thr Ile Pro Lys Leu Val His
                    405                 410                 415

Ser Thr Tyr Gly Tyr Thr Val Leu Asn Met Leu Ser Arg Tyr Pro Asn
                    420                 425                 430

Lys Asn Gly Ser Ser Val Glu Leu Ser Pro Ser Thr Trp Ile Ala Pro
                    435                 440                 445

Glu Leu Leu Lys Phe Asn Asn Ala Lys Pro Gln Arg Leu Thr Asp Ile
                    450                 455                 460

Trp Gln Leu Gly Val Leu Phe Ile Gln Ile Ile Ser Gly Ser Asp Ile
465                 470                 475                 480

Val Met Asn Phe Glu Thr Pro Gln Glu Phe Leu Asp Ser Thr Ser Met
                    485                 490                 495

Asp Glu Thr Leu Tyr Asp Leu Leu Ser Lys Met Leu Asn Asn Asp Pro
                    500                 505                 510

Lys Lys Arg Leu Gly Thr Leu Glu Leu Leu Pro Met Lys Phe Leu Arg
                    515                 520                 525

Thr Asn Ile Asp Ser Thr Ile Asn Arg Phe Asn Leu Val Ser Glu Ser
                    530                 535                 540

Val Asn Ser Asn Ser Leu Glu Leu Thr Pro Gly Asp Thr Ile Thr Val
545                 550                 555                 560

Arg Gly Asn Gly Gly Arg Thr Leu Ser Gln Ser Ser Ile Arg Arg Arg
                    565                 570                 575

Ser Phe Asn Val Gly Ser Arg Phe Ser Ser Ile Asn Pro Ala Thr Arg
                    580                 585                 590

Ser Arg Tyr Ala Ser Asp Phe Glu Glu Ile Ala Val Leu Gly Gln Gly
                    595                 600                 605

Ala Phe Gly Gln Val Val Lys Ala Arg Asn Ala Leu Asp Ser Arg Tyr
                    610                 615                 620

Tyr Ala Ile Lys Lys Ile Arg His Thr Glu Glu Lys Leu Ser Thr Ile
625                 630                 635                 640

Leu Ser Glu Val Met Leu Leu Ala Ser Leu Asn His Gln Tyr Val Val
                    645                 650                 655

Arg Tyr Tyr Ala Ala Trp Leu Glu Glu Asp Ser Met Asp Glu Asn Val
                    660                 665                 670

Phe Glu Ser Thr Asp Glu Glu Ser Asp Leu Ser Glu Ser Ser Ser Asp
                    675                 680                 685

Phe Glu Glu Asn Asp Leu Leu Asp Gln Ser Ser Ile Phe Lys Asn Arg
                    690                 695                 700

Thr Asn His Asp Leu Asp Asn Ser Asn Trp Asp Phe Ile Ser Gly Ser
705                 710                 715                 720

Gly Tyr Pro Asp Ile Val Phe Glu Asn Ser Ser Arg Asp Asp Glu Asn
                    725                 730                 735
```

-continued

```
Glu Asp Leu Asp His Asp Thr Ser Ser Thr Ser Ser Glu Ser Gln
            740                 745                 750

Asp Asp Thr Asp Lys Glu Ser Lys Ser Ile Gln Asn Val Pro Arg Arg
            755                 760                 765

Arg Asn Phe Val Lys Pro Met Thr Ala Val Lys Lys Ser Thr Leu
            770                 775                 780

Phe Ile Gln Met Glu Tyr Cys Glu Asn Arg Thr Leu Tyr Asp Leu Ile
785                 790                 795                 800

His Ser Glu Asn Leu Asn Gln Gln Arg Asp Glu Tyr Trp Arg Leu Phe
                805                 810                 815

Arg Gln Ile Leu Glu Ala Leu Ser Tyr Ile His Ser Gln Gly Ile Ile
            820                 825                 830

His Arg Asp Leu Lys Pro Met Asn Ile Phe Ile Asp Glu Ser Arg Asn
            835                 840                 845

Val Lys Ile Gly Asp Phe Gly Leu Ala Lys Asn Val His Arg Ser Leu
850                 855                 860

Asp Ile Leu Lys Leu Asp Ser Gln Asn Leu Pro Gly Ser Ser Asp Asn
865                 870                 875                 880

Leu Thr Ser Ala Ile Gly Thr Ala Met Tyr Val Ala Thr Glu Val Leu
            885                 890                 895

Asp Gly Thr Gly His Tyr Asn Glu Lys Ile Asp Met Tyr Ser Leu Gly
            900                 905                 910

Ile Ile Phe Phe Glu Met Ile Tyr Pro Phe Ser Thr Gly Met Glu Arg
            915                 920                 925

Val Asn Ile Leu Lys Lys Leu Arg Ser Val Ser Ile Glu Phe Pro Pro
            930                 935                 940

Asp Phe Asp Asp Asn Lys Met Lys Val Glu Lys Lys Ile Ile Arg Leu
945                 950                 955                 960

Leu Ile Asp His Asp Pro Asn Lys Arg Pro Gly Ala Arg Thr Leu Leu
            965                 970                 975

Asn Ser Gly Trp Leu Pro Val Lys His Gln Asp Glu Val Ile Lys Glu
            980                 985                 990

Ala Leu Lys Ser Leu Ser Asn Pro  Ser Ser Pro Trp Gln  Gln Gln Val
            995                 1000                1005

Arg Glu  Ser Leu Phe Asn Gln  Ser Tyr Ser Leu Thr  Asn Asp Ile
    1010                1015                1020

Leu Phe  Asp Asn Ser Val Pro  Thr Ser Thr Pro Phe  Ala Asn Ile
    1025                1030                1035

Leu Arg  Ser Gln Met Thr Glu  Glu Val Val Lys Ile  Phe Arg Lys
    1040                1045                1050

His Gly  Gly Ile Glu Asn Asn  Ala Pro Pro Arg Ile  Phe Pro Lys
    1055                1060                1065

Ala Pro  Ile Tyr Gly Thr Gln  Asn Val Tyr Glu Val  Leu Asp Lys
    1070                1075                1080

Gly Gly  Thr Val Leu Gln Leu  Gln Tyr Asp Leu Thr  Tyr Pro Met
    1085                1090                1095

Ala Arg  Tyr Leu Ser Lys Asn  Pro Ser Leu Ile Ser  Lys Gln Tyr
    1100                1105                1110

Arg Met  Gln His Val Tyr Arg  Pro Pro Asp His Ser  Arg Ser Ser
    1115                1120                1125

Leu Glu  Pro Arg Lys Phe Gly  Glu Ile Asp Phe Asp  Ile Ile Ser
    1130                1135                1140
```

```
Lys Ser Ser Ser Glu Ser Gly Phe Tyr Asp Ala Glu Ser Leu Lys
    1145                1150                1155

Ile Ile Asp Glu Ile Leu Thr Val Phe Pro Val Phe Glu Lys Thr
1160                1165                1170

Asn Thr Phe Phe Ile Leu Asn His Ala Asp Ile Leu Glu Ser Val
    1175                1180                1185

Phe Asn Phe Thr Asn Ile Asp Lys Ala Gln Arg Pro Leu Val Ser
    1190                1195                1200

Arg Met Leu Ser Gln Val Gly Phe Ala Arg Ser Phe Lys Glu Val
    1205                1210                1215

Lys Asn Glu Leu Lys Ala Gln Leu Asn Ile Ser Ser Thr Ala Leu
    1220                1225                1230

Asn Asp Leu Glu Leu Phe Asp Phe Arg Leu Asp Phe Glu Ala Ala
    1235                1240                1245

Lys Lys Arg Leu Tyr Lys Leu Met Ile Asp Ser Pro His Leu Lys
    1250                1255                1260

Lys Ile Glu Asp Ser Leu Ser His Ile Ser Lys Val Leu Ser Tyr
    1265                1270                1275

Leu Lys Pro Leu Glu Val Ala Arg Asn Val Val Ile Ser Pro Leu
    1280                1285                1290

Ser Asn Tyr Asn Ser Ala Phe Tyr Lys Gly Gly Ile Met Phe His
    1295                1300                1305

Ala Val Tyr Asp Asp Gly Ser Ser Arg Asn Met Ile Ala Ala Gly
    1310                1315                1320

Gly Arg Tyr Asp Thr Leu Ile Ser Phe Phe Ala Arg Pro Ser Gly
    1325                1330                1335

Lys Lys Ser Ser Asn Thr Arg Lys Ala Val Gly Phe Asn Leu Ala
    1340                1345                1350

Trp Glu Thr Ile Phe Gly Ile Ala Gln Asn Tyr Phe Lys Leu Ala
    1355                1360                1365

Ser Gly Asn Arg Ile Lys Lys Arg Asn Arg Phe Leu Lys Asp Thr
    1370                1375                1380

Ala Val Asp Trp Lys Pro Ser Arg Cys Asp Val Leu Ile Ser Ser
    1385                1390                1395

Phe Ser Asn Ser Leu Leu Asp Thr Ile Gly Val Thr Ile Leu Asn
    1400                1405                1410

Thr Leu Trp Lys Gln Asn Ile Lys Ala Asp Met Leu Arg Asp Cys
    1415                1420                1425

Ser Ser Val Asp Asp Val Val Thr Gly Ala Gln Gln Asp Gly Ile
    1430                1435                1440

Asp Trp Ile Leu Leu Ile Lys Gln Gln Ala Tyr Pro Leu Thr Asn
    1445                1450                1455

His Lys Arg Lys Tyr Lys Pro Leu Lys Ile Lys Lys Leu Ser Thr
    1460                1465                1470

Asn Val Asp Ile Asp Leu Asp Leu Asp Glu Phe Leu Thr Leu Tyr
    1475                1480                1485

Gln Gln Glu Thr Gly Asn Lys Ser Leu Ile Asn Asp Ser Leu Thr
    1490                1495                1500

Leu Gly Asp Lys Ala Asp Glu Phe Lys Arg Trp Asp Glu Asn Ser
    1505                1510                1515

Ser Ala Gly Ser Ser Gln Glu Gly Asp Ile Asp Asp Val Val Ala
    1520                1525                1530

Gly Ser Thr Asn Asn Gln Lys Val Ile Tyr Val Pro Asn Met Ala
```

Thr Arg Ser Lys Lys Ala Asn Lys Arg Glu Lys Trp Val Tyr Glu
             1550            1555            1560

Asp Ala Ala Arg Asn Ser Ser Asn Met Ile Leu His Asn Leu Ser
    1565            1570            1575

Asn Ala Pro Ile Ile Thr Val Asp Ala Leu Arg Asp Glu Thr Leu
    1580            1585            1590

Glu Ile Ile Ser Ile Thr Ser Leu Ala Gln Lys Glu Glu Trp Leu
    1595            1600            1605

Arg Lys Val Phe Gly Ser Gly Asn Asn Ser Thr Pro Arg Ser Phe
    1610            1615            1620

Ala Thr Ser Ile Tyr Asn Asn Leu Ser Lys Glu Ala His Lys Gly
    1625            1630            1635

Asn Arg Trp Ala Ile Leu Tyr Cys His Lys Thr Gly Lys Ser Ser
    1640            1645            1650

Val Ile Asp Leu Gln Arg
    1655

<210> SEQ ID NO 53
<211> LENGTH: 918
<212> TYPE: DNA
<213> ORGANISM: Saccharomyces cerevisiae

<400> SEQUENCE: 53
atgtcggagt ttaatattac agaaacttat ctaaggtttt tagaagaaga tactgagatg      60
acaatgccga ttgctgccat tgaagcattg gtcacgctat taagaataaa acaccagaa     120
acagcggcag aaatgattaa tacaataaaa agctccacgg aagaacttat taaatccatt     180
ccgaactcag tttccctgag agccggttgt gatattttca tgagatttgt cttaagaaat     240
cttcatttat acggtgattg ggaaaactgt aaacaacatt tgattgaaaa tggccagctt     300
tttgtatcga gagccaaaaa atcgcgtaac aagattgcag aaatagggggt ggatttcata     360
gctgatgatg atatcatctt ggtacatggt tattcgagag cagtatttc tttattaaat     420
catgcagcaa ataagtttat taggttcaga tgtgtggtga cagaatcaag acctagcaaa     480
caagggaacc agctatatac tttacttgaa caaaagggca tacccgtgac tcttattgtc     540
gatagcgcgg ttggagcggt aatcgataag gttgacaaag tgttcgttgg tgctgagggt     600
gttgctgaat caggtggtat tataaatctc gtgggtacct attcagtggg tgttttagca     660
cataatgcaa gaaaaccatt ctatgtggtc actgaaagtc acaaatttgt tcgtatgttt     720
ccattgtctt cagatgatct acctatggcc ggccctcctt tggatttcac acgtcgtacg     780
gacgatctag aagatgcatt gcgtgggccc acgatcgact ataccgccca gaaatacatt     840
actgcattga ttacagattt agggggtcctc actccaagtg ccgtttcaga agagttaatc     900
aagatgtggt atgattaa                                                    918

<210> SEQ ID NO 54
<211> LENGTH: 305
<212> TYPE: PRT
<213> ORGANISM: Saccharomyces cerevisiae

<400> SEQUENCE: 54

Met Ser Glu Phe Asn Ile Thr Glu Thr Tyr Leu Arg Phe Leu Glu Glu
1               5                   10                  15

Asp Thr Glu Met Thr Met Pro Ile Ala Ala Ile Glu Ala Leu Val Thr
            20                  25                  30

```
Leu Leu Arg Ile Lys Thr Pro Glu Thr Ala Ala Glu Met Ile Asn Thr
            35                  40                  45

Ile Lys Ser Ser Thr Glu Glu Leu Ile Lys Ser Ile Pro Asn Ser Val
 50                  55                  60

Ser Leu Arg Ala Gly Cys Asp Ile Phe Met Arg Phe Val Leu Arg Asn
 65                  70                  75                  80

Leu His Leu Tyr Gly Asp Trp Glu Asn Cys Lys Gln His Leu Ile Glu
                85                  90                  95

Asn Gly Gln Leu Phe Val Ser Arg Ala Lys Lys Ser Arg Asn Lys Ile
            100                 105                 110

Ala Glu Ile Gly Val Asp Phe Ile Ala Asp Asp Ile Ile Leu Val
        115                 120                 125

His Gly Tyr Ser Arg Ala Val Phe Ser Leu Leu Asn His Ala Ala Asn
        130                 135                 140

Lys Phe Ile Arg Phe Arg Cys Val Val Thr Glu Ser Arg Pro Ser Lys
145                 150                 155                 160

Gln Gly Asn Gln Leu Tyr Thr Leu Leu Glu Gln Lys Gly Ile Pro Val
            165                 170                 175

Thr Leu Ile Val Asp Ser Ala Val Gly Ala Val Ile Asp Lys Val Asp
            180                 185                 190

Lys Val Phe Val Gly Ala Glu Gly Val Ala Glu Ser Gly Gly Ile Ile
            195                 200                 205

Asn Leu Val Gly Thr Tyr Ser Val Gly Val Leu Ala His Asn Ala Arg
        210                 215                 220

Lys Pro Phe Tyr Val Val Thr Glu Ser His Lys Phe Val Arg Met Phe
225                 230                 235                 240

Pro Leu Ser Ser Asp Asp Leu Pro Met Ala Gly Pro Pro Leu Asp Phe
                245                 250                 255

Thr Arg Arg Thr Asp Asp Leu Glu Asp Ala Leu Arg Gly Pro Thr Ile
            260                 265                 270

Asp Tyr Thr Ala Gln Glu Tyr Ile Thr Ala Leu Ile Thr Asp Leu Gly
        275                 280                 285

Val Leu Thr Pro Ser Ala Val Ser Glu Glu Leu Ile Lys Met Trp Tyr
        290                 295                 300

Asp
305

<210> SEQ ID NO 55
<211> LENGTH: 846
<212> TYPE: DNA
<213> ORGANISM: Sacharomyces cerevisiae

<400> SEQUENCE: 55
atgtccgaat atcagccaag tttatttgct ttaaatccaa tgggtttctc accattggat    60
ggttctaaat caaccaacga aaatgtatct gcttccactt ctactgccaa accaatggtt   120
ggccaattga tttttgataa attcatcaag actgaagagg atccaattat caaacaggat   180
accccttcga accttgattt tgattttgct cttccacaaa cggcaactgc acctgatgcc   240
aagaccgttt tgccaattcc ggagctagat gacgctgtag tggaatcttt cttttcgtca   300
agcactgatt caactccaat gtttgagtat gaaaacctag aagacaactc taaagaatgg   360
acatccttgt tgacaatga cattccagtt accactgacg atgtttcatt ggctgataag   420
gcaattgaat ccactgaaga agtttctctg gtaccatcca atctggaagt ctcgacaact   480
```

```
tcattcttac ccactcctgt tctagaagat gctaaactga ctcaaacaag aaaggttaag      540
aaaccaaatt cagtcgttaa gaagtcacat catgttggaa aggatgacga atcgagactg      600
gatcatctag gtgttgttgc ttacaaccgc aaacagcgtt cgattccact ttctccaatt      660
gtgcccgaat ccagtgatcc tgctgctcta aaacgtgcta gaaacactga agccgccagg      720
cgttctcgtg cgagaaagtt gcaaagaatg aaacaacttg aagacaaggt tgaagaattg      780
ctttcgaaaa attatcactt ggaaaatgag gttgccagat aaagaaatt agttggcgaa      840 cgctga                                                                846
```

```
<210> SEQ ID NO 56
<211> LENGTH: 281
<212> TYPE: PRT
<213> ORGANISM: Saccharomyces cerevisiae

<400> SEQUENCE: 56
```

Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
            260                 265                 270

Arg Leu Lys Lys Leu Val Gly Glu Arg
        275                 280

```
<210> SEQ ID NO 57
<211> LENGTH: 1320
```

-continued

```
<212> TYPE: DNA
<213> ORGANISM: Saccharomyces cerevisiae

<400> SEQUENCE: 57
atggtcacaa aacatcagat tgaagaggat cacttggatg gagctacgac ggatcccgaa      60
gttaaacggg taaaattaga aaacaacgtt gaagaaatac aacctgagca ggctgagacc     120
aataaacaag agggcaccga taaagagaat aaggaaagt tcgagaaaga aactgagaga     180
ataggaggat ctgaagtggt tacagatgtg aaaaaggaa ttgtcaaatt tgaatttgat     240
ggtgttgaat acacattcaa agagagaccc agtgtcgtag aggaaaatga aggtaaaatt     300
gagtttaggg tggtgaataa tgataatact aaagaaaaca tgatggtcct aactggatta     360
aaaaacattt ttcaaaagca attaccaaaa atgcccaaag aatacattgc caggttagtc     420
tatgatcgaa gtcatctttc catggctgtc attaggaagc cattgactgt cgtaggtggc     480
ataacatatc gacctttcga taagagagaa ttcgcagaaa ttgttttctg tgccatcagt     540
tcgacggaac aggtacgcgg ttatggtgcg catctaatga atcacttaaa agactatgtt     600
agaaatacct cgaacataaa atattttttg acatatgcag ataattacgc tattggatac     660
tttaaaaagc aaggcttcac taagagaaatc acgttggata aaagtatatg gatgggatat     720
attaaagatt atgaaggtgg tacgctgatg caatgttcta tgttaccaag aatacgatat     780
ttggacgcag gtaagattct attattacaa gaagcggccc tgcgaagaaa aataagaacg     840
atttcgaaat cgcatattgt aaggcctggt ttagagcaat tcaaagactt aaacaatatc     900
aaaccgattg atccaatgac tattcctggc ttgaaagaag ccggctggac tcccgagatg     960
gatgcgttgg cacaacgtcc caagcgtggt ccacacgatg cagcaataca gaatatactc    1020
acagagctac aaaatcatgc agcagcttgg cccttcttac aacccgttaa taagaggag     1080
gtcccccgact attatgattt tatcaaagag ccaatggact tgagcaccat ggaaataaaa    1140
ttagagagca acaaatatca gaagatggaa gacttcatat atgatgccag attggtgttt    1200
aacaattgcc gaatgtacaa tggcgagaat acgtcgtatt acaagtatgc taataggcta    1260
gagaaattct tcaataataa agtaaaagaa atacctgaat attctcacct tattgattaa    1320
```

<210> SEQ ID NO 58
<211> LENGTH: 439
<212> TYPE: PRT
<213> ORGANISM: Saccharomyces cerevisiae

<400> SEQUENCE: 58

Met Val Thr Lys His Gln Ile Glu Glu Asp His Leu Asp Gly Ala Thr
1               5                   10                  15

Thr Asp Pro Glu Val Lys Arg Val Lys Leu Glu Asn Asn Val Glu Glu
            20                  25                  30

Ile Gln Pro Glu Gln Ala Glu Thr Asn Lys Gln Glu Gly Thr Asp Lys
        35                  40                  45

Glu Asn Lys Gly Lys Phe Glu Lys Glu Thr Glu Arg Ile Gly Gly Ser
    50                  55                  60

Glu Val Val Thr Asp Val Glu Lys Gly Ile Val Lys Phe Glu Phe Asp
65                  70                  75                  80

Gly Val Glu Tyr Thr Phe Lys Glu Arg Pro Ser Val Val Glu Glu Asn
                85                  90                  95

Glu Gly Lys Ile Glu Phe Arg Val Val Asn Asn Asp Asn Thr Lys Glu
            100                 105                 110

Asn Met Met Val Leu Thr Gly Leu Lys Asn Ile Phe Gln Lys Gln Leu

```
                115                 120                 125
Pro Lys Met Pro Lys Glu Tyr Ile Ala Arg Leu Val Tyr Asp Arg Ser
130                 135                 140

His Leu Ser Met Ala Val Ile Arg Lys Pro Leu Thr Val Val Gly Gly
145                 150                 155                 160

Ile Thr Tyr Arg Pro Phe Asp Lys Arg Glu Phe Ala Glu Ile Val Phe
                165                 170                 175

Cys Ala Ile Ser Ser Thr Glu Gln Val Arg Gly Tyr Gly Ala His Leu
            180                 185                 190

Met Asn His Leu Lys Asp Tyr Val Arg Asn Thr Ser Asn Ile Lys Tyr
        195                 200                 205

Phe Leu Thr Tyr Ala Asp Asn Tyr Ala Ile Gly Tyr Phe Lys Lys Gln
    210                 215                 220

Gly Phe Thr Lys Glu Ile Thr Leu Asp Lys Ser Ile Trp Met Gly Tyr
225                 230                 235                 240

Ile Lys Asp Tyr Glu Gly Gly Thr Leu Met Gln Cys Ser Met Leu Pro
                245                 250                 255

Arg Ile Arg Tyr Leu Asp Ala Gly Lys Ile Leu Leu Leu Gln Glu Ala
            260                 265                 270

Ala Leu Arg Arg Lys Ile Arg Thr Ile Ser Lys Ser His Ile Val Arg
        275                 280                 285

Pro Gly Leu Glu Gln Phe Lys Asp Leu Asn Asn Ile Lys Pro Ile Asp
    290                 295                 300

Pro Met Thr Ile Pro Gly Leu Lys Glu Ala Gly Trp Thr Pro Glu Met
305                 310                 315                 320

Asp Ala Leu Ala Gln Arg Pro Lys Arg Gly Pro His Asp Ala Ala Ile
                325                 330                 335

Gln Asn Ile Leu Thr Glu Leu Gln Asn His Ala Ala Trp Pro Phe
            340                 345                 350

Leu Gln Pro Val Asn Lys Glu Glu Val Pro Asp Tyr Tyr Asp Phe Ile
    355                 360                 365

Lys Glu Pro Met Asp Leu Ser Thr Met Glu Ile Lys Leu Glu Ser Asn
370                 375                 380

Lys Tyr Gln Lys Met Glu Asp Phe Ile Tyr Asp Ala Arg Leu Val Phe
385                 390                 395                 400

Asn Asn Cys Arg Met Tyr Asn Gly Glu Asn Thr Ser Tyr Tyr Lys Tyr
                405                 410                 415

Ala Asn Arg Leu Glu Lys Phe Phe Asn Asn Lys Val Lys Glu Ile Pro
            420                 425                 430

Glu Tyr Ser His Leu Ile Asp
        435

<210> SEQ ID NO 59
<211> LENGTH: 2259
<212> TYPE: DNA
<213> ORGANISM: Saccharomyces cerevisiae

<400> SEQUENCE: 59
atggcaagca tcggttcgca agtgagaaaa gctgcttcta gtattgaccc tatcgtcacg      60
gattacgcag tgggctactt taaccacttg tccggaataa cttttgatgc tgttcaaagt     120
aagcaggtag atttgtccac tgaagtgcaa tttgtgtccg atttattgat tgatgcgggt     180
gcgtcaaagg ctaagttaa agaactatcg gaaagtattt tgaagcaatt gactactcaa     240
ctaaaggaga acgaagccaa attggaattg accggtgata cgtccaagag attacttgat     300
```

```
attaatgtct taaagagtca taacagtaaa tccgatatca acgtctcatt aagcatgctg    360
ggtgtgaacg gtgacatcga acatactggt agaaagatgg aaacaagagt tgatttgaaa    420
aaactggcca aggctgaaca aaagatcgca aagaaagtcg ccaagagaaa taacaaattt    480
gttaaatacg aggcttctaa attgatcaat gaccaaaagg aggaggatta cgattctttc    540
tttttgcaaa tcaacccttt agaattcggt tcatccgctg gtaaatccaa ggatatccat    600
attgacactt tcgacttgta cgttggtgac ggtcaaagaa ttttgtccaa cgcccaattg    660
actctaagtt ttggtcacag atatggtctt gtgggccaaa atggtattgg taaatctact    720
ttgttaaggg ctctatctag aagagagctg aacgtcccca acatgtttc gattttacac    780 gtggaacaag agttaagagg tgatgataca aaggctttac aaagtgtgct ggatgcagac    840
gtttggagaa acaactatt aagtgaagaa gccaagatca atgaaagatt aaaggaaatg    900
gatgtattaa acaggaatt cgaagaagac agtttagaag ttaaaaaatt ggacaatgaa    960
agagaagact tggataacca tttgatacag atttctgaca aattagtcga tatggaatct   1020
gacaaggctg aagctagggc agcatcaatc ttatatggtt tggggttcag tacggaggca   1080
cagcaacaac ccactaattc cttttccggt ggttggagaa tgagattgtc cttggcaaga   1140
gccttattct gtcaaccaga tcttttgttg ttagatgaac cttccaatat gttggatgtg   1200
ccatccatcg cttatttagc agagtatttg aaaacatatc caaatacagt tttgacagtt   1260
tctcacgacc gtgcattctt gaatgaagtg gctacagata tcatttatca acacaacgaa   1320
agactagact attacagagg ccaagatttc gataccttt acaccacaaa ggaggaacgt   1380
agaaagaatg ctcaacgtga gtatgataac caaatggttt acagaaagca cttgcaagag   1440
tttattgaca aatacagata caatgctgcc aaatcacagg aagctcaatc aagaattaag   1500
aaattggaaa aattgcccgt tttggagcca cctgaacaag acaaaaccat tgatttcaaa   1560
ttccctgaat gtgataaatt gtctccacca attatccaat gcaagacgt ttcctttggt   1620 tatgatgaaa acaacctatt attgaaagat gttaacctgg acgttcaaat ggattccaga   1680
attgcccttg taggtgccaa tggttgtggt aagactacac tgttgaagat tatgatggag   1740 cagtaagac cactaaaagg cttgtatca agaaacccaa gattacgtat aggctacttc   1800
actcaacatc atgtggattc tatggatttg accacgtctg cagtggactg gatgtccaaa   1860
tccttcccag gtaaaactga tgaagagtat agacgtcatc taggttcatt tggtatcact   1920
ggtaccctgg gtctacaaaa gatgcaatta ttatccggtg gtcaaaaatc tcgtgtagca   1980
ttcgctgcat tgtgttaaa taatccacac attttggttc tggatgaacc ttctaaccat   2040
ttggatacca ctggtctaga cgctttggta gaagccttga aaaatttcaa cggtggtgtc   2100
ttaatggttt cccatgatat ctctgttatt gactctgttt gtaaagagat tgggtttca   2160 gagcaaggta ctgtcaagag gttcgaaggt acaatttacg actatagaga ttacatcttg   2220
cagtctgctg atgctgcagg tgtggttaaa aagcattga                          2259
```

<210> SEQ ID NO 60
<211> LENGTH: 752
<212> TYPE: PRT
<213> ORGANISM: Saccharomyces cerevisiae

<400> SEQUENCE: 60

```
Met Ala Ser Ile Gly Ser Gln Val Arg Lys Ala Ala Ser Ser Ile Asp
1               5                   10                  15

Pro Ile Val Thr Asp Tyr Ala Val Gly Tyr Phe Asn His Leu Ser Gly
```

-continued

```
                20                  25                  30
Ile Thr Phe Asp Ala Val Gln Ser Lys Gln Val Asp Leu Ser Thr Glu
            35                  40                  45
Val Gln Phe Val Ser Asp Leu Leu Ile Asp Ala Gly Ala Ser Lys Ala
 50                  55                  60
Lys Val Lys Glu Leu Ser Glu Ser Ile Leu Lys Gln Leu Thr Thr Gln
 65                  70                  75                  80
Leu Lys Glu Asn Glu Ala Lys Leu Glu Leu Thr Gly Asp Thr Ser Lys
                85                  90                  95
Arg Leu Leu Asp Ile Asn Val Leu Lys Ser His Asn Ser Lys Ser Asp
            100                 105                 110
Ile Asn Val Ser Leu Ser Met Leu Gly Val Asn Gly Asp Ile Glu His
            115                 120                 125
Thr Gly Arg Lys Met Glu Thr Arg Val Asp Leu Lys Lys Leu Ala Lys
            130                 135                 140
Ala Glu Gln Lys Ile Ala Lys Lys Val Ala Lys Arg Asn Asn Lys Phe
145                 150                 155                 160
Val Lys Tyr Glu Ala Ser Lys Leu Ile Asn Asp Gln Lys Glu Glu Asp
            165                 170                 175
Tyr Asp Ser Phe Phe Leu Gln Ile Asn Pro Leu Glu Phe Gly Ser Ser
            180                 185                 190
Ala Gly Lys Ser Lys Asp Ile His Ile Asp Thr Phe Asp Leu Tyr Val
            195                 200                 205
Gly Asp Gly Gln Arg Ile Leu Ser Asn Ala Gln Leu Thr Leu Ser Phe
            210                 215                 220
Gly His Arg Tyr Gly Leu Val Gly Gln Asn Gly Ile Gly Lys Ser Thr
225                 230                 235                 240
Leu Leu Arg Ala Leu Ser Arg Arg Glu Leu Asn Val Pro Lys His Val
            245                 250                 255
Ser Ile Leu His Val Glu Gln Glu Leu Arg Gly Asp Asp Thr Lys Ala
            260                 265                 270
Leu Gln Ser Val Leu Asp Ala Asp Val Trp Arg Lys Gln Leu Leu Ser
            275                 280                 285
Glu Glu Ala Lys Ile Asn Glu Arg Leu Lys Glu Met Asp Val Leu Arg
290                 295                 300
Gln Glu Phe Glu Glu Asp Ser Leu Glu Val Lys Lys Leu Asp Asn Glu
305                 310                 315                 320
Arg Glu Asp Leu Asp Asn His Leu Ile Gln Ile Ser Asp Lys Leu Val
            325                 330                 335
Asp Met Glu Ser Asp Lys Ala Glu Ala Arg Ala Ala Ser Ile Leu Tyr
            340                 345                 350
Gly Leu Gly Phe Ser Thr Glu Ala Gln Gln Gln Pro Thr Asn Ser Phe
            355                 360                 365
Ser Gly Gly Trp Arg Met Arg Leu Ser Leu Ala Arg Ala Leu Phe Cys
            370                 375                 380
Gln Pro Asp Leu Leu Leu Leu Asp Glu Pro Ser Asn Met Leu Asp Val
385                 390                 395                 400
Pro Ser Ile Ala Tyr Leu Ala Glu Tyr Leu Lys Thr Tyr Pro Asn Thr
            405                 410                 415
Val Leu Thr Val Ser His Asp Arg Ala Phe Leu Asn Glu Val Ala Thr
            420                 425                 430
Asp Ile Ile Tyr Gln His Asn Glu Arg Leu Asp Tyr Tyr Arg Gly Gln
            435                 440                 445
```

```
Asp Phe Asp Thr Phe Tyr Thr Thr Lys Glu Glu Arg Arg Lys Asn Ala
    450                 455                 460
Gln Arg Glu Tyr Asp Asn Gln Met Val Tyr Arg Lys His Leu Gln Glu
465                 470                 475                 480
Phe Ile Asp Lys Tyr Arg Tyr Asn Ala Ala Lys Ser Gln Glu Ala Gln
            485                 490                 495
Ser Arg Ile Lys Lys Leu Glu Lys Leu Pro Val Leu Glu Pro Pro Glu
        500                 505                 510
Gln Asp Lys Thr Ile Asp Phe Lys Phe Pro Glu Cys Asp Lys Leu Ser
    515                 520                 525
Pro Pro Ile Ile Gln Leu Gln Asp Val Ser Phe Gly Tyr Asp Glu Asn
530                 535                 540
Asn Leu Leu Leu Lys Asp Val Asn Leu Asp Val Gln Met Asp Ser Arg
545                 550                 555                 560
Ile Ala Leu Val Gly Ala Asn Gly Cys Gly Lys Thr Thr Leu Leu Lys
            565                 570                 575
Ile Met Met Glu Gln Leu Arg Pro Leu Lys Gly Phe Val Ser Arg Asn
        580                 585                 590
Pro Arg Leu Arg Ile Gly Tyr Phe Thr Gln His His Val Asp Ser Met
    595                 600                 605
Asp Leu Thr Thr Ser Ala Val Asp Trp Met Ser Lys Ser Phe Pro Gly
610                 615                 620
Lys Thr Asp Glu Glu Tyr Arg Arg His Leu Gly Ser Phe Gly Ile Thr
625                 630                 635                 640
Gly Thr Leu Gly Leu Gln Lys Met Gln Leu Leu Ser Gly Gly Gln Lys
            645                 650                 655
Ser Arg Val Ala Phe Ala Ala Leu Cys Leu Asn Asn Pro His Ile Leu
        660                 665                 670
Val Leu Asp Glu Pro Ser Asn His Leu Asp Thr Thr Gly Leu Asp Ala
    675                 680                 685
Leu Val Glu Ala Leu Lys Asn Phe Asn Gly Gly Val Leu Met Val Ser
690                 695                 700
His Asp Ile Ser Val Ile Asp Ser Val Cys Lys Glu Ile Trp Val Ser
705                 710                 715                 720
Glu Gln Gly Thr Val Lys Arg Phe Glu Gly Thr Ile Tyr Asp Tyr Arg
            725                 730                 735
Asp Tyr Ile Leu Gln Ser Ala Asp Ala Ala Gly Val Val Lys Lys His
        740                 745                 750

<210> SEQ ID NO 61
<211> LENGTH: 7575
<212> TYPE: DNA
<213> ORGANISM: Yarrowia lipolytica

<400> SEQUENCE: 61
atgatacgcg gtgtgatcag gctggatcgt gatctacttc cgtgtccatt atcacatcat      60
gtcatcgtct tctcatctgg atcaatgtca tccaccaaag accggctgga gttttggaag     120
gaacagcaaa tgctcctgtc ctctcccgac tcccttccgt ctatcctcag tgctctttt     180 cagactattc cacactactc cgaccacgta tcgagggacg tggtagtcga cacgtggaaa     240
ctgctgctaa aggaacaccc tgccgccctt caaaaggttg tgcccgtgct cgccaagcag     300
tttgccatct acaaaaagtc ctccacaaac aacctcatgg tgctgctgga gtggaccaac     360
tactttgtgt ccttctccct gaccaacgcc gggtccgagc tcaacgactt tgtcttcaag     420
```

```
gacctcattt ccatgcaggc cgagctcgtg gacctgtgct cagcatgcaa ccgggagcga    480
atggccaaga gcgctctgag gcagacccga gccgcgtttg cagcctgcat cacagctaac    540
ggagctctga ccaaactgct gaacgtatgc cttccaggca cccccacgtc tacggctctg    600
ctgggctgtc tagcatctgc atgcgctgaa aatgctcctc aaacttttga gcagctggat    660
ctttcagcct actcgcagtt ttacggcgcc aacgtgcttg gcgccaaggt tctgccctgc    720
aaaaacgcca ccaaacagtt ttgcacggga tactttggca acctgtctcg tgaccaaaag    780
tccaaggtcg cggctgatat ctttgatgcc accaagaagt cgattctgag gtctcccgag    840
tctgttctcg agtacgcaat tcccctgttg ctagagagtc tcgataaaga cgatgagtca    900
gcaaagaagc tggttgacgg catttccgct tccctggtca catgtctcaa gtcttccaat    960
cagctcactc gagatggagc tgtcacatgc atcggagtgg cctgtgctat ctctcacgag    1020
accctctact ccgagttggc caagactgtg tctaaggtga ctgtgttgga gcaaaaagtg    1080
gcctatggaa acgctattgc tggctgtcac gtgaccgatc cttctctgtc tgccgccctt    1140
gctcctgtgg ttaccaagga gaagaacgag attgccctga ctgctctgtc gcgtgccttt    1200
ttggtccact tttcccctga tcaggctaag actctctctt ctggactgtc tgactccaac    1260
gctggcgtcg tcaagacctg ggttctacag ctggtcaact tcccccaaca cgctgagcac    1320
gtgacaggtg agctggagaa gattctcgct tcttccacca tcgtcaaggg tgcgatttct    1380
ggtcttggag ctgtttacct gctcaccaag gctggaaaag ctgtaaaatc tgacaaggct    1440
ctggaactgg ctctatctcc tcgagtgtac accaaactca gtgcaggcga atttgtcact    1500
ggtttcaagg ctctggagtc gctgttcaag gaggttaacc ctgacaatgc ccccgacttt    1560
ggtaagacca tcttcttcta tgcttatggc gactccgagg tcaaggtgga cgttgactgc    1620
tctagattgg ttggtcccgc tctgaggagc aattactcgg atggtctggc tggggctgtc    1680
atttctggaa tttctgacac ccacgtcagc gagagaaagt actccaagtt gctttactcg    1740
ctgtttagtg ccgagaacaa ctgcgacaag gctcttgtcg atgggctaga ggtactgtgt    1800
ggcgtcggac tgtggattga gtccgttctg ggagcatctc gagatccccg aaagttgttg    1860
ttggacaatg agaagcatgt caagtcgatt ctgtcttcgg ctacctcctc caacctctat    1920
cctaccatcg ctacagtctg tttcattgct cctgacgtct tgctggtga ggttgccgag    1980 cagttcactg tttcgaacct ctcctgtgtc accactgagg ccgtgaccat cttcaacact    2040
cccgctgacg aactggcttt cgatatcaag cgaacggagc gtgtggctca caaaaactcc    2100
aaggaatacc aggacaagct gtgggaagaa aacctcaaga aggagctcca aaagaagaag    2160
ggtgttgtcg aaaagccaaa gtacaccaag gaggaacaaa tcaaggtaga cgaacagatg    2220
aagaaggagg cagaaattag aacggaggtc accgcagtcg cagatcacgt gacccggctc    2280
atgggcatca tttccgcccct ctccaaggag gccatgacgg ttgataacgg caaagaaacg    2340
tggtttggac cggccatgac gctcatgctc gagctcctca gacacccaa cgtggatgtg    2400 ctttgttcca gtcacgtgac caagactctc acggacatgt cttggatcac caacgacaag    2460
ctgggttcca ttagacccctt cctggccgtc tgcctgctca gaatgtatgg taatcacgtg    2520
agcgaggacc tccagaagga gtcacgtgac tctctcatca cgcgggtgct gtacaagatt    2580
cattctgtgg ccatgtcttc tcctcttgac gctatttctc tgattttcgt gcttcccatt    2640
gtcttgtttg tgctcaagaa ccagtctcgt gacaaggacg tggctgagga gcaaacgcat    2700
cttgccattg agattgtcac ttgtcacacc tctgcttttg ccgacgtgat tactcctcga    2760
```

```
tctgaaatca tgagcgccct cattcagctc atgaagagca ctcccaccaa ggccaagctt   2820
gctcgtgagt gtctgtactc tgtggttgag cacgtggctc tgacaattac gaaacccgaa   2880
gagcacgtgt tgctgagtaa cctgttcact ggagacactg gtgttcgtca tgctattctg   2940
gaggctgttg acgctcatct cactcttgat gactcctctc ctgaactcta cgtgacctgt   3000
ttcgatgtgg acgacgtgaa ccgagaactt gccgagcaga tttactccga gaacaagctc   3060
tgcaagccct cttcttctgt tcttctcccc ttcctggctg ctgagtcgtc ttctctgcgc   3120
ctgtcttcgg cacgtgccta tgctgccact gccgaagctg actcctacaa ccagctcatg   3180
gcctacatta tcgaggcttc tgtgcccatt cctcctaccc tggaccagta cggaaagccc   3240
aagaagggcg agtctgcacg tgaccagtgg gaagctcgat gcggagctgg tctagctgtt   3300
cacgagatgg cacctggcat gtctcccgag catgtgattt cgttcattga gttccttgtc   3360
gaaaccggct actctgatgt caactctgac gtccgacagg agttcaatga tgccggtctg   3420
gctcttgttg atcagcatgg cctcaagaac gttgaggagc tgatgaagat cattcagaac   3480
cgactcaaca aggcgtctaa cggctccgag agcgatgacc acgtgatttc gtcttgtgtt   3540
gttctgtatg gtgctctggc ccgccacctg gaatcttcag attcccgtct gcctgtcatc   3600
tacgaccgaa tgttggttgc tctagatact ccttctgagt ctgtgcagtt ccgagtctcc   3660
gaatgtcttt ctggactggt cagcaagatg acaagaagg ctagagatgg ctacttggac   3720
cagctcaccg agaagcttct ttctgactct tctctcgcca ttcgacgagg agcagcatat   3780
ggtattgctg gtctcgttag aggaggcgga attgcttcca ttggagagac tgatctcatg   3840
cgaaccctga cagatgctat ggagaacaag aagtcgtctg ccgcccgtca gagtgcccag   3900
tttgtggtcg agactctgtc gatggcactc cagcgacact tgagcccta tgcctgcag    3960
ctcatgcctc tggtgcttgc tgctcttggt gatcccgttt cgaggtccg agaagctacc   4020
aacgatgctt ctcgtcaggt tatgaagcac accactgcct acggagtgac caaactcatt   4080
cccatggcca ttgaaaaacct caacctcact gcttggcgat ctaagagagg agctgtggaa   4140
ttgctcggta acatggccta cctgtcccccс catgaactgt ccaccaacct gtcgctaatt   4200
gtccccgaga ttgtggcggt gctcaacgat acgcacaagg aggtgcgggc cgcggctaac   4260
agctctctca accggtttgg tcacgtgatt tccaaccccg agattcaggc tcttgttccc   4320
aagctcattg gtgccattgc cgagcctgag aagaccgagg ttgctctgga cggtctgctc   4380
aagacccagt tgtgcatta cattgacgct ccctccctcg ctctcattag tcacgtgctc   4440
cagcgtggtc ttggagaccg atccgccgca gtcaagaaga aggcttgtca gattgttggc   4500
aacatggcca ttttgacttc ggctcaggac attgcacctt acttgcccga gctgactgtt   4560
tccctggaga ccgccatggt cgatcccgta cctggcactc gtgctactgc tgcccgggct   4620
ctgggttctc ttgtcgagaa gctgggcgag cctgcgttcc ctgatctggt ccctcgactt   4680
ctttccactc tcagagacga gtctcgagct ggagaccacc ttggtgctgc ccagggtctg   4740
tctgaggttg tgtgcggtct gggtcttcga agctggaag aaattctgcc tcaggtgatc   4800
aaatcctgcg cttccccccaa gaatcacatt cgagctgctt tcatgccgct gatgatcttc   4860
ctgcctgcca ccttggcaa ctcgctgacc ccttacctgt cccagatcat tcctgtgatt   4920
ctttctggac ttgccgatga tgttgattcc gtcagagacg cttccctcaa ggctggtcgg   4980
ctcctggtgt ccaacttctc cagcaagtct gttgacctgc tgttgcccga gcttctcgtc   5040
ggcatgtctg actccaacca ccgaattcga cttgcctcgg ttgaactcat gggagaccta   5100
ctcttccagc tcactggtct caccaagaac gagcttgatg agtctgatga tgtcaacgca   5160
```

```
ggccaggccc tgctctcgtt gctgggacaa cagactcgag acactgttct ggccaacttg    5220
tttgtttgtc gagcagatac ctctggacag gtgcgacttg cgtcgatcga aatctggaaa    5280
gcgctggtgg ccaacacccc tcgaactgtc aaggagattc ttcccgagct caccaaccag    5340
gtggttaccc ggctggcttc tcgggaccac gagcagcgag aaatcgccgc ctccaccctc    5400
ggagaactcg tccgacgagt ctcggactcc ctgcagcagc ttctccctac tctgcagacc    5460
aacctcgaca actccgactc tgaccagaaa cagggtatct gcattgctct caaggagctc    5520
atcgtctcct cctctagaga ccagctggac gcccataaga cgaccgttgt tcacattctg    5580
cacgagactc tgaccgactc gtcacgcgat gtgcgttccg ctgccgcctc tgcgttcgat    5640
gcctacaacg agattatggg aaactcggct gtcgacgaca ttctccccaa gctgctgttg    5700
ctgctcaagg agcgtcccga ggctgctctg gcggctctca aggacatcat gcaatcgcga    5760
gccaactcga ttttccccgt tgtgctgccc aagctgctgt ctcagcctat ttccgtcttc    5820
aacgccgagg ccctcgcttc tctggctcct gttgctggcc agaccctgct gcgacgactt    5880
ccccaggtgg ttggcaacct tgtgtccgcc attatcagcg cgcgtgatca aaggacgac     5940 gaacgagcgt ctgctttgtt tgactctctt gtctccattt tcctgtcggt gtctgacgaa    6000
ggaatccatt cactcatgca gcagctcaag tccatggcca aggacgagga ctcggccgtg    6060
cgaacactgc tgttcgagac cctcacaccc tttttcaagg acacccagtt ggatctttct    6120
gcttactaca ttgactgggc tgagctgtgt atctatggtc ttgacgacga gtctgtttct    6180
tctgctgcca agagcgctct ggagactctg gtcaagaatc tgtccaagga ggagttggaa    6240
accctctcca agcctgctta ttccgctctc gccaacacct ccatccccct ggccggtatc    6300
aatgtgccca agggacccgc ctgtattctc cccatcttcg tgcagggtct catgtacggt    6360
acttcggacc agcgagaggc ctctgccaac ggtatgggat gcattgtaga gcgagttgac    6420
gcgtcgctgc tcaagttgca cgttacccag atcacaggtc ccctcattcg aaccattgga    6480
gaacggttcc cggcctctgt caaggtggct atcgttacaa ctctcaacct gctcctcaag    6540
aactgctctg cttttcctcaa gcctttcctg ccccagcttc agagaacctt tgccaagtgt    6600
```

```
cgagagcgac tggaggaggg aggagacgac atggagagtg ataagcggga ggacgaggcg    7560
gagatttggg agtag                                                     7575
```

<210> SEQ ID NO 62
<211> LENGTH: 2524
<212> TYPE: PRT
<213> ORGANISM: Yarrowia lipolytica

<400> SEQUENCE: 62

```
Met Ile Arg Gly Val Ile Arg Leu Asp Arg Asp Leu Leu Pro Cys Pro
1               5                   10                  15

Leu Ser His His Val Ile Val Phe Ser Ser Gly Ser Met Ser Ser Thr
            20                  25                  30

Lys Asp Arg Leu Glu Phe Trp Lys Glu Gln Gln Met Leu Leu Ser Ser
        35                  40                  45

Pro Asp Ser Leu Pro Ser Ile Leu Ser Ala Leu Phe Gln Thr Ile Pro
    50                  55                  60

His Tyr Ser Asp His Val Ser Arg Asp Val Val Asp Thr Trp Lys
65                  70                  75                  80

Leu Leu Leu Lys Glu His Pro Ala Ala Leu Gln Lys Val Val Pro Val
                85                  90                  95

Leu Ala Lys Gln Phe Ala Ile Tyr Lys Lys Ser Ser Thr Asn Asn Leu
            100                 105                 110

Met Val Leu Leu Glu Trp Thr Asn Tyr Phe Val Ser Phe Ser Leu Thr
        115                 120                 125

Asn Ala Gly Ser Glu Leu Asn Asp Phe Val Phe Lys Asp Leu Ile Ser
    130                 135                 140

Met Gln Ala Glu Leu Val Asp Leu Cys Ser Ala Cys Asn Arg Glu Arg
145                 150                 155                 160

Met Ala Lys Ser Ala Leu Arg Gln Thr Arg Ala Ala Phe Ala Ala Cys
                165                 170                 175

Ile Thr Ala Asn Gly Ala Leu Thr Lys Leu Leu Asn Val Cys Leu Pro
            180                 185                 190

Gly Thr Pro Thr Ser Thr Ala Leu Leu Gly Cys Leu Ala Ser Ala Cys
        195                 200                 205

Ala Glu Asn Ala Pro Gln Thr Phe Glu Gln Leu Asp Leu Ser Ala Tyr
    210                 215                 220

Ser Gln Phe Tyr Gly Ala Asn Val Leu Gly Ala Lys Val Leu Pro Cys
225                 230                 235                 240

Lys Asn Ala Thr Lys Gln Phe Cys Thr Gly Tyr Phe Gly Asn Leu Ser
                245                 250                 255

Arg Asp Gln Lys Ser Lys Val Ala Ala Asp Ile Phe Asp Ala Thr Lys
            260                 265                 270

Lys Ser Ile Leu Arg Ser Pro Glu Ser Val Leu Glu Tyr Ala Ile Pro
        275                 280                 285

Leu Leu Leu Glu Ser Leu Asp Lys Asp Glu Ser Ala Lys Lys Leu
    290                 295                 300

Val Asp Gly Ile Ser Ala Ser Leu Val Thr Cys Leu Lys Ser Ser Asn
305                 310                 315                 320

Gln Leu Thr Arg Asp Gly Ala Val Thr Cys Ile Gly Val Ala Cys Ala
                325                 330                 335

Ile Ser His Glu Thr Leu Tyr Ser Glu Leu Ala Lys Thr Val Ser Lys
            340                 345                 350

Val Thr Val Leu Glu Gln Lys Val Ala Tyr Gly Asn Ala Ile Ala Gly
```

```
            355                 360                 365
Cys His Val Thr Asp Pro Ser Leu Ser Ala Ala Leu Ala Pro Val Val
        370                 375                 380

Thr Lys Glu Lys Asn Glu Ile Ala Leu Thr Ala Leu Ser Arg Ala Phe
385                 390                 395                 400

Leu Val His Phe Ser Pro Asp Gln Ala Lys Thr Leu Ser Ser Gly Leu
                405                 410                 415

Ser Asp Ser Asn Ala Gly Val Val Lys Thr Trp Val Leu Gln Leu Val
                420                 425                 430

Asn Phe Pro Gln His Ala Glu His Val Thr Gly Glu Leu Glu Lys Ile
                435                 440                 445

Leu Ala Ser Ser Thr Ile Val Lys Gly Ala Ile Ser Gly Leu Gly Ala
            450                 455                 460

Val Tyr Leu Leu Thr Lys Ala Gly Lys Ala Val Lys Ser Asp Lys Ala
465                 470                 475                 480

Leu Glu Leu Ala Leu Ser Pro Arg Val Tyr Thr Lys Leu Ser Ala Gly
                485                 490                 495

Glu Phe Val Thr Gly Phe Lys Ala Leu Glu Ser Leu Phe Lys Glu Val
                500                 505                 510

Asn Pro Asp Asn Ala Pro Asp Phe Gly Lys Thr Ile Phe Phe Tyr Ala
                515                 520                 525

Tyr Gly Asp Ser Glu Val Lys Val Asp Val Asp Cys Ser Arg Leu Val
                530                 535                 540

Gly Pro Ala Leu Arg Ser Asn Tyr Ser Asp Gly Leu Ala Gly Ala Val
545                 550                 555                 560

Ile Ser Gly Ile Ser Asp Thr His Val Ser Glu Arg Lys Tyr Ser Lys
                565                 570                 575

Leu Leu Tyr Ser Leu Phe Ser Ala Glu Asn Asn Cys Asp Lys Ala Leu
                580                 585                 590

Val Asp Gly Leu Glu Val Leu Cys Gly Val Gly Leu Trp Ile Glu Ser
                595                 600                 605

Val Leu Gly Ala Ser Arg Asp Pro Arg Lys Leu Leu Leu Asp Asn Glu
            610                 615                 620

Lys His Val Lys Ser Ile Leu Ser Ser Ala Thr Ser Ser Asn Leu Tyr
625                 630                 635                 640

Pro Thr Ile Ala Thr Val Cys Phe Ile Ala Pro Asp Val Phe Ala Gly
                645                 650                 655

Glu Val Ala Glu Gln Phe Thr Val Ser Asn Leu Ser Cys Val Thr Thr
                660                 665                 670

Glu Ala Val Thr Ile Phe Asn Thr Pro Ala Asp Glu Leu Ala Phe Asp
                675                 680                 685

Ile Lys Arg Thr Glu Arg Val Ala His Lys Asn Ser Lys Glu Tyr Gln
            690                 695                 700

Asp Lys Leu Trp Glu Glu Asn Leu Lys Lys Glu Leu Gln Lys Lys Lys
705                 710                 715                 720

Gly Val Val Glu Lys Pro Lys Tyr Thr Lys Glu Gln Ile Lys Val
                725                 730                 735

Asp Glu Gln Met Lys Lys Glu Ala Glu Ile Arg Thr Glu Val Thr Ala
                740                 745                 750

Val Ala Asp His Val Thr Arg Leu Met Gly Ile Ile Ser Ala Leu Ser
                755                 760                 765

Lys Glu Ala Met Thr Val Asp Asn Gly Lys Glu Thr Trp Phe Gly Pro
770                 775                 780
```

```
Ala Met Thr Leu Met Leu Glu Leu Leu Arg His Pro Asn Val Asp Val
785                 790                 795                 800

Leu Cys Ser Ser His Val Thr Lys Thr Leu Thr Asp Met Ser Trp Ile
                805                 810                 815

Thr Asn Asp Lys Leu Gly Ser Ile Arg Pro Phe Leu Ala Val Cys Leu
            820                 825                 830

Leu Arg Met Tyr Gly Asn His Val Ser Glu Asp Leu Gln Lys Glu Ser
        835                 840                 845

Arg Asp Ser Leu Ile Thr Arg Val Leu Tyr Lys Ile His Ser Val Ala
850                 855                 860

Met Ser Ser Pro Leu Asp Ala Ile Ser Leu Ile Phe Val Leu Pro Ile
865                 870                 875                 880

Val Leu Phe Val Leu Lys Asn Gln Ser Arg Asp Lys Asp Val Ala Glu
                885                 890                 895

Glu Gln Thr His Leu Ala Ile Glu Ile Val Thr Cys His Thr Ser Ala
            900                 905                 910

Phe Ala Asp Val Ile Thr Pro Arg Ser Glu Ile Met Ser Ala Leu Ile
        915                 920                 925

Gln Leu Met Lys Ser Thr Pro Thr Lys Ala Lys Leu Ala Arg Glu Cys
930                 935                 940

Leu Tyr Ser Val Val Glu His Val Ala Leu Thr Ile Thr Lys Pro Glu
945                 950                 955                 960

Glu His Val Leu Leu Ser Asn Leu Phe Thr Gly Asp Thr Gly Val Arg
                965                 970                 975

His Ala Ile Leu Glu Ala Val Asp Ala His Leu Thr Leu Asp Asp Ser
            980                 985                 990

Ser Pro Glu Leu Tyr Val Thr Cys Phe Asp Val Asp Val Asn Arg
        995                 1000                1005

Glu Leu Ala Glu Gln Ile Tyr Ser Glu Asn Lys Leu Cys Lys Pro
    1010                1015                1020

Ser Ser Ser Val Leu Leu Pro Phe Leu Ala Ala Glu Ser Ser Ser
    1025                1030                1035

Leu Arg Leu Ser Ser Ala Arg Ala Tyr Ala Ala Thr Ala Glu Ala
    1040                1045                1050

Asp Ser Tyr Asn Gln Leu Met Ala Tyr Ile Ile Glu Ala Ser Val
    1055                1060                1065

Pro Ile Pro Pro Thr Leu Asp Gln Tyr Gly Lys Pro Lys Lys Gly
    1070                1075                1080

Glu Ser Ala Arg Asp Gln Trp Glu Ala Arg Cys Gly Ala Gly Leu
    1085                1090                1095

Ala Val His Glu Met Ala Pro Gly Met Ser Pro Glu His Val Ile
    1100                1105                1110

Ser Phe Ile Glu Phe Leu Val Glu Thr Gly Tyr Ser Asp Val Asn
    1115                1120                1125

Ser Asp Val Arg Gln Glu Phe Asn Asp Ala Gly Leu Ala Leu Val
    1130                1135                1140

Asp Gln His Gly Leu Lys Asn Val Glu Glu Leu Met Lys Ile Ile
    1145                1150                1155

Gln Asn Arg Leu Asn Lys Ala Ser Asn Gly Ser Glu Ser Asp Asp
    1160                1165                1170

His Val Ile Ser Ser Cys Val Val Leu Tyr Gly Ala Leu Ala Arg
    1175                1180                1185
```

His Leu Glu Ser Ser Asp Ser Arg Leu Pro Val Ile Tyr Asp Arg
    1190                1195                1200

Met Leu Val Ala Leu Asp Thr Pro Ser Glu Ser Val Gln Phe Arg
    1205                1210                1215

Val Ser Glu Cys Leu Ser Gly Leu Val Ser Lys Met Asp Lys Lys
    1220                1225                1230

Ala Arg Asp Gly Tyr Leu Asp Gln Leu Thr Glu Lys Leu Leu Ser
    1235                1240                1245

Asp Ser Ser Leu Ala Ile Arg Arg Gly Ala Ala Tyr Gly Ile Ala
    1250                1255                1260

Gly Leu Val Arg Gly Gly Gly Ile Ala Ser Ile Gly Glu Thr Asp
    1265                1270                1275

Leu Met Arg Thr Leu Thr Asp Ala Met Glu Asn Lys Lys Ser Ser
    1280                1285                1290

Ala Ala Arg Gln Ser Ala Gln Phe Val Val Glu Thr Leu Ser Met
    1295                1300                1305

Ala Leu Gln Arg His Phe Glu Pro Tyr Ala Leu Gln Leu Met Pro
    1310                1315                1320

Leu Val Leu Ala Ala Leu Gly Asp Pro Val Phe Glu Val Arg Glu
    1325                1330                1335

Ala Thr Asn Asp Ala Ser Arg Gln Val Met Lys His Thr Thr Ala
    1340                1345                1350

Tyr Gly Val Thr Lys Leu Ile Pro Met Ala Ile Glu Asn Leu Asn
    1355                1360                1365

Leu Thr Ala Trp Arg Ser Lys Arg Gly Ala Val Glu Leu Leu Gly
    1370                1375                1380

Asn Met Ala Tyr Leu Ser Pro His Glu Leu Ser Thr Asn Leu Ser
    1385                1390                1395

Leu Ile Val Pro Glu Ile Val Ala Val Leu Asn Asp Thr His Lys
    1400                1405                1410

Glu Val Arg Ala Ala Ala Asn Ser Ser Leu Asn Arg Phe Gly His
    1415                1420                1425

Val Ile Ser Asn Pro Glu Ile Gln Ala Leu Val Pro Lys Leu Ile
    1430                1435                1440

Gly Ala Ile Ala Glu Pro Glu Lys Thr Glu Val Ala Leu Asp Gly
    1445                1450                1455

Leu Leu Lys Thr Gln Phe Val His Tyr Ile Asp Ala Pro Ser Leu
    1460                1465                1470

Ala Leu Ile Ser His Val Leu Gln Arg Gly Leu Gly Asp Arg Ser
    1475                1480                1485

Ala Ala Val Lys Lys Lys Ala Cys Gln Ile Val Gly Asn Met Ala
    1490                1495                1500

Ile Leu Thr Ser Ala Gln Asp Ile Ala Pro Tyr Leu Pro Glu Leu
    1505                1510                1515

Thr Val Ser Leu Glu Thr Ala Met Val Asp Pro Val Pro Gly Thr
    1520                1525                1530

Arg Ala Thr Ala Ala Arg Ala Leu Gly Ser Leu Val Glu Lys Leu
    1535                1540                1545

Gly Glu Pro Ala Phe Pro Asp Leu Val Pro Arg Leu Leu Ser Thr
    1550                1555                1560

Leu Arg Asp Glu Ser Arg Ala Gly Asp His Leu Gly Ala Ala Gln
    1565                1570                1575

Gly Leu Ser Glu Val Val Cys Gly Leu Gly Leu Arg Lys Leu Glu

-continued

```
            1580             1585             1590
Glu Ile Leu Pro Gln Val Ile Lys Ser Cys Ala Ser Pro Lys Asn
        1595             1600             1605
His Ile Arg Ala Ala Phe Met Pro Leu Met Ile Phe Leu Pro Ala
        1610             1615             1620
Thr Phe Gly Asn Ser Leu Thr Pro Tyr Leu Ser Gln Ile Ile Pro
        1625             1630             1635
Val Ile Leu Ser Gly Leu Ala Asp Asp Val Asp Ser Val Arg Asp
        1640             1645             1650
Ala Ser Leu Lys Ala Gly Arg Leu Leu Val Ser Asn Phe Ser Ser
        1655             1660             1665
Lys Ser Val Asp Leu Leu Leu Pro Glu Leu Leu Val Gly Met Ser
        1670             1675             1680
Asp Ser Asn His Arg Ile Arg Leu Ala Ser Val Glu Leu Met Gly
        1685             1690             1695
Asp Leu Leu Phe Gln Leu Thr Gly Leu Thr Lys Asn Glu Leu Asp
        1700             1705             1710
Glu Ser Asp Asp Val Asn Ala Gly Gln Ala Leu Leu Ser Leu Leu
        1715             1720             1725
Gly Gln Gln Thr Arg Asp Thr Val Leu Ala Asn Leu Phe Val Cys
        1730             1735             1740
Arg Ala Asp Thr Ser Gly Gln Val Arg Leu Ala Ser Ile Glu Ile
        1745             1750             1755
Trp Lys Ala Leu Val Ala Asn Thr Pro Arg Thr Val Lys Glu Ile
        1760             1765             1770
Leu Pro Glu Leu Thr Asn Gln Val Val Thr Arg Leu Ala Ser Arg
        1775             1780             1785
Asp His Glu Gln Arg Glu Ile Ala Ala Ser Thr Leu Gly Glu Leu
        1790             1795             1800
Val Arg Arg Val Ser Asp Ser Leu Gln Gln Leu Leu Pro Thr Leu
        1805             1810             1815
Gln Thr Asn Leu Asp Asn Ser Asp Ser Asp Lys Gln Gly Ile
        1820             1825             1830
Cys Ile Ala Leu Lys Glu Leu Ile Val Ser Ser Arg Asp Gln
        1835             1840             1845
Leu Asp Ala His Lys Thr Thr Val Val His Ile Leu His Glu Thr
        1850             1855             1860
Leu Thr Asp Ser Ser Arg Asp Val Arg Ser Ala Ala Ala Ser Ala
        1865             1870             1875
Phe Asp Ala Tyr Asn Glu Ile Met Gly Asn Ser Ala Val Asp Asp
        1880             1885             1890
Ile Leu Pro Lys Leu Leu Leu Leu Lys Glu Arg Pro Glu Ala
        1895             1900             1905
Ala Leu Ala Ala Leu Lys Asp Ile Met Gln Ser Arg Ala Asn Ser
        1910             1915             1920
Ile Phe Pro Val Val Leu Pro Lys Leu Leu Ser Gln Pro Ile Ser
        1925             1930             1935
Val Phe Asn Ala Glu Ala Leu Ala Ser Leu Ala Pro Val Ala Gly
        1940             1945             1950
Gln Thr Leu Leu Arg Arg Leu Pro Gln Val Val Gly Asn Leu Val
        1955             1960             1965
Ser Ala Ile Ile Ser Ala Arg Asp Gln Lys Asp Asp Glu Arg Ala
        1970             1975             1980
```

-continued

```
Ser Ala Leu Phe Asp Ser Leu Val Ser Ile Phe Leu Ser Val Ser
    1985            1990            1995

Asp Glu Gly Ile His Ser Leu Met Gln Gln Leu Lys Ser Met Ala
    2000            2005            2010

Lys Asp Glu Asp Ser Ala Val Arg Thr Leu Leu Phe Glu Thr Leu
    2015            2020            2025

Thr Pro Phe Phe Lys Asp Thr Gln Leu Asp Leu Ser Ala Tyr Tyr
    2030            2035            2040

Ile Asp Trp Ala Glu Leu Cys Ile Tyr Gly Leu Asp Asp Glu Ser
    2045            2050            2055

Val Ser Ser Ala Ala Lys Ser Ala Leu Glu Thr Leu Val Lys Asn
    2060            2065            2070

Leu Ser Lys Glu Glu Leu Glu Thr Leu Ser Lys Pro Ala Tyr Ser
    2075            2080            2085

Ala Leu Ala Asn Thr Ser Ile Pro Leu Ala Gly Ile Asn Val Pro
    2090            2095            2100

Lys Gly Pro Ala Cys Ile Leu Pro Ile Phe Val Gln Gly Leu Met
    2105            2110            2115

Tyr Gly Thr Ser Asp Gln Arg Glu Ala Ser Ala Asn Gly Met Gly
    2120            2125            2130

Cys Ile Val Glu Arg Val Asp Ala Ser Leu Leu Lys Leu His Val
    2135            2140            2145

Thr Gln Ile Thr Gly Pro Leu Ile Arg Thr Ile Gly Glu Arg Phe
    2150            2155            2160

Pro Ala Ser Val Lys Val Ala Ile Val Thr Thr Leu Asn Leu Leu
    2165            2170            2175

Leu Lys Asn Cys Ser Ala Phe Leu Lys Pro Phe Leu Pro Gln Leu
    2180            2185            2190

Gln Arg Thr Phe Ala Lys Cys Leu Ser Asp Thr Gly Ser Glu Arg
    2195            2200            2205

Leu Arg Asn Glu Ala Ala Glu Ala Leu Gly Thr Leu Ile Thr Leu
    2210            2215            2220

Gln Ser Arg Val Asp Pro Leu Val Ser Glu Leu Val Thr Gly Val
    2225            2230            2235

Lys Asn Ser Thr Asp Glu Gly Val Thr Asn Ala Met Phe Lys Ala
    2240            2245            2250

Leu Gln Gly Val Val Ser Lys Ala Gly Gly Gln Met Ser Gln Gln
    2255            2260            2265

Ser Arg Asp Leu Val Phe Asn Leu Ala Asp Glu Val Thr Gly Leu
    2270            2275            2280

Asp Lys His Val Leu Ala Lys Met Leu Gly Gly Leu Ala Lys Val
    2285            2290            2295

Gly Asp Ala Ser Val Val Tyr Glu Val Ser Gln Lys Val Asn Asn
    2300            2305            2310

Ser Glu Phe Gly Ala Tyr Val Leu Asn Glu Leu Leu Val Ala Gln
    2315            2320            2325

Ala Gly Asp Glu Arg Val Ser Thr Arg Asp Leu Pro Asp Asp Ser
    2330            2335            2340

Pro Asp Tyr Val Thr Ser Thr Leu Glu Leu Met Lys Ser Glu Thr
    2345            2350            2355

Pro Ala Val Ser Asp Ala Ala Thr Leu Ala Cys Gly Lys Leu Leu
    2360            2365            2370
```

| | | | | | | | | | | |
|---|---|---|---|---|---|---|---|---|---|---|
| Leu | Ala | Phe | Gly | Gly | Leu | Pro | Phe | Glu | Ile | Thr | Lys | Ile | Leu | Leu |
| | 2375 | | | | 2380 | | | | | 2385 | | | | |

Thr Gln Leu Ala Gln Asn Ile Thr Ala Pro Ala Ser Ser Ser Ser
 2390                    2395                    2400

Asp Thr Arg Arg Leu Ala Leu Val Val Leu Arg Thr Val Ala Arg
 2405                    2410                    2415

Gln Gln His Ala Leu Thr Lys Pro His Val Thr Leu Leu Ala Thr
 2420                    2425                    2430

Ser Thr Phe Ala Cys Val Arg Glu Met Val Ile Pro Ile Lys Leu
 2435                    2440                    2445

Ala Ala Glu Lys Ala Trp Leu Ala Leu Phe Asp Leu Val Thr Gly
 2450                    2455                    2460

Ser Thr Glu Phe Asp Lys Trp Phe Gly Glu Val Gln Ser Glu Leu
 2465                    2470                    2475

Pro Asn Asn Gly Arg Ser Ile Gly Asp Tyr Thr Lys Arg Val Ala
 2480                    2485                    2490

Met Arg Leu Ala Gln Ala Glu Arg Glu Arg Leu Glu Glu Gly Gly
 2495                    2500                    2505

Asp Asp Met Glu Ser Asp Lys Arg Glu Asp Glu Ala Glu Ile Trp
 2510                    2515                    2520

Glu

```
<210> SEQ ID NO 63
<211> LENGTH: 4926
<212> TYPE: DNA
<213> ORGANISM: Yarrowia lipolytica

<400> SEQUENCE: 63
atggagttac aggaactgca agaaaacgag gcggaggctt tgaaggccat ctacatggac    60
gattttgttg acaccacaaa gtcatctgca tggaacaaaa cgccttcgcc atcatttgag   120
attcacatgc gatcgaccga cccggacgcc gaagatgccc tatccagttt aacgctccag   180
gtcgagctca cgagtaccta ccccaaaacg gtccctgtta ttcgcatcaa aaaccccaaa   240
aacatttttag catcacaggt ggccaagtta gagaagtgga tcgccgccac ctgcaaggag   300
ctcattggcg cagagatgat cttcgaggtc acctcgtata tccaggagcg actggaggat   360
tttcaacaga aggtgtccac cgccagtctg gaggaggagc ggcagatgaa gatcgagaag   420
caacaggagc agctacgaaa gcaaaagagc gacgaggcca aaaagcggga acaggaaaac   480
gcggaggaag acagagtgct agagatgatg gttgtggagg agctcaagcg acgcaaacag   540
cgggatgatg aagcgcaaaa ggcgcttact gcggagcgac aattgtcaaa cggcggccca   600
gtcatggccg attgcattga gtttgacaga ataacaacaa tctcgcgagc aggacaccca   660
gcaatcagtt tcagaagagt aggaggacaa atacccgtgc gagggtactc tttttggtaac   720
aattttttgg tgcggcccgt gacagaccca ccaaccgaca tatccctgct tctcacagaa   780
gttagacttc agggcacata ctggatccag gcagagggaa agaagatgat tcaactactc   840
gagtctgact tggacaactt gagaaagttt cgacacgaaa acgtcatcag tctctacgac   900
cacaagttcc aacgatgtcc agatacttcc ggatggacgc tatacctact ttccgaatat   960
tctcctggag gaactgtgtc tgatctgctt gataccgtgg gtaccgtgag tctcaaagtg  1020
acacgagtat gggctattca actactcgaa gccctggagg ctatccacaa ggctggattg  1080
gttcacaaga gtgtcaatgt ggacactgtg gtcctttttc gaaacgcaga aattggagaa  1140
acagtggtca gttgggata cactgttttt ggtcaacgtc ttaacgaaat gaattcggcg  1200
```

```
tgcacatttg atatgactgc ctctgtttca tcgatacaac acgacagtga tgcttggtca    1260
cctcctgagc tagtgcagca gagtggaaac aagcagacgc gtaagacaga cgtgtgggct    1320
ctgggtgtga tgcttcttca gaccttcatg ggtaagcagg tgacgtcaga gtattacgga    1380
cctacagatg tgatcaacag tctggatctg ggagattccc tggaagagtt ccttcgaaaa    1440
atgttcatgc cttctcccaa gaaacgtctt tctgcatttg agctcttgcc ttgtgaattc    1500
cttcgaactg gtgtcgactc gccagtgaag ttggcgtgtg cttccagcag tggtggaaaa    1560
cgaggtcgag gaagaagcat gtctacggat ggacgacctc accgggattc catgagtggt    1620 cttttccatgt ctcgatatgc tcaggacttc gaggaaacgg ttttgttagg acgaggtggc    1680
tatggtgtcg ttgtgaaggc tcgcaacaag ttggatggcc gtttctacgc catcaagcga    1740
gttcaacata cagcagacaa gttgacttcc attctaacag aggtcatgct gctgtctcgt    1800
ctcaataatc agtacgtggt tcgatacttt gctgcgtggt tggaagagtc ctacgactat    1860
caggatgagt ctgccatcga ggactacgat tcagaggagg agtggagcga aagtgtttct    1920
agagttgaaa catctgtcag cgcgtttcct gcccgtctca acggctcata cgaccaagat    1980
acgtttgacg agctctccat gaacgcctcg gtggacttca tctccaactc cctgcatcga    2040
gagtatcctg agattgaatt cggagtcagt tcagaggatg atgaagaccg cgagagtgac    2100
gatagcgaca gcgaagacga gacttcttcg gggagcgtat caacatcttc tcccatcaac    2160
agcagacaca aaactaccgt caagactctc gttggaaagg ctgctctggc tgagctgcgt    2220
gactctcctc gacacaagca agacaagtct ctggtaaaat ccaccctatt cattcaaatg    2280
gaatattgtg agaagcacac tttggcggat ttgatcaagc agaacctctc atctaaacct    2340
gaagactgct ggcgattgtt tggccagatt cttgatgctc tgagccacat tcattctcag    2400
ggcatcatcc atcgagatct caagcctatg aacattttca ttgactcatc tggtaatgtc    2460
aaggtcggag attttggact ggccaagaat atccatactg gaacttctct ggttggtgcc    2520
ggtgcaggaa ctggtgggag ctcgtctcag tacacaggtg aggatatgac aggcgacatc    2580
ggtactacgc tgtacgtcgc caatgaggta ttagccacag gcggggaggc caattacaac    2640
gagaaagttg acatgtactc tttgggtatc atcttttttcg agatggtgtt ccccatgaac    2700
actgcgatgg agcgtgtcta cattcttcga gacttgcgca accctaaggt catcttccct    2760
ccagcgtttg aggcttctaa gtacaacgaa cctcgtaaga tcattcgaag cttgctcgac    2820 catgaccccca gcaagagacc ttctgcccaa caactcttgg cctcaggcat tttgccgatt    2880
cctaataagg acaagactat caaggagtg attcgaagct tggtagaccc ctcgcccagt    2940
tcgccatggc tttctcaagt gtgtcgggct ctgttctcac gacctctcaa gacagcgcag    3000
gtgtttcttt acgaccgtgc aatcgctggt gagggcagta aatcggactc tcgcgattct    3060
cttctccagg ctcagatgat tgagcaaatc gaggcaactt tcagaaacca cggtgccatc    3120
aaggtcaaca atcgaccatt gctatttccg aagtctctca tatacaagtc cccaaatgtg    3180
gtgtcagtac tcgatcaagc gggtacaatt cttcagttgc ccttcgacct gacactccct    3240
catgctcgaa tgcttgccaa gggtcagact tactaccata gtctttctg ctgtgattat    3300 gtctatcgag cagatgagaa caatgtcgtt agccatcccc gccggtttgg agagattgac    3360
tttgacattg taacccagga ttctacggac ttgcctctgt atgacgccga ggctatccga    3420
gtactcgacc aggtgatcca gttgttccca tcttttaaaa acaacaacgt cgtcatttac    3480
attaaccatt gggatatcct gcagactatt ttggattcat gtcgtattgg gcaagcccag    3540
```

```
agagctgttg ctcttcggct tctggacgag accggacagg ccctgctcg ccaggttgtc    3600 aaggaagagc ttcgaaccaa gtactctgtc ggtgccaccg ctttggatga tttggaatca    3660
tttggattcc gagacgacat cgacaaggcc gaacaacgtc ttcgtaagat gatcgagggc    3720
agcgagcata ccactcggct gacagagtca ttcttgtgga ttcgaaaggt ttctacctat    3780
ctgaaacgtt ttggctgtac ccgtcgtgtc tacgttgctc cattgagtaa ttacaacgag    3840
gacttctacc gcagcggtct gatgtttcag gctgtcgttg aggataccgc tccacagaag    3900
cgcacgtcca ttctagctgt tggtggacga tatgaccgac tgattactcg gttcagacac    3960
gagtcattgg atcgaggagt tccccgcacg catgctgtcg gcttcaacct tgcttgggaa    4020
tcaatcttcg actccatgaa ggcctacaga gatgccttga tgaaaaagca aagaagaag     4080 ggcacggttc aggttctcag cacatccact tcgtcatctg ctctcgagtt gcaacgttgg    4140 taccctctc gttgtgatgc tctcgttacg tccttcaata gtaacacatt gcgcactgtt     4200
tgtctagatg ttttgaagga cttgtgggga gcaggtattc gagctgactt gtgccgagat    4260
tgttcatcat cggaggaact tgttgcgcgg gctcagagtg aaggtatcaa ttggatcatc    4320
atcgtcaagc agcatagtgg ctactcttct gctgcggccg cgtacaagcc ccttcgtgtc    4380
aagaatgttg cgcggaacga cgacactgat attgatagag atggaatcgt cggtcatatg    4440
atgactgagt tgaatgagcg gggtggatct tacagcaaca caaacgccct ggcacccct     4500 tctctgtctg tgcctcacga cccatcgcct ccagcttcca ttgtggatac tagcgatatc    4560
tatgccacca caaggtgtc tgtgatcacg aatgagtgga acaagagtaa gtcctccaag     4620
agaaccaacc agtggaacga cgaggaggaa cgtgcgttga cacacgcg ttcgctggta      4680 cacgacatcc aggaggctcc cattttcaca atcgatgtca aggaagatat acttgacgcc    4740
atttctgtga cttctctggc atcgtttgat gaatggcgtc gaaggtgat tggtatccag     4800 ccttcacata agccttacct ggcaaagatc tacaaccagc tggtcaagct gaaggaaaca    4860
cgatctacgg ctttactgta ttcacctaaa gcagacaagt tgattcttta caatctgagg    4920
aagtga                                                               4926
```

<210> SEQ ID NO 64
<211> LENGTH: 1641
<212> TYPE: PRT
<213> ORGANISM: Yarrowia lipolytica

<400> SEQUENCE: 64

Met Glu Leu Gln Glu Leu Gln Glu Asn Glu Ala Glu Ala Leu Lys Ala
1               5                   10                  15

Ile Tyr Met Asp Asp Phe Val Asp Thr Thr Lys Ser Ser Ala Trp Asn
            20                  25                  30

Lys Thr Pro Ser Pro Ser Phe Glu Ile His Met Arg Ser Thr Asp Pro
        35                  40                  45

Asp Ala Glu Asp Ala Leu Ser Ser Leu Thr Leu Gln Val Glu Leu Thr
    50                  55                  60

Ser Thr Tyr Pro Lys Thr Val Pro Val Ile Arg Ile Lys Asn Pro Lys
65                  70                  75                  80

Asn Ile Leu Ala Ser Gln Val Ala Lys Leu Glu Lys Trp Ile Ala Ala
                85                  90                  95

Thr Cys Lys Glu Leu Ile Gly Ala Glu Met Ile Phe Glu Val Thr Ser
            100                 105                 110

Tyr Ile Gln Glu Arg Leu Glu Asp Phe Gln Gln Lys Val Ser Thr Ala
        115                 120                 125

```
Ser Leu Glu Glu Arg Gln Met Lys Ile Glu Lys Gln Gln Glu Gln
    130                 135                 140

Leu Arg Lys Gln Lys Ser Asp Glu Ala Lys Lys Arg Glu Gln Glu Asn
145                 150                 155                 160

Ala Glu Glu Asp Arg Val Leu Glu Met Met Val Val Glu Glu Leu Lys
                165                 170                 175

Arg Arg Lys Gln Arg Asp Asp Glu Ala Gln Lys Ala Leu Thr Ala Glu
            180                 185                 190

Arg Gln Leu Ser Asn Gly Gly Pro Val Met Ala Asp Cys Ile Glu Phe
        195                 200                 205

Asp Arg Ile Thr Thr Ile Ser Arg Ala Gly His Pro Ala Ile Ser Phe
    210                 215                 220

Arg Arg Val Gly Gly Gln Ile Pro Val Arg Gly Tyr Ser Phe Gly Asn
225                 230                 235                 240

Asn Phe Leu Val Arg Pro Val Thr Asp Pro Pro Thr Asp Ile Ser Leu
                245                 250                 255

Leu Leu Thr Glu Val Arg Leu Gln Gly Thr Tyr Trp Ile Gln Ala Glu
            260                 265                 270

Gly Lys Lys Met Ile Gln Leu Leu Glu Ser Asp Leu Asp Asn Leu Arg
        275                 280                 285

Lys Phe Arg His Glu Asn Val Ile Ser Leu Tyr Asp His Lys Phe Gln
    290                 295                 300

Arg Cys Pro Asp Thr Ser Gly Trp Thr Leu Tyr Leu Leu Ser Glu Tyr
305                 310                 315                 320

Ser Pro Gly Gly Thr Val Ser Asp Leu Leu Asp Thr Val Gly Thr Val
                325                 330                 335

Ser Leu Lys Val Thr Arg Val Trp Ala Ile Gln Leu Leu Glu Ala Leu
            340                 345                 350

Glu Ala Ile His Lys Ala Gly Leu Val His Lys Ser Val Asn Val Asp
        355                 360                 365

Thr Val Val Leu Phe Arg Asn Ala Glu Ile Gly Glu Thr Val Val Lys
    370                 375                 380

Leu Gly Tyr Thr Val Phe Gly Gln Arg Leu Asn Glu Met Asn Ser Ala
385                 390                 395                 400

Cys Thr Phe Asp Met Thr Ala Ser Val Ser Ser Ile Gln His Asp Ser
                405                 410                 415

Asp Ala Trp Ser Pro Pro Glu Leu Val Gln Gln Ser Gly Asn Lys Gln
            420                 425                 430

Thr Arg Lys Thr Asp Val Trp Ala Leu Gly Val Met Leu Leu Gln Thr
        435                 440                 445

Phe Met Gly Lys Gln Val Thr Ser Glu Tyr Tyr Gly Pro Thr Asp Val
    450                 455                 460

Ile Asn Ser Leu Asp Leu Gly Asp Ser Leu Glu Glu Phe Leu Arg Lys
465                 470                 475                 480

Met Phe Met Pro Ser Pro Lys Lys Arg Leu Ser Ala Phe Glu Leu Leu
                485                 490                 495

Pro Cys Glu Phe Leu Arg Thr Gly Val Asp Ser Pro Val Lys Leu Ala
            500                 505                 510

Cys Ala Ser Ser Ser Gly Gly Lys Arg Gly Arg Gly Arg Ser Met Ser
        515                 520                 525

Thr Asp Gly Arg Pro His Arg Asp Ser Met Ser Gly Leu Ser Met Ser
    530                 535                 540
```

-continued

Arg Tyr Ala Gln Asp Phe Glu Glu Thr Val Leu Leu Gly Arg Gly Gly
545                 550                 555                 560
Tyr Gly Val Val Val Lys Ala Arg Asn Lys Leu Asp Gly Arg Phe Tyr
                565                 570                 575
Ala Ile Lys Arg Val Gln His Thr Ala Asp Lys Leu Thr Ser Ile Leu
                580                 585                 590
Thr Glu Val Met Leu Leu Ser Arg Leu Asn Asn Gln Tyr Val Val Arg
                595                 600                 605
Tyr Phe Ala Ala Trp Leu Glu Glu Ser Tyr Asp Tyr Gln Asp Glu Ser
            610                 615                 620
Ala Ile Glu Asp Tyr Asp Ser Glu Glu Glu Trp Ser Glu Ser Val Ser
625                 630                 635                 640
Arg Val Glu Thr Ser Val Ser Ala Phe Pro Ala Arg Leu Asn Gly Ser
                645                 650                 655
Tyr Asp Gln Asp Thr Phe Asp Glu Leu Ser Met Asn Ala Ser Val Asp
                660                 665                 670
Phe Ile Ser Asn Ser Leu His Arg Glu Tyr Pro Glu Ile Glu Phe Gly
            675                 680                 685
Val Ser Ser Glu Asp Asp Glu Asp Arg Glu Ser Asp Asp Ser Asp Ser
690                 695                 700
Glu Asp Glu Thr Ser Ser Gly Ser Val Ser Thr Ser Ser Pro Ile Asn
705                 710                 715                 720
Ser Arg His Lys Thr Thr Val Lys Thr Leu Val Gly Lys Ala Ala Leu
                725                 730                 735
Ala Glu Leu Arg Asp Ser Pro Arg His Lys Gln Asp Lys Ser Leu Val
                740                 745                 750
Lys Ser Thr Leu Phe Ile Gln Met Glu Tyr Cys Glu Lys His Thr Leu
            755                 760                 765
Ala Asp Leu Ile Lys Gln Asn Leu Ser Ser Lys Pro Glu Asp Cys Trp
770                 775                 780
Arg Leu Phe Gly Gln Ile Leu Asp Ala Leu Ser His Ile His Ser Gln
785                 790                 795                 800
Gly Ile Ile His Arg Asp Leu Lys Pro Met Asn Ile Phe Ile Asp Ser
                805                 810                 815
Ser Gly Asn Val Lys Val Gly Asp Phe Gly Leu Ala Lys Asn Ile His
                820                 825                 830
Thr Gly Thr Ser Leu Val Gly Ala Gly Ala Gly Thr Gly Gly Ser Ser
            835                 840                 845
Ser Gln Tyr Thr Gly Glu Asp Met Thr Gly Asp Ile Gly Thr Thr Leu
850                 855                 860
Tyr Val Ala Asn Glu Val Leu Ala Thr Gly Gly Glu Ala Asn Tyr Asn
865                 870                 875                 880
Glu Lys Val Asp Met Tyr Ser Leu Gly Ile Ile Phe Phe Glu Met Val
                885                 890                 895
Phe Pro Met Asn Thr Ala Met Glu Arg Val Tyr Ile Leu Arg Asp Leu
                900                 905                 910
Arg Asn Pro Lys Val Ile Phe Pro Pro Ala Phe Glu Ala Ser Lys Tyr
            915                 920                 925
Asn Glu Pro Arg Lys Ile Ile Arg Ser Leu Leu Asp His Asp Pro Ser
930                 935                 940
Lys Arg Pro Ser Ala Gln Gln Leu Leu Ala Ser Gly Ile Leu Pro Ile
945                 950                 955                 960
Pro Asn Lys Asp Lys Thr Ile Lys Glu Val Ile Arg Ser Leu Val Asp

```
              965                 970                 975
Pro Ser Pro Ser Ser Pro Trp Leu Ser Gln Val Cys Arg Ala Leu Phe
              980                 985                 990

Ser Arg Pro Leu Lys Thr Ala Gln Val Phe Leu Tyr Asp Arg Ala Ile
        995                1000                1005

Ala Gly Glu Gly Ser Lys Ser Asp Ser Arg Asp Ser Leu Leu Gln
    1010                1015                1020

Ala Gln Met Ile Glu Gln Ile Glu Ala Thr Phe Arg Asn His Gly
    1025                1030                1035

Ala Ile Lys Val Asn Asn Arg Pro Leu Leu Phe Pro Lys Ser Leu
    1040                1045                1050

Ile Tyr Lys Ser Pro Asn Val Val Ser Val Leu Asp Gln Ala Gly
    1055                1060                1065

Thr Ile Leu Gln Leu Pro Phe Asp Leu Thr Leu Pro His Ala Arg
    1070                1075                1080

Met Leu Ala Lys Gly Gln Thr Tyr Tyr His Lys Ser Phe Cys Cys
    1085                1090                1095

Asp Tyr Val Tyr Arg Ala Asp Glu Asn Val Val Ser His Pro
    1100                1105                1110

Arg Arg Phe Gly Glu Ile Asp Phe Asp Ile Val Thr Gln Asp Ser
    1115                1120                1125

Thr Asp Leu Pro Leu Tyr Asp Ala Glu Ala Ile Arg Val Leu Asp
    1130                1135                1140

Gln Val Ile Gln Leu Phe Pro Ser Phe Lys Asn Asn Asn Val Val
    1145                1150                1155

Ile Tyr Ile Asn His Trp Asp Ile Leu Gln Thr Ile Leu Asp Ser
    1160                1165                1170

Cys Arg Ile Gly Gln Ala Gln Arg Ala Val Ala Leu Arg Leu Leu
    1175                1180                1185

Asp Glu Thr Gly Gln Ala Pro Ala Arg Gln Val Val Lys Glu Glu
    1190                1195                1200

Leu Arg Thr Lys Tyr Ser Val Gly Ala Thr Ala Leu Asp Asp Leu
    1205                1210                1215

Glu Ser Phe Gly Phe Arg Asp Ile Asp Lys Ala Glu Gln Arg
    1220                1225                1230

Leu Arg Lys Met Ile Glu Gly Ser Glu His Thr Thr Arg Leu Thr
    1235                1240                1245

Glu Ser Phe Leu Trp Ile Arg Lys Val Ser Thr Tyr Leu Lys Arg
    1250                1255                1260

Phe Gly Cys Thr Arg Arg Val Tyr Val Ala Pro Leu Ser Asn Tyr
    1265                1270                1275

Asn Glu Asp Phe Tyr Arg Ser Gly Leu Met Phe Gln Ala Val Val
    1280                1285                1290

Glu Asp Thr Ala Pro Gln Lys Arg Thr Ser Ile Leu Ala Val Gly
    1295                1300                1305

Gly Arg Tyr Asp Arg Leu Ile Thr Arg Phe Arg His Glu Ser Leu
    1310                1315                1320

Asp Arg Gly Val Pro Arg Thr His Ala Val Gly Phe Asn Leu Ala
    1325                1330                1335

Trp Glu Ser Ile Phe Asp Ser Met Lys Ala Tyr Arg Asp Ala Leu
    1340                1345                1350

Met Lys Lys Gln Lys Lys Gly Thr Val Gln Val Leu Ser Thr
    1355                1360                1365
```

Ser Thr Ser Ser Ser Ala Leu Glu Leu Gln Arg Trp Tyr Pro Ser
1370                1375                    1380

Arg Cys Asp Ala Leu Val Thr Ser Phe Asn Ser Asn Thr Leu Arg
    1385                1390                1395

Thr Val Cys Leu Asp Val Leu Lys Asp Leu Trp Gly Ala Gly Ile
1400                1405                    1410

Arg Ala Asp Leu Cys Arg Asp Cys Ser Ser Glu Glu Leu Val
    1415                1420                1425

Ala Arg Ala Gln Ser Glu Gly Ile Asn Trp Ile Ile Ile Val Lys
1430                1435                    1440

Gln His Ser Gly Tyr Ser Ser Ala Ala Ala Ala Tyr Lys Pro Leu
    1445                1450                1455

Arg Val Lys Asn Val Ala Arg Asn Asp Asp Thr Asp Ile Asp Arg
1460                1465                    1470

Asp Gly Ile Val Gly His Met Met Thr Glu Leu Asn Glu Arg Gly
    1475                1480                1485

Gly Ser Tyr Ser Asn Thr Asn Ala Leu Ala Pro Pro Ser Leu Ser
1490                1495                    1500

Val Pro His Asp Pro Ser Pro Pro Ala Ser Ile Val Asp Thr Ser
1505                1510                    1515

Asp Ile Tyr Ala Thr Asn Lys Val Ser Val Ile Thr Asn Glu Trp
1520                1525                    1530

Asn Lys Ser Lys Ser Ser Lys Arg Thr Asn Gln Trp Asn Asp Glu
1535                1540                    1545

Glu Glu Arg Ala Leu Arg His Thr Arg Ser Leu Val His Asp Ile
1550                1555                    1560

Gln Glu Ala Pro Ile Phe Thr Ile Asp Val Lys Glu Asp Ile Leu
1565                1570                    1575

Asp Ala Ile Ser Val Thr Ser Leu Ala Ser Phe Asp Glu Trp Arg
1580                1585                    1590

Arg Lys Val Ile Gly Ile Gln Pro Ser His Lys Pro Tyr Leu Ala
1595                1600                    1605

Lys Ile Tyr Asn Gln Leu Val Lys Leu Lys Glu Thr Arg Ser Thr
1610                1615                    1620

Ala Leu Leu Tyr Ser Pro Lys Ala Asp Lys Leu Ile Leu Tyr Asn
1625                1630                    1635

Leu Arg Lys
1640

<210> SEQ ID NO 65
<211> LENGTH: 924
<212> TYPE: DNA
<213> ORGANISM: Yarrowia lipolytica

<400> SEQUENCE: 65
atggccaaat tcgacatcaa agagacatat ctgcgctttc tgcgggacga ccccgacatc    60
accatgcctg tcgcggccat tgaggccctg gtccagctgc tcagtgagac cgaaaccagc   120
acatcagccg agctgattca gactctcaag gaggcgagcg cggagctcaa gacgtctgtg   180
gacaactcta tgtcgctttc tgcaggctgt gatctgttta tgcgatttgt gttgcgaaat   240
atccgggaat atggcgactg ggaggcctgc aagggccatt tggtaaagaa cggaaggctg   300
tttgccgagc gaagtaaggc tgctcgaaag accatttcgg aaaagggtct agcatttgtg   360
cgggatgacg atgtcattct ggtccactct ttctcgcgaa cggtactggc ccttctggaa   420

-continued

```
catgctgcta agaacttggt gcgtttcaga gtgtttgtca cagaggctgc tcctagtgat      480
cagggtaagc gaatggccaa ggcattgagg gagagaggca ttcccgtgag tctaattgtg      540
gacaacgccg tcggatctgt gattgacgag gtgtccaagg tgttttgtgg tgccgaggga      600
gtggcggagt ctggaggagt catcaaccac gtcggatcat atcagattgc cgtgctagcc      660
aagaacgcaa ataagccctt ctacgtggtc accgagagtc acaagtttgt gcgaatcttc      720
cctctggccc aggccgatct gccagacacc aaaaagatgt tccacttcac tgttgaggag      780
cccgaggagc agaatgccga caagggtctg tcgccagtcg tcgactttac gcctcacgat      840
tacatcactg cacttatcac agatctggga gttctcactc caagtggcgt ttctgaggag      900
ctgattaaaa tgtggtatga gtaa                                             924
```

```
<210> SEQ ID NO 66
<211> LENGTH: 307
<212> TYPE: PRT
<213> ORGANISM: Yarrowia lipolytica

<400> SEQUENCE: 66

Met Ala Lys Phe Asp Ile Lys Glu Thr Tyr Leu Arg Phe Leu Arg Asp
1               5                   10                  15

Asp Pro Asp Ile Thr Met Pro Val Ala Ile Glu Ala Leu Val Gln
            20                  25                  30

Leu Leu Ser Glu Thr Glu Thr Ser Thr Ala Glu Leu Ile Gln Thr
        35                  40                  45

Leu Lys Glu Ala Ser Ala Glu Leu Lys Thr Ser Val Asp Asn Ser Met
 50                  55                  60

Ser Leu Ser Ala Gly Cys Asp Leu Phe Met Arg Phe Val Leu Arg Asn
 65                  70                  75                  80

Ile Arg Glu Tyr Gly Asp Trp Glu Ala Cys Lys Gly His Leu Val Lys
                85                  90                  95

Asn Gly Arg Leu Phe Ala Glu Arg Ser Lys Ala Ala Arg Lys Thr Ile
            100                 105                 110

Ser Glu Lys Gly Leu Ala Phe Val Arg Asp Asp Val Ile Leu Val
        115                 120                 125

His Ser Phe Ser Arg Thr Val Leu Ala Leu Leu Glu His Ala Ala Lys
130                 135                 140

Asn Leu Val Arg Phe Arg Val Phe Val Thr Glu Ala Ala Pro Ser Asp
145                 150                 155                 160

Gln Gly Lys Arg Met Ala Lys Ala Leu Arg Glu Arg Gly Ile Pro Val
                165                 170                 175

Ser Leu Ile Val Asp Asn Ala Val Gly Ser Val Ile Asp Glu Val Ser
            180                 185                 190

Lys Val Phe Cys Gly Ala Glu Gly Val Ala Glu Ser Gly Gly Val Ile
        195                 200                 205

Asn His Val Gly Ser Tyr Gln Ile Ala Val Leu Ala Lys Asn Ala Asn
    210                 215                 220

Lys Pro Phe Tyr Val Val Thr Glu Ser His Lys Phe Val Arg Ile Phe
225                 230                 235                 240

Pro Leu Ala Gln Ala Asp Leu Pro Asp Thr Lys Lys Met Phe His Phe
                245                 250                 255

Thr Val Glu Glu Pro Glu Glu Gln Asn Ala Asp Lys Gly Leu Ser Pro
            260                 265                 270

Val Val Asp Phe Thr Pro His Asp Tyr Ile Thr Ala Leu Ile Thr Asp
```

```
                275                 280                 285
Leu Gly Val Leu Thr Pro Ser Gly Val Ser Glu Glu Leu Ile Lys Met
        290                 295                 300

Trp Tyr Glu
305
```

<210> SEQ ID NO 67
<211> LENGTH: 1395
<212> TYPE: DNA
<213> ORGANISM: Yarrowia lipolytica

<400> SEQUENCE: 67

```
atggattcgg atactgagtc agtgaaacga agaaagtcct ccgggtccga aagcgagtcg      60
agcgtgcgag atccgaaacg aaccaagatt gaagatgagg atttccagga gaacggcata     120
gacgatgagg atgaggagga ggaagaggag gaagctaagg acgaagggga tgaagacgac     180
gaagaaaaag gagaggacga cgaggaggac gatgaagaaa agaaggcga ggatggagaa      240
ggagaggaag aagacgaaga ggaggatgag gagaagaagc gagaggagga ggagaagtac     300
gttaccagct tcaactttga tggtgtggaa tacaagtaca aagagcgacc agcagtgatt     360
gaggagcgtg aaggaaagat tgaatttcgt gttgtcaaca acgataactc caaggaaaac     420
ctcatgatcc tgacaggtct caagaacatt ttccagaaac agctgcccaa aatgcctcga     480
gagtacattg cccgactagt gtacgacaga agtcatgtgt caatggcagt tgttagaaag     540
cctctcacgg tggtcggagg aattacattt cggccgttcg ataccccgga gtttgctgaa     600
atcgtcttct gtgccatcag tagtacagag caggtccgag gatacggagc gcacttgatg     660
aaccatttga aggactacgt taaggctaca tcgcctgtga tgtactttct gacatacgcc     720
gataactatg ccattggata cttcaagaag cagggtttct ccaaggagat ctccctcgac     780
agatcggtgt ggatgggata catcaaggat tacgaggag gtactctcat gcagtgctcc      840
atgctgccac gaatcagata ccttgacgtc aacaagattc ttctgctaca gaaggcactg     900
attcacaaga gatccgggc atctccaag agtcatgttg tgcgaaaagg cctcgaccac       960
tttcgtgatt cgaccacgcc agtggacccc atgacgatcc cgggcttgaa ggaggctgga    1020
tggacacctg agatggacga gttggctaga cgaccaaagc gaggtcctca tttttgcagtc   1080
atgcagcacg tgctgtcaga gttgcagaac cacgcttctg cttggccgtt tgcccaggct    1140
gttaaccgag acgaggtgcc cgactactat gaggtcatta aggagcccat ggatctctca    1200
acgatggagc aacgtctcga agctgactct tacaagacca tggaggagtt tgtgtatgac    1260
gctcggttgg tgttcaataa ctgtcgtgct acaacaacg agacgacgac ttactataag    1320
aatgccaaca agctagagaa gttcatggtg gccaaaatca aagagatccc tgagtactct    1380
catttggtgg agtaa                                                    1395
```

<210> SEQ ID NO 68
<211> LENGTH: 464
<212> TYPE: PRT
<213> ORGANISM: Yarrowia lipolytica

<400> SEQUENCE: 68

```
Met Asp Ser Asp Thr Glu Ser Val Lys Arg Arg Lys Ser Ser Gly Ser
1               5                   10                  15

Glu Ser Glu Ser Ser Val Arg Asp Pro Lys Arg Thr Lys Ile Glu Asp
            20                  25                  30

Glu Asp Phe Gln Glu Asn Gly Ile Asp Asp Glu Asp Glu Glu Glu Glu
```

-continued

```
                35                  40                  45
Glu Glu Glu Ala Lys Asp Glu Gly Asp Glu Asp Glu Glu Lys Gly
         50                  55                  60
Glu Asp Asp Glu Glu Asp Glu Glu Lys Glu Gly Glu Asp Gly Glu
 65                  70                  75                  80
Gly Glu Glu Glu Asp Glu Glu Asp Glu Lys Lys Arg Glu Glu
                 85                  90                  95
Glu Glu Lys Tyr Val Thr Ser Phe Asn Phe Asp Gly Val Glu Tyr Lys
            100                 105                 110
Tyr Lys Glu Arg Pro Ala Val Ile Glu Glu Arg Glu Gly Lys Ile Glu
            115                 120                 125
Phe Arg Val Val Asn Asn Asp Asn Ser Lys Glu Asn Leu Met Ile Leu
        130                 135                 140
Thr Gly Leu Lys Asn Ile Phe Gln Lys Gln Leu Pro Lys Met Pro Arg
145                 150                 155                 160
Glu Tyr Ile Ala Arg Leu Val Tyr Asp Arg Ser His Val Ser Met Ala
                165                 170                 175
Val Val Arg Lys Pro Leu Thr Val Val Gly Ile Thr Phe Arg Pro
            180                 185                 190
Phe Asp Thr Arg Lys Phe Ala Glu Ile Val Phe Cys Ala Ile Ser Ser
        195                 200                 205
Thr Glu Gln Val Arg Gly Tyr Gly Ala His Leu Met Asn His Leu Lys
210                 215                 220
Asp Tyr Val Lys Ala Thr Ser Pro Val Met Tyr Phe Leu Thr Tyr Ala
225                 230                 235                 240
Asp Asn Tyr Ala Ile Gly Tyr Phe Lys Lys Gln Gly Phe Ser Lys Glu
                245                 250                 255
Ile Ser Leu Asp Arg Ser Val Trp Met Gly Tyr Ile Lys Asp Tyr Glu
            260                 265                 270
Gly Gly Thr Leu Met Gln Cys Ser Met Leu Pro Arg Ile Arg Tyr Leu
            275                 280                 285
Asp Val Asn Lys Ile Leu Leu Leu Gln Lys Ala Leu Ile His Lys Lys
        290                 295                 300
Ile Arg Ala Ile Ser Lys Ser His Val Val Arg Lys Gly Leu Asp His
305                 310                 315                 320
Phe Arg Asp Ser Thr Thr Pro Val Asp Pro Met Thr Ile Pro Gly Leu
                325                 330                 335
Lys Glu Ala Gly Trp Thr Pro Glu Met Asp Glu Leu Ala Arg Arg Pro
            340                 345                 350
Lys Arg Gly Pro His Phe Ala Val Met Gln His Val Leu Ser Glu Leu
            355                 360                 365
Gln Asn His Ala Ser Ala Trp Pro Phe Ala Gln Ala Val Asn Arg Asp
        370                 375                 380
Glu Val Pro Asp Tyr Tyr Glu Val Ile Lys Glu Pro Met Asp Leu Ser
385                 390                 395                 400
Thr Met Glu Gln Arg Leu Glu Ala Asp Ser Tyr Lys Thr Met Glu Glu
                405                 410                 415
Phe Val Tyr Asp Ala Arg Leu Val Phe Asn Asn Cys Arg Ala Tyr Asn
            420                 425                 430
Asn Glu Thr Thr Thr Tyr Tyr Lys Asn Ala Asn Lys Leu Glu Lys Phe
            435                 440                 445
Met Val Ala Lys Ile Lys Glu Ile Pro Glu Tyr Ser His Leu Val Glu
        450                 455                 460
```

<210> SEQ ID NO 69
<211> LENGTH: 5295
<212> TYPE: DNA
<213> ORGANISM: Candida albicans

<400> SEQUENCE: 69

| | | | | | |
|---|---|---|---|---|---|
| atgccagaaa | catcaattac | tctggattta | gaacatagac | aacaagatga | aattagtagt | 60 |
| atatcatcaa | tttatggtga | tatctttaaa | gatattactc | caacgggttt | agtttggaat | 120 |
| aaaaaaccca | gtccgcattt | ccaagtattt | ttatcatcgt | caaataatcc | tgatcgaccg | 180 |
| actgtttcca | ttacattaga | tatagaattc | actcctactt | atcctttatc | acctccaaaa | 240 |
| gtaaaactac | taaatgctcg | taatttattg | aaaattaata | ttgctaaatt | agaaaagaaa | 300 |
| tgtaaagatt | taatcaaaga | atatcccgaa | caagaagttt | ctttcacgat | aatttccgaa | 360 |
| ttgattttca | tgttagatga | atacaaaca | acaactgaaa | aagtattatc | attagaagaa | 420 |
| gaaagagaat | taagattaag | aaatgaaaga | agggcattag | aagaaaaaga | ggcgaaacag | 480 |
| aagaaggatg | aagaattggc | tcgaaagaaa | caaaataaag | aattgaatga | acaaattcaa | 540 |
| aaaattcaag | gtgaatttga | tgatgatttt | actgatgatc | aagatttaga | tatgtcaact | 600 |
| actaatgata | ataataattc | attaatccca | cttgataaag | atcaattttt | catttttgaa | 660 |
| aatgccatgg | aagcaaccat | tcctaataca | agacggaaat | ttaagtttcg | agcaatactg | 720 |
| ggattcataa | gatataatca | aaaggggtt | ttcaattcaa | ttggatccca | atatattgtt | 780 |
| aaaccattta | ttgataatga | aatccggaat | aaaattgaaa | ataaaggttc | tgatttggca | 840 |
| ttcttattaa | cagtgattga | tttaaccaat | gaatattggc | aaactgacaa | ggggaagcga | 900 |
| gaaattcaag | atttagaatc | ggaattacaa | tcaattatga | gtataaatca | tagtaatata | 960 |
| ttaaaattaa | ttggatttca | aatagataaa | acaaatgttt | ggagagtaag | attgttaacg | 1020 |
| gaattttctc | cagttagtga | aacattatat | gatattctcc | ctactgccga | atttattaat | 1080 |
| tgggcattag | caagaacttg | gcttattcaa | ttattaccag | caatggaata | tcttcataat | 1140 |
| gccggattca | tccataaact | tatatgtccc | atgaccatag | ttatatttca | agagaaggac | 1200 |
| caattgtatt | atcaaaattc | aactaatgaa | ttattaagta | atagtattgg | tggtggtggt | 1260 |
| ggtggtgggg | aagactcatt | aaccatcagt | gctaaaaaag | tgttgaaatt | atgtcatcct | 1320 |
| tcatatgggt | atcgtttatt | agagatgatt | ctgttcacatc | caaatgaggg | agaaacatta | 1380 |
| gatcgatctc | cacaagtaaa | tccaccagca | tggttagcac | cagaattgaa | aacttctggg | 1440 |
| tatcattaca | aatctgatat | ttgggattta | ggagtacttt | tcttaagagt | aatgttagga | 1500 |
| tttgatattt | taaacaccac | ataccataca | cctagtgatt | ttataaataa | attttccgtt | 1560 |
| aaagattttg | ttggagcaga | agaatatgct | tcattagtgt | atgatgtatt | atcgaaaatg | 1620 |
| ttacaagtta | aattatcaaa | acgaccatct | cctttggaat | aaatgccgt | aaaattttta | 1680 |
| cgagatggtc | ccataatttc | aaaattacaa | tcggaaacta | acttatcacg | aatgaaaaaa | 1740 |
| aatgtcgaaa | ctgatttggt | atcatcaacc | aatacaagac | atgttcaaat | acaaggacat | 1800 |
| gaacaggatt | cgactgcaac | aacaaaacat | ttgaatattt | atcatcaaaa | tatttcacgc | 1860 |
| agacggttat | ctaaccagaa | tactcaacat | ccatattttg | gtgaaaattc | tagtcttatc | 1920 |
| atgccttcag | ggtcacaacg | aaatatgggg | agatacgcca | gagattttga | agaaatttgg | 1980 |
| aaattgggtc | gtggtggatt | tggtgaagtt | gttaaagcta | gaagtagaat | ggaagggata | 2040 |
| ttttatgctg | tgaaaaaaat | taaacatcga | gctgataaat | tggattcttt | attaagtgaa | 2100 |

```
gttttatctt tagctagatt gaaccatcaa tatattgttc gttattatgg tacttgggtt    2160
gaagaattag aagatacatc tgcgattcca tccaatagca catctgctat tgcgagcgat    2220
gacgaagagg aggaagagga ggaagatgac acagaaggcg actttggtga tgatgatctt    2280
gaactgacat tttcaagtcg tgttggtcgt tcatcatctg tgttacctag ttatgataac    2340
tcatttcaag tcgattacat ttcaacatct tttgacccta ggatagaatt tgatgaaagt    2400
tcagaagaag atgaccaaaa tgaagatgat gatccgtttg tgtttgccaa ttcaactgat    2460
gatatctcaa ataatgaaac agaagatcgt tccaaaagtg attcgaaaga gtttctgtt     2520 aaaaaaccaa aagatgttgt taactcctct aaaaatgcat caccgaaatc aatattatat    2580
atacaaatgg agttttgtga aaataatacc cttctcaatc ttattgaaca aggattacct    2640
aataaccctg atgaatattg gagactttc cgacaattac ttgaagcagt ttcatatatt     2700
catcgtgaag gatttattca tcgtgattta aaaccaatga atattttcat tgatagatcc    2760
aataatatta agttgggga tttcggatta gctaaaaatt cacaattttc ttcagttgtt    2820
ctgacgaata atcaagtgga agctaaagat aatgaattat ctaccgtggt gggaacatta    2880
ttttatactg ccaatgaagt ggccacgggt caatacgatg aaaagttga tatgtattca    2940 cttggaataa ttttctttga aatgtgttat cctcttgcca cgggtatgca aagagctaaa    3000
acattaaatg atttacgatt gaaatcagtt gaattcccta caaatttcat tgctagtaaa    3060
tataaaactg aaaaaaaaat tattcgatta ttattagatc atgatcctaa aattcgtcct    3120
agtgcagcac aacttttaca aagtggttgg ttacccgttg aacatcaaga tcaagttatt    3180
caagaagcat taaaatcttt agctgatcca gcatctcctt ggcaacaaca agttcgtgaa    3240
gcattgttca atcaaccgta tctgcttgct aaagatttaa tgtttgataa acaaaatgaa    3300
cataattccc ataataagca tgttgaattg gatacttcga atgattattt attatttgat    3360
aaaatcatga agaattgac caagatttc actaatcatg gagccattga gaaatttaaat    3420 acaaatttag ttttaccaaa ggcaccttca caatcaagag aattagttta tgattttttg    3480
gatagaagtg gtgcagtttt aactttacct tatgatttga ctttaccaac agcaagattt    3540
ttaagtaaaa ccgatatgac aattcctaaa acttttcgac acgaatttgt ctatcgacct    3600
aatgttcgag gtattggtat acctgatcgt tatagtgccg ttaattttga tatagccggt    3660
ggactggaag ttaacaaggc aacacttttc gctcatgatg ctgaatgttt aaaagtgatt    3720
gatgaaattg tcaatacttt accatgtttt aaaaatacca ttattgttat taatcattat    3780
gatattttgg atgctgttgt ttcatttct tttggtaata ttggaattga tgataagaaa    3840
aaattagata ttttttggagt attatcacaa ttgggaattg ataaatcacc cgatgaaata    3900
aaacgttact tgagggaaga ttttcaagta ccacatactg ttactaaaga tcttgttgaa    3960
aatttcaatt ttacatgtga agtggaacgg gcaagacaaa aattacaaaa attaatggtt    4020
gattctcccc cattattaaa agttgaacga gcatatactt atttaattga agtggttaaa    4080
attttgaaac acacgaatat taaaacatca atgattttca atccattgag taattataat    4140
agtaaatatt atatccatgg aataatgttt caagcagttt ttaaacctga tagatccaaa    4200
cgttatacta gagtagttac tggtggacga tatgattcat taattgaatc ttttttcaaat    4260 gtcaccacaa caactaaaca aatcactcct catggtgttg gattttcatt gactactagt    4320 ttactttca ttcttatgaa aacattaatt tctcgaggga atctaaatt ggatcttgta     4380 aataaatgga agggcaatcg atgtaaagta cttataagtt ctactcaaca acaatttta    4440 agtcaagtgg gatatcaatt agtttctaaa ttttggaata aaaacataag tgctgatata    4500
```

| | | |
|---|---|---|
| acatcagttg cagcaaagac tcaagatgaa atattccaaa atggtaattc agaagggct | 4560 | |
| atatggatag ttataatacg actgttacct acaacaattg ggaattcatt ctcatctttg | 4620 | |
| aatggtggta gtggtggtag tagtagtagt actactacta ctagcactag cattagaaga | 4680 | |
| agtaaaaaat ctggatctgg atttaaacct ttgaaattga gaatataat tactggtaaa | 4740 | |
| gatattgatt tagattatga tgaagtgata gattatttgg tgactgaatt attagaagat | 4800 | |
| tcagaacatg aagaaaatga tcaagataat ggtacgatga caaactcaac aacattactt | 4860 | |
| acatcatcat cattatcttc taaaacaaat caagaagaag aattattaaa tggaccaatt | 4920 | |
| gattcagttg aaattgatca aaaaatcatt gttgttaaaa atgatgctcc tcgtagtagg | 4980 | |
| aaaaataaac gagataaatg ggaatcagaa aatgatgcta aattagctgg acaacaatgt | 5040 | |
| ataaaaaatt taagtggtgg acctgttgtt gttattgatg ctagagatga aatattagat | 5100 | |
| atgattagta ttacttcaat tcatcaacaa gatgaatgga ttagaaaagt ggtttataca | 5160 | |
| actaataatt tcccaaaaag ttttgctatg aatatttata atactttgat taaagaatttt | 5220 | |
| aataaaggtt caatttggtg tatttttggtg tcttcaagaa ctcaacatac aactattgtt | 5280 | |
| gatctacgtc gataa | 5295 | |

<210> SEQ ID NO 70
<211> LENGTH: 1764
<212> TYPE: PRT
<213> ORGANISM: Candida albicans

<400> SEQUENCE: 70

```
Met Pro Glu Thr Ser Ile Thr Ser Asp Leu Glu His Arg Gln Gln Asp
1               5                   10                  15

Glu Ile Ser Ser Ile Ser Ser Ile Tyr Gly Asp Ile Phe Lys Asp Ile
            20                  25                  30

Thr Pro Thr Gly Leu Val Trp Asn Lys Lys Pro Ser Pro His Phe Gln
        35                  40                  45

Val Phe Leu Ser Ser Ser Asn Asn Pro Asp Arg Pro Thr Val Ser Ile
    50                  55                  60

Thr Leu Asp Ile Glu Phe Thr Pro Thr Tyr Pro Leu Ser Pro Pro Lys
65                  70                  75                  80

Val Lys Leu Leu Asn Ala Arg Asn Leu Leu Lys Ile Asn Ile Ala Lys
                85                  90                  95

Leu Glu Lys Lys Cys Lys Asp Leu Ile Lys Glu Tyr Pro Glu Gln Glu
            100                 105                 110

Val Ser Phe Thr Ile Ile Ser Glu Leu Ile Phe Met Leu Asp Glu Ile
        115                 120                 125

Gln Thr Thr Thr Glu Lys Val Leu Ser Leu Glu Glu Arg Glu Leu
    130                 135                 140

Arg Leu Arg Asn Glu Arg Arg Ala Leu Glu Glu Lys Glu Ala Lys Gln
145                 150                 155                 160

Lys Lys Asp Glu Glu Leu Ala Arg Lys Lys Gln Asn Lys Glu Leu Asn
                165                 170                 175

Glu Gln Ile Gln Lys Ile Gln Gly Glu Phe Asp Asp Phe Thr Asp
            180                 185                 190

Asp Gln Asp Leu Asp Met Ser Thr Thr Asn Asp Asn Asn Ser Leu
        195                 200                 205

Ile Pro Leu Asp Lys Asp Gln Phe Phe Ile Phe Glu Asn Ala Met Glu
    210                 215                 220
```

```
Ala Thr Ile Pro Asn Thr Arg Arg Lys Phe Lys Phe Arg Ala Ile Ser
225                 230                 235                 240

Gly Phe Ile Arg Tyr Asn Gln Lys Gly Val Phe Asn Ser Ile Gly Ser
            245                 250                 255

Gln Tyr Ile Val Lys Pro Phe Ile Asp Asn Glu Ile Arg Asn Lys Ile
        260                 265                 270

Glu Asn Lys Gly Ser Asp Leu Ala Phe Leu Leu Thr Val Ile Asp Leu
    275                 280                 285

Thr Asn Glu Tyr Trp Gln Thr Asp Lys Gly Lys Arg Glu Ile Gln Asp
290                 295                 300

Leu Glu Ser Glu Leu Gln Ser Ile Met Ser Ile Asn His Ser Asn Ile
305                 310                 315                 320

Leu Lys Leu Ile Gly Phe Gln Ile Asp Lys Thr Asn Val Trp Arg Val
                325                 330                 335

Arg Leu Leu Thr Glu Phe Ser Pro Val Ser Glu Thr Leu Tyr Asp Ile
            340                 345                 350

Leu Pro Thr Ala Glu Phe Ile Asn Trp Ala Leu Ala Arg Thr Trp Leu
        355                 360                 365

Ile Gln Leu Leu Pro Ala Met Glu Tyr Leu His Asn Ala Gly Phe Ile
    370                 375                 380

His Lys Leu Ile Cys Pro Met Thr Ile Val Ile Phe Gln Glu Lys Asp
385                 390                 395                 400

Gln Leu Tyr Tyr Gln Asn Ser Thr Asn Glu Leu Leu Ser Asn Ser Ile
                405                 410                 415

Gly Gly Gly Gly Gly Gly Glu Asp Ser Leu Thr Ile Ser Ala Lys
            420                 425                 430

Lys Val Leu Lys Leu Cys His Pro Ser Tyr Gly Tyr Arg Leu Leu Glu
        435                 440                 445

Met Ile Ser Leu His Pro Asn Glu Gly Glu Thr Leu Asp Arg Ser Pro
450                 455                 460

Gln Val Asn Pro Pro Ala Trp Leu Ala Pro Glu Leu Lys Thr Ser Gly
465                 470                 475                 480

Tyr His Tyr Lys Ser Asp Ile Trp Asp Leu Gly Val Leu Phe Leu Arg
                485                 490                 495

Val Met Leu Gly Phe Asp Ile Leu Asn Thr Thr Tyr His Thr Pro Ser
            500                 505                 510

Asp Phe Ile Asn Lys Phe Ser Val Lys Asp Phe Val Gly Ala Glu Glu
        515                 520                 525

Tyr Ala Ser Leu Val Tyr Asp Val Leu Ser Lys Met Leu Gln Val Lys
530                 535                 540

Leu Ser Lys Arg Pro Ser Pro Leu Glu Leu Asn Ala Val Lys Phe Leu
545                 550                 555                 560

Arg Asp Gly Pro Ile Ile Ser Lys Leu Gln Ser Glu Thr Asn Leu Ser
                565                 570                 575

Arg Met Lys Lys Asn Val Glu Thr Asp Leu Val Ser Ser Thr Asn Thr
            580                 585                 590

Arg His Val Gln Ile Gln Gly His Glu Gln Asp Ser Thr Ala Thr Thr
        595                 600                 605

Lys His Leu Asn Ile Tyr His Gln Asn Ile Ser Arg Arg Leu Ser
610                 615                 620

Asn Gln Asn Thr Gln His Pro Tyr Phe Gly Glu Asn Ser Ser Leu Ile
625                 630                 635                 640

Met Pro Ser Gly Ser Gln Arg Asn Met Gly Arg Tyr Ala Arg Asp Phe
```

-continued

```
            645                 650                 655
Glu Glu Ile Gly Lys Leu Gly Arg Gly Gly Phe Gly Glu Val Val Lys
                660                 665                 670
Ala Arg Ser Arg Met Glu Gly Ile Phe Tyr Ala Val Lys Lys Ile Lys
            675                 680                 685
His Arg Ala Asp Lys Leu Asp Ser Leu Leu Ser Glu Val Leu Ser Leu
        690                 695                 700
Ala Arg Leu Asn His Gln Tyr Ile Val Arg Tyr Tyr Gly Thr Trp Val
705                 710                 715                 720
Glu Glu Leu Glu Asp Thr Ser Ala Ile Pro Ser Asn Ser Thr Ser Ala
                725                 730                 735
Ile Ala Ser Asp Asp Glu Glu Glu Glu Glu Glu Asp Asp Thr Glu
            740                 745                 750
Gly Asp Phe Gly Asp Asp Leu Glu Ser Thr Phe Ser Ser Arg Val
        755                 760                 765
Gly Arg Ser Ser Ser Val Leu Pro Ser Tyr Asp Asn Ser Phe Gln Val
        770                 775                 780
Asp Tyr Ile Ser Thr Ser Phe Asp Pro Arg Ile Glu Phe Asp Glu Ser
785                 790                 795                 800
Ser Glu Glu Asp Asp Gln Asn Glu Asp Asp Pro Phe Val Phe Ala
                805                 810                 815
Asn Ser Thr Asp Asp Ile Ser Asn Asn Glu Thr Glu Asp Arg Ser Lys
            820                 825                 830
Ser Asp Ser Lys Glu Val Ser Val Lys Lys Pro Lys Asp Val Val Asn
        835                 840                 845
Ser Ser Lys Asn Ala Ser Pro Lys Ser Ile Leu Tyr Ile Gln Met Glu
    850                 855                 860
Phe Cys Glu Asn Asn Thr Leu Leu Asn Leu Ile Glu Gln Gly Leu Pro
865                 870                 875                 880
Asn Asn Pro Asp Glu Tyr Trp Arg Leu Phe Arg Gln Leu Leu Glu Ala
                885                 890                 895
Val Ser Tyr Ile His Arg Glu Gly Phe Ile His Arg Asp Leu Lys Pro
            900                 905                 910
Met Asn Ile Phe Ile Asp Arg Ser Asn Asn Ile Lys Val Gly Asp Phe
        915                 920                 925
Gly Leu Ala Lys Asn Ser Gln Phe Ser Ser Val Ser Thr Asn Asn
    930                 935                 940
Gln Val Glu Ala Lys Asp Asn Glu Leu Ser Thr Val Val Gly Thr Leu
945                 950                 955                 960
Phe Tyr Thr Ala Asn Glu Val Ala Thr Gly Gln Tyr Asp Glu Lys Val
                965                 970                 975
Asp Met Tyr Ser Leu Gly Ile Ile Phe Phe Glu Met Cys Tyr Pro Leu
            980                 985                 990
Ala Thr Gly Met Gln Arg Ala Lys  Thr Leu Asn Asp Leu  Arg Leu Lys
        995                 1000                1005
Ser Val Glu Phe Pro Thr Asn  Phe Ile Ala Ser Lys  Tyr Lys Thr
    1010                1015                1020
Glu Lys Lys Ile Ile Arg Leu  Leu Leu Asp His Asp  Pro Lys Ile
    1025                1030                1035
Arg Pro Ser Ala Ala Gln Leu  Leu Gln Ser Gly Trp  Leu Pro Val
    1040                1045                1050
Glu His  Gln Asp Gln Val Ile  Gln Glu Ala Leu Lys  Ser Leu Ala
    1055                1060                1065
```

-continued

Asp Pro Ala Ser Pro Trp Gln Gln Val Arg Glu Ala Leu Phe
    1070            1075            1080

Asn Gln Pro Tyr Ser Leu Ala Lys Asp Leu Met Phe Asp Lys Gln
    1085            1090            1095

Asn Glu His Asn Ser His Asn Lys His Val Glu Leu Asp Thr Ser
    1100            1105            1110

Asn Asp Tyr Leu Leu Phe Asp Lys Ile Met Lys Glu Leu Thr Lys
    1115            1120            1125

Ile Phe Thr Asn His Gly Ala Ile Glu Asn Leu Asn Thr Asn Leu
    1130            1135            1140

Val Leu Pro Lys Ala Pro Ser Gln Ser Arg Glu Leu Val Tyr Asp
    1145            1150            1155

Phe Leu Asp Arg Ser Gly Ala Val Leu Thr Leu Pro Tyr Asp Leu
    1160            1165            1170

Thr Leu Pro Thr Ala Arg Phe Leu Ser Lys Thr Asp Met Thr Ile
    1175            1180            1185

Pro Lys Thr Phe Arg His Glu Phe Val Tyr Arg Pro Asn Val Arg
    1190            1195            1200

Gly Ile Gly Ile Pro Asp Arg Tyr Ser Ala Val Asn Phe Asp Ile
    1205            1210            1215

Ala Gly Gly Ser Glu Val Asn Lys Ala Thr Leu Phe Ala His Asp
    1220            1225            1230

Ala Glu Cys Leu Lys Val Ile Asp Glu Ile Val Asn Thr Leu Pro
    1235            1240            1245

Cys Phe Lys Asn Thr Ile Ile Val Ile Asn His Tyr Asp Ile Leu
    1250            1255            1260

Asp Ala Val Val Ser Phe Ser Phe Gly Asn Ile Gly Ile Asp Asp
    1265            1270            1275

Lys Lys Lys Leu Asp Ile Phe Gly Val Leu Ser Gln Leu Gly Ile
    1280            1285            1290

Asp Lys Ser Pro Asp Glu Ile Lys Arg Tyr Leu Arg Glu Asp Phe
    1295            1300            1305

Gln Val Pro His Thr Val Thr Lys Asp Leu Val Glu Asn Phe Asn
    1310            1315            1320

Phe Thr Cys Glu Val Glu Arg Ala Arg Gln Lys Leu Gln Lys Leu
    1325            1330            1335

Met Val Asp Ser Pro Pro Leu Leu Lys Val Glu Arg Ala Tyr Thr
    1340            1345            1350

Tyr Leu Ile Glu Val Val Lys Ile Leu Lys His Thr Asn Ile Lys
    1355            1360            1365

Thr Ser Met Ile Phe Asn Pro Leu Ser Asn Tyr Asn Ser Lys Tyr
    1370            1375            1380

Tyr Ile His Gly Ile Met Phe Gln Ala Val Phe Lys Pro Asp Arg
    1385            1390            1395

Ser Lys Arg Tyr Thr Arg Val Val Thr Gly Gly Arg Tyr Asp Ser
    1400            1405            1410

Leu Ile Glu Ser Phe Ser Asn Val Thr Thr Thr Lys Gln Ile
    1415            1420            1425

Thr Pro His Gly Val Gly Phe Ser Leu Thr Thr Ser Leu Leu Phe
    1430            1435            1440

Ile Leu Met Lys Thr Leu Ile Ser Arg Gly Lys Ser Lys Leu Asp
    1445            1450            1455

| | | | | | | | | | | |
|---|---|---|---|---|---|---|---|---|---|---|
| Leu | Val | Asn | Lys | Trp | Lys | Gly | Asn | Arg | Cys | Lys | Val | Leu | Ile | Ser |
| | 1460 | | | | 1465 | | | | 1470 | | | |
| Ser | Thr | Gln | Gln | Gln | Phe | Leu | Ser | Gln | Val | Gly | Tyr | Gln | Leu | Val |
| 1475 | | | | | 1480 | | | | | 1485 | | | | |
| Ser | Lys | Phe | Trp | Asn | Lys | Asn | Ile | Ser | Ala | Asp | Ile | Thr | Ser | Val |
| | 1490 | | | | | 1495 | | | | | 1500 | | | |
| Ala | Ala | Lys | Thr | Gln | Asp | Glu | Ile | Phe | Gln | Asn | Gly | Asn | Ser | Glu |
| 1505 | | | | | 1510 | | | | | 1515 | | | | |
| Gly | Ala | Ile | Trp | Ile | Val | Ile | Ile | Arg | Ser | Leu | Pro | Thr | Thr | Ile |
| | 1520 | | | | | 1525 | | | | | 1530 | | | |
| Gly | Asn | Ser | Phe | Ser | Ser | Leu | Asn | Gly | Gly | Ser | Gly | Gly | Ser | Ser |
| 1535 | | | | | 1540 | | | | | 1545 | | | | |
| Ser | Ser | Thr | Thr | Thr | Thr | Ser | Thr | Ser | Ile | Arg | Arg | Ser | Lys | Lys |
| 1550 | | | | | | 1555 | | | | | 1560 | | | |
| Ser | Gly | Ser | Gly | Phe | Lys | Pro | Leu | Lys | Leu | Arg | Asn | Ile | Ile | Thr |
| 1565 | | | | | 1570 | | | | | 1575 | | | | |
| Gly | Lys | Asp | Ile | Asp | Leu | Asp | Tyr | Asp | Glu | Val | Ile | Asp | Tyr | Leu |
| 1580 | | | | | 1585 | | | | | 1590 | | | | |
| Val | Thr | Glu | Leu | Leu | Glu | Asp | Ser | Glu | His | Glu | Asn | Asp | Gln |
| 1595 | | | | | 1600 | | | | | 1605 | | | |
| Asp | Asn | Gly | Thr | Met | Thr | Asn | Ser | Thr | Thr | Leu | Leu | Thr | Ser | Ser |
| 1610 | | | | | 1615 | | | | | 1620 | | | | |
| Ser | Leu | Ser | Ser | Lys | Thr | Asn | Gln | Glu | Glu | Glu | Leu | Leu | Asn | Gly |
| | 1625 | | | | | 1630 | | | | | 1635 | | | |
| Pro | Ile | Asp | Ser | Val | Glu | Ile | Asp | Gln | Lys | Ile | Ile | Val | Val | Lys |
| 1640 | | | | | 1645 | | | | | 1650 | | | | |
| Asn | Asp | Ala | Pro | Arg | Ser | Arg | Lys | Asn | Lys | Arg | Asp | Lys | Trp | Glu |
| 1655 | | | | | 1660 | | | | | 1665 | | | | |
| Ser | Glu | Asn | Asp | Ala | Lys | Leu | Ala | Gly | Gln | Gln | Cys | Ile | Lys | Asn |
| 1670 | | | | | 1675 | | | | | 1680 | | | | |
| Leu | Ser | Gly | Gly | Pro | Val | Val | Val | Ile | Asp | Ala | Arg | Asp | Glu | Ile |
| | 1685 | | | | | 1690 | | | | | 1695 | | | |
| Leu | Asp | Met | Ile | Ser | Ile | Thr | Ser | Ile | His | Gln | Gln | Asp | Glu | Trp |
| 1700 | | | | | 1705 | | | | | 1710 | | | | |
| Ile | Arg | Lys | Val | Val | Tyr | Thr | Thr | Asn | Asn | Phe | Pro | Lys | Ser | Phe |
| 1715 | | | | | 1720 | | | | | 1725 | | | | |
| Ala | Met | Asn | Ile | Tyr | Asn | Thr | Leu | Ile | Lys | Glu | Phe | Asn | Lys | Gly |
| 1730 | | | | | 1735 | | | | | 1740 | | | | |
| Ser | Ile | Trp | Cys | Ile | Leu | Val | Ser | Ser | Arg | Thr | Gln | His | Thr | Thr |
| | 1745 | | | | | 1750 | | | | | 1755 | | | |
| Ile | Val | Asp | Leu | Arg | Arg |
| | 1760 | | | | |

<210> SEQ ID NO 71
<211> LENGTH: 936
<212> TYPE: DNA
<213> ORGANISM: Candida albicans

<400> SEQUENCE: 71

```
atggctgatt tgacattaa ggaaacgtat cttaagtttt tagaagaaga caaagatatg    60
actatgccta tcgcggcaat tgagtcactt gtgtcaatgt taaaagcaaa gtcaccatca   120
acttcctccg aattaatcaa tttagtttcg aaaaatattg atttattaaa gtcttcaatt   180
cccaacaata tttctctttc tgctgggtgt gatttattta tgagatttgt gttgagaaac   240
```

```
actaatgtat attctgattg ggagtcattt tcacagaatc ttgttgagaa tggagaattg    300
tttgttcaac gtgctaagga atcaagactt aaactggcag aatacggtgt tccatttatc    360
aaggatgacg atgtaatatt agttcattca tattcacgtg tcgtttacag tctattgttg    420
aaggctaaac aggagaagct aattcgattc aaagttttgg ttaccgagag tagaccaaca    480
ggaaatggat actacatggc taggaaattg aaagaggcag acaccggt tgaggttatt    540 gtagataacg cagtgggata tgttttgcat aaagtagaca aaatcttggt tggtgccgaa    600
ggggtcgctg aaagtggtgg agtaataaat cacattggaa cgtatcaaat tggctgttta    660
gctaaagtca acaataagcc tttctatgtc gtgaccgagt ctcacaaatt tgtcagattg    720
tttcccttgg cacctaatga cctacctaac agcattagtc atttcgatta tgacgaaaac    780
agaaccgaag agctcaacca cagtggacaa gaacttttcg aaaccaggtt tgttgatttc    840
acacctcatg aatacattac tgctttgata acagatttgg gagtattgac tccatctgca    900
gtcagtgaag agttgataaa aatatggtac gattga                              936
```

<210> SEQ ID NO 72
<211> LENGTH: 311
<212> TYPE: PRT
<213> ORGANISM: Candida albicans

<400> SEQUENCE: 72

```
Met Ala Asp Phe Asp Ile Lys Glu Thr Tyr Leu Lys Phe Leu Glu Glu
1               5                   10                  15

Asp Lys Asp Met Thr Met Pro Ile Ala Ala Ile Glu Ser Leu Val Ser
            20                  25                  30

Met Leu Lys Ala Lys Ser Pro Ser Thr Ser Ser Glu Leu Ile Asn Leu
        35                  40                  45

Val Ser Lys Asn Ile Asp Leu Leu Lys Ser Ser Ile Pro Asn Asn Ile
    50                  55                  60

Ser Leu Ser Ala Gly Cys Asp Leu Phe Met Arg Phe Val Leu Arg Asn
65                  70                  75                  80

Thr Asn Val Tyr Ser Asp Trp Glu Ser Phe Ser Gln Asn Leu Val Glu
                85                  90                  95

Asn Gly Glu Leu Phe Val Gln Arg Ala Lys Glu Ser Arg Leu Lys Ser
            100                 105                 110

Ala Glu Tyr Gly Val Pro Phe Ile Lys Asp Asp Val Ile Leu Val
        115                 120                 125

His Ser Tyr Ser Arg Val Val Tyr Ser Leu Leu Leu Lys Ala Lys Gln
    130                 135                 140

Glu Lys Leu Ile Arg Phe Lys Val Leu Val Thr Glu Ser Arg Pro Thr
145                 150                 155                 160

Gly Asn Gly Tyr Tyr Met Ala Arg Lys Leu Lys Glu Ala Asp Ile Pro
                165                 170                 175

Val Glu Val Ile Val Asp Asn Ala Val Gly Tyr Val Leu His Lys Val
            180                 185                 190

Asp Lys Ile Leu Val Gly Ala Glu Gly Val Ala Glu Ser Gly Gly Val
        195                 200                 205

Ile Asn His Ile Gly Thr Tyr Gln Ile Gly Cys Leu Ala Lys Val Asn
    210                 215                 220

Asn Lys Pro Phe Tyr Val Val Thr Glu Ser His Lys Phe Val Arg Leu
225                 230                 235                 240

Phe Pro Leu Ala Pro Asn Asp Leu Pro Asn Ser Ile Ser His Phe Asp
                245                 250                 255
```

Tyr Asp Glu Asn Arg Thr Glu Leu Asn His Ser Gly Gln Glu Leu
            260                 265                 270

Phe Glu Thr Arg Phe Val Asp Phe Thr Pro His Glu Tyr Ile Thr Ala
        275                 280                 285

Leu Ile Thr Asp Leu Gly Val Leu Thr Pro Ser Ala Val Ser Glu Glu
    290                 295                 300

Leu Ile Lys Ile Trp Tyr Asp
305                 310

<210> SEQ ID NO 73
<211> LENGTH: 1350
<212> TYPE: DNA
<213> ORGANISM: Candida albicans

<400> SEQUENCE: 73

```
atggttgaca gaaaagaac tgcagcaata cgtgccgagg atgatgatga agaaaatgac      60
aatgttcctt tacagaaaaa agtgaaaata gaagcaaagc agaagaaga agaggaagat     120
ggtgataagt caggagccac ggaaaccaaa tctgaggtga acaagaatc aaagaagaa      180
actactcaaa aggaaaataa tgaagaggac gaggaagagg aagaagagga agatgacgaa    240
gaagccgaag aagagaagaa aagaataacc aatttcaatt ttgatggcga aatttacaca    300
ttcaaggaaa gaccttcggt aattgaagaa aagaaggca aatagagtt cgtgtggtg      360
aataatgaca atagtcgaga aaacttgatt gtgctaaccg ggttaaagaa tattttccaa    420
aagcaactac ccaagatgcc tcgtgaatat atctcgcgtt tggtgtatga tcgatcacat    480
ttgtcaatgg cagttgtgag aaagccatta actgtggtag gtgggatcac ataccgtcca    540
tttaacaacc gtggatttgc cgaaattgtg ttttgtgcta tctcgtcaac tgaacaagtg    600
cgtgggtatg gtgcacattt gatgaatcat ttgaaagact atgtgagggc aacatctcca    660
atcaaatatt tcttgacgta tgcagataac tatgctattg gtatttcaa aaagcagggt    720
ttcacgaagg aaatatcatt agataaatcg gtgtggatgg ggtacatcaa ggattacgaa    780
ggtggtacat tgatgcagtg ctcgatgtta ccgtcaatat taaggtacct tgatctgggt    840
aaaatattac ttttgcaaaa agctgctatt gaaagaaaaa tacggtctag atctaaatca    900
aaaatagtga gaccgggttt gcaagttttt aaaaccaata gaatgtgac attagacccc    960
aaagatatcc ctggattagc agaggcaggg tggctgaag aatggataa attagcacaa   1020
aaaccgaaaa gaggaccaca ttataacttt atggttacgc tattcagtga aattcagaac   1080
cacccttctg cttggccatt tgcagtggca gtcaacaaag aagaagtacc agattattat   1140
cgagttattg aacatccaat tgatttggca acaatagaac aaaaattgga aaacaacttg   1200
tatttaaaat ttactgattt tgtggatgat ctaaaactaa tgttcaacaa ttgtcgagct   1260
tataattcgg aaaccacaac atattataaa aacgcaaata aactagaaaa gtttatgaat   1320
aataaattga aagactgtag ttttgtatag                                    1350
```

<210> SEQ ID NO 74
<211> LENGTH: 449
<212> TYPE: PRT
<213> ORGANISM: Candida albicans

<400> SEQUENCE: 74

Met Val Asp Arg Lys Arg Thr Ala Ala Ile Arg Ala Glu Asp Asp
1               5                   10                  15

Glu Glu Asn Asp Asn Val Pro Leu Gln Lys Lys Val Lys Ile Glu Ala

-continued

```
                20                  25                  30
Lys Gln Lys Glu Glu Glu Asp Gly Asp Lys Ser Gly Ala Thr Glu
            35                  40                  45
Thr Lys Ser Glu Val Lys Gln Glu Ser Lys Glu Thr Thr Gln Lys
        50                  55                  60
Glu Asn Asn Glu Glu Asp Glu Glu Glu Glu Glu Asp Asp Glu
65                  70                  75                  80
Glu Ala Glu Glu Lys Lys Arg Ile Thr Asn Phe Asn Phe Asp Gly
                85                  90                  95
Glu Ile Tyr Thr Phe Lys Glu Arg Pro Ser Val Ile Glu Glu Lys Glu
            100                 105                 110
Gly Lys Ile Glu Phe Arg Val Val Asn Asn Asp Asn Ser Arg Glu Asn
        115                 120                 125
Leu Ile Val Leu Thr Gly Leu Lys Asn Ile Phe Gln Lys Gln Leu Pro
    130                 135                 140
Lys Met Pro Arg Glu Tyr Ile Ser Arg Leu Val Tyr Asp Arg Ser His
145                 150                 155                 160
Leu Ser Met Ala Val Val Arg Lys Pro Leu Thr Val Val Gly Gly Ile
                165                 170                 175
Thr Tyr Arg Pro Phe Asn Asn Arg Gly Phe Ala Glu Ile Val Phe Cys
            180                 185                 190
Ala Ile Ser Ser Thr Glu Gln Val Arg Gly Tyr Gly Ala His Leu Met
        195                 200                 205
Asn His Leu Lys Asp Tyr Val Arg Ala Thr Ser Pro Ile Lys Tyr Phe
    210                 215                 220
Leu Thr Tyr Ala Asp Asn Tyr Ala Ile Gly Tyr Phe Lys Lys Gln Gly
225                 230                 235                 240
Phe Thr Lys Glu Ile Ser Leu Asp Lys Ser Val Trp Met Gly Tyr Ile
                245                 250                 255
Lys Asp Tyr Glu Gly Gly Thr Leu Met Gln Cys Ser Met Leu Pro Ser
            260                 265                 270
Ile Leu Arg Tyr Leu Asp Ser Gly Lys Ile Leu Leu Gln Lys Ala
        275                 280                 285
Ala Ile Glu Arg Lys Ile Arg Ser Arg Ser Lys Ser Lys Ile Val Arg
    290                 295                 300
Pro Gly Leu Gln Val Phe Lys Thr Asn Lys Asn Val Thr Leu Asp Pro
305                 310                 315                 320
Lys Asp Ile Pro Gly Leu Ala Glu Ala Gly Trp Ser Glu Glu Met Asp
                325                 330                 335
Lys Leu Ala Gln Lys Pro Lys Arg Gly Pro His Tyr Asn Phe Met Val
            340                 345                 350
Thr Leu Phe Ser Glu Ile Gln Asn His Pro Ser Ala Trp Pro Phe Ala
        355                 360                 365
Val Ala Val Asn Lys Glu Glu Val Pro Asp Tyr Tyr Arg Val Ile Glu
    370                 375                 380
His Pro Ile Asp Leu Ala Thr Ile Glu Gln Lys Leu Glu Asn Asn Leu
385                 390                 395                 400
Tyr Leu Lys Phe Thr Asp Phe Val Asp Asp Leu Lys Leu Met Phe Asn
                405                 410                 415
Asn Cys Arg Ala Tyr Asn Ser Glu Thr Thr Thr Tyr Tyr Lys Asn Ala
            420                 425                 430
Asn Lys Leu Glu Lys Phe Met Asn Asn Lys Leu Lys Asp Cys Ser Phe
        435                 440                 445
```

Val

<210> SEQ ID NO 75
<211> LENGTH: 1350
<212> TYPE: DNA
<213> ORGANISM: Candida albicans

<400> SEQUENCE: 75

| | | | | | |
|---|---|---|---|---|---|
| atggttgaca | gaaaagaac | tgcagcaata | cgtgccgagg | atgatgatga | agaaaatgac | 60 |
| aatgttcctt | tacagaaaaa | agtgaaaata | gaagcaaagc | agaaagaaga | agaggaagat | 120 |
| ggtgataagt | caggagccac | ggaaaccaaa | tctgaggtga | acaagaatc | aaaagaagaa | 180 |
| actactcaaa | aggaaaataa | tgaagaggac | gaggaagagg | aagaagagga | agatgacgaa | 240 |
| gaagccgaag | aagagaagaa | aagaataacc | aatttcaatt | ttgatggcga | aatttacaca | 300 |
| ttcaaggaaa | gaccttcggt | aattgaagaa | aaagaaggca | aaatagagtt | tcgtgtggtg | 360 |
| aataatgaca | atagtcgaga | aaacttgatt | gtgctaaccg | ggttaaagaa | tatttttccaa | 420 |
| aagcaactac | ccaagatgcc | tcgtgaatat | atctcgcgtt | tggtgtatga | tcgatcacat | 480 |
| ttgtcaatgg | cagttgtgag | aaagccatta | actgtggtag | gtgggatcac | ataccgtcca | 540 |
| tttaacaacc | gtggatttgc | cgaaattgtg | ttttgtgcta | tctcgtcaac | tgaacaagtg | 600 |
| cgtgggtatg | gtgcacattt | gatgaatcat | ttgaaagact | atgtgagggc | aacatctcca | 660 |
| atcaaatatt | tcttgacgta | tgcagataac | tatgctattg | ggtatttcaa | aaagcagggt | 720 |
| ttcacgaagg | aaatatcatt | agataaatcg | gtgtggatgg | ggtacatcaa | ggattacgaa | 780 |
| ggtggtacat | tgatgcagtg | ctcgatgtta | ccgtcaatat | taaggtacct | tgatctgggt | 840 |
| aaaatattac | ttttgcaaaa | agctgctatt | gaaagaaaaa | tacggtctag | atctaaatca | 900 |
| aaaatagtga | gaccgggttt | gcaagttttt | aaaaccaata | agaatgtgac | attagacccc | 960 |
| aaagatatcc | ctggattagc | agaggcaggg | tggctggaag | aaatggataa | attagcacaa | 1020 |
| aaaccgaaaa | gaggaccaca | ttataacttt | atggttacgc | tattcagtga | aattcagaac | 1080 |
| cacccttctg | cttggccatt | tgcagtggca | gtcaacaaag | aagaagtacc | agattattat | 1140 |
| cgagttattg | aacatccaat | tgatttggca | acaatagaac | aaaaattgga | aaacaacttg | 1200 |
| tatttaaaat | ttactgatttt | tgtggatgat | ctaaaactaa | tgttcaacaa | ttgtcgagct | 1260 |
| tataattcgg | aaaccacaac | atattataaa | acgcaaaata | aactagaaaa | gtttatgaat | 1320 |
| aataaattga | aagactgtag | ttttgtatag | | | | 1350 |

<210> SEQ ID NO 76
<211> LENGTH: 672
<212> TYPE: DNA
<213> ORGANISM: Saccharomyces cerevisiae

<400> SEQUENCE: 76

| | | | | | |
|---|---|---|---|---|---|
| agttcgagtt | tatcattatc | aatactgcca | tttcaaagaa | tacgtaaata | attaatagta | 60 |
| gtgattttcc | taactttatt | tagtcaaaaa | attagccttt | taattctgct | gtaacccgta | 120 |
| catgcccaaa | ataggggggcg | ggttacacag | aatatataac | atcgtaggtg | tctgggtgaa | 180 |
| cagtttattc | ctggcatcca | ctaaatataa | tggagcccgc | ttttaagct | ggcatccaga | 240 |
| aaaaaaaga | atcccagcac | caaaatattg | ttttcttcac | caaccatcag | ttcataggtc | 300 |
| cattctctta | gcgcaactac | agagaacagg | ggcacaaaca | ggcaaaaaac | gggcacaacc | 360 |
| tcaatggagt | gatgcaacct | gcctggagta | aatgatgaca | caaggcaatt | gacccacgca | 420 |

| | |
|---|---|
| tgtatctatc tcattttctt acaccttcta ttaccttctg ctctctctga tttggaaaaa | 480 |
| gctgaaaaaa aaggttgaaa ccagttccct gaaattattc ccctacttga ctaataagta | 540 |
| tataaagacg gtaggtattg attgtaattc tgtaaatcta tttcttaaac ttcttaaatt | 600 |
| ctactttat agttagtctt ttttttagtt ttaaaacacc aagaacttag tttcgaataa | 660 |
| acacacataa ac | 672 |

<210> SEQ ID NO 77
<211> LENGTH: 270
<212> TYPE: DNA
<213> ORGANISM: Saccharomyces cerevisiae

<400> SEQUENCE: 77

| | |
|---|---|
| gacctcgagt catgtaatta gttatgtcac gcttacattc acgccctccc cccacatccg | 60 |
| ctctaaccga aaaggaagga gttagacaac ctgaagtcta ggtccctatt tatttttta | 120 |
| tagttatgtt agtattaaga acgttattta tatttcaaat tttctttt tttctgtaca | 180 |
| gacgcgtgta cgcatgtaac attatactga aaaccttgct tgagaaggtt ttgggacgct | 240 |
| cgaaggcttt aatttgcggc cggtacccaa | 270 |

<210> SEQ ID NO 78
<211> LENGTH: 643
<212> TYPE: DNA
<213> ORGANISM: Saccharomyces cerevisiae

<400> SEQUENCE: 78

| | |
|---|---|
| gaaatgaata acaatactga cagtactaaa taattgccta cttggcttca catacgttgc | 60 |
| atacgtcgat atagataata atgataatga cagcaggatt atcgtaatac gtaatagttg | 120 |
| aaaatctcaa aaatgtgtgg gtcattacgt aaataatgat aggaatggga ttcttctatt | 180 |
| tttccttttt ccattctagc agccgtcggg aaaacgtggc atcctctctt tcgggctcaa | 240 |
| ttggagtcac gctgccgtga gcatcctctc tttccatatc taacaactga gcacgtaacc | 300 |
| aatggaaaag catgagctta gcgttgctcc aaaaaagtat tggatggtta ataccatttg | 360 |
| tctgttctct tctgactttg actcctcaaa aaaaaaaaat ctacaatcaa cagatcgctt | 420 |
| caattacgcc ctcacaaaaa ctttttttcct tcttcttcgc ccacgttaaa ttttatccct | 480 |
| catgttgtct aacggatttc tgcacttgat ttattataaa aagacaaaga cataatactt | 540 |
| ctctatcaat ttcagttatt gttcttcctt gcgttattct tctgttcttc ttttcttttt | 600 |
| gtcatatata accataacca agtaatacat attcaaatct aga | 643 |

<210> SEQ ID NO 79
<211> LENGTH: 760
<212> TYPE: DNA
<213> ORGANISM: Saccharomyces cerevisiae

<400> SEQUENCE: 79

| | |
|---|---|
| tcttttccga ttttttttcta aaccgtggaa tatttcggat atccttttgt tgtttccggg | 60 |
| tgtacaatat ggacttcctc ttttctggca accaaaccca tacatcggga ttcctataat | 120 |
| accttcgttg gtctccctaa catgtaggtg gcggagggga gatatacaat agaacagata | 180 |
| ccagacaaga cataatgggc taaacaagac tacaccaatt acactgcctc attgatggtg | 240 |
| gtacataacg aactaatact gtagccctag acttgatagc catcatcata tcgaagtttc | 300 |
| actacccttt ttccatttgc catctattga agtaataata ggcgcatgca acttcttttc | 360 |
| tttttttttc tttctctct cccccgttgt tgtctcacca tatccgcaat gacaaaaaaa | 420 |

```
tgatggaaga cactaaagga aaaaattaac gacaaagaca gcaccaacag atgtcgttgt    480
tccagagctg atgagggta tctcgaagca cacgaaactt tttccttcct tcattcacgc    540
acactactct ctaatgagca acggtatacg gccttccttc cagttacttg aatttgaaat    600
aaaaaaaagt tgctgtctt gctatcaagt ataaatagac ctgcaattat taatcttttg    660
tttcctcgtc attgttctcg ttcccttttct tccttgtttc tttttctgca caatatttca    720
agctatacca agcatacaat caactatctc atatacaatg                           760
```

<210> SEQ ID NO 80
<211> LENGTH: 316
<212> TYPE: DNA
<213> ORGANISM: Saccharomyces cerevisiae

<400> SEQUENCE: 80

```
gagtaagcga atttcttatg atttatgatt tttattatta ataagttat aaaaaaaata     60 agtgtataca aattttaaag tgactcttag gttttaaaac gaaaattctt attcttgagt   120
aactctttcc tgtaggtcag gttgctttct caggtatagc atgaggtcgc tcttattgac   180
cacacctcta ccggcatgcc gagcaaatgc ctgcaaatcg ctccccattt cacccaattg   240
tagatatgct aactccagca atgagttgat gaatctcggt gtgtatttta tgtcctcaga   300
ggacaacacc tgtggt                                                   316
```

<210> SEQ ID NO 81
<211> LENGTH: 753
<212> TYPE: DNA
<213> ORGANISM: Saccharomyces cerevisiae

<400> SEQUENCE: 81

```
gcatgcttgc atttagtcgt gcaatgtatg actttaagat ttgtgagcag gaagaaaagg    60
gagaatcttc taacgataaa cccttgaaaa actgggtaga ctacgctatg ttgagttgct   120
acgcaggctg cacaattaca cgagaatgct cccgcctagg atttaaggct aagggacgtg   180
caatgcagac gacagatcta aatgaccgtg tcggtgaagt gttcgccaaa cttttcggtt   240
aacacatgca gtgatgcacg cgcgatggtg ctaagttaca tatatatata tatagccata   300
gtgatgtcta agtaaccttt atggtatatt tcttaatgtg gaaagatact agcgcgcgca   360
cccacacaca agcttcgtct tttcttgaag aaaagaggaa gctcgctaaa tgggattcca   420
ctttccgttc cctgccagct gatggaaaaa ggttagtgga acgatgaaga ataaaagag   480 agatccactg aggtgaaatt tcagctgaca gcgagtttca tgatcgtgat gaacaatggt   540
aacgagttgt ggctgttgcc agggagggtg gttctcaact tttaatgtat ggccaaatcg   600
ctacttgggt ttgttatata acaaagaaga aataatgaac tgattctctt cctccttctt   660
gtcctttctt aattctgttg taattacctt cctttgtaat tttttttgta attattcttc   720
ttaataatcc aaacaaacac acatattaca ata                                753
```

<210> SEQ ID NO 82
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 82

```
cgtgttagtc acatcaggac                                                20
```

<210> SEQ ID NO 83
<211> LENGTH: 24
<212> TYPE: DNA
<213> ORGANISM: Artificial Sequence
<220> FEATURE:
<223> OTHER INFORMATION: Primer N98SeqF2

<400> SEQUENCE: 83
ggccatagca aaatccaaa cagc                                             24

<210> SEQ ID NO 84
<211> LENGTH: 24
<212> TYPE: DNA
<213> ORGANISM: Artificial Sequence
<220> FEATURE:
<223> OTHER INFORMATION: Primer N98SeqF3

<400> SEQUENCE: 84
ccacgatcaa tcatatcgaa cacg                                            24

<210> SEQ ID NO 85
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 85
ggtttctgtc tctggtgacg                                                 20

<210> SEQ ID NO 86
<211> LENGTH: 22
<212> TYPE: DNA
<213> ORGANISM: Artificial Sequence
<220> FEATURE:
<223> OTHER INFORMATION: Primer N99SeqR1

<400> SEQUENCE: 86
gtctggtgat tctacgcgca ag                                              22

<210> SEQ ID NO 87
<211> LENGTH: 22
<212> TYPE: DNA
<213> ORGANISM: Artificial Sequence
<220> FEATURE:
<223> OTHER INFORMATION: Primer N99SeqR2

<400> SEQUENCE: 87
catcgactgc attacgcaac tc                                              22

<210> SEQ ID NO 88
<211> LENGTH: 22
<212> TYPE: DNA
<213> ORGANISM: Artificial Sequence
<220> FEATURE:
<223> OTHER INFORMATION: Primer N99SeqR3

<400> SEQUENCE: 88
cgatcgtcag aacaacatct gc                                              22

<210> SEQ ID NO 89
<211> LENGTH: 20
<212> TYPE: DNA
<213> ORGANISM: Artificial Sequence
<220> FEATURE:
<223> OTHER INFORMATION: Primer N99SeqR4

```
<400> SEQUENCE: 89
ccttcagtgt tcgctgtcag                                              20

<210> SEQ ID NO 90
<211> LENGTH: 36
<212> TYPE: DNA
<213> ORGANISM: Artificial Sequence
<220> FEATURE:
<223> OTHER INFORMATION: Primer N136

<400> SEQUENCE: 90
ccgcggatag atctgaaatg aataacaata ctgaca                            36

<210> SEQ ID NO 91
<211> LENGTH: 65
<212> TYPE: DNA
<213> ORGANISM: Artificial Sequence
<220> FEATURE:
<223> OTHER INFORMATION: Primer N137

<400> SEQUENCE: 91
taccaccgaa gttgatttgc ttcaacatcc tcagctctag atttgaatat gtattacttg  60
gttat                                                              65

<210> SEQ ID NO 92
<211> LENGTH: 28
<212> TYPE: DNA
<213> ORGANISM: Artificial Sequence
<220> FEATURE:
<223> OTHER INFORMATION: Primer N138

<400> SEQUENCE: 92
atgttgaagc aaatcaactt cggtggta                                     28

<210> SEQ ID NO 93
<211> LENGTH: 22
<212> TYPE: DNA
<213> ORGANISM: Artificial Sequence
<220> FEATURE:
<223> OTHER INFORMATION: Primer N139

<400> SEQUENCE: 93
ttattggttt tctggtctca ac                                           22

<210> SEQ ID NO 94
<211> LENGTH: 57
<212> TYPE: DNA
<213> ORGANISM: Artificial Sequence
<220> FEATURE:
<223> OTHER INFORMATION: Primer N140

<400> SEQUENCE: 94
aagttgagac cagaaaacca ataattaatt aatcatgtaa ttagttatgt cacgctt     57

<210> SEQ ID NO 95
<211> LENGTH: 30
<212> TYPE: DNA
<213> ORGANISM: Artificial Sequence
<220> FEATURE:
<223> OTHER INFORMATION: Primer N141

<400> SEQUENCE: 95
gcggccgccc gcaaattaaa gccttcgagc                                   30
```

<210> SEQ ID NO 96
<211> LENGTH: 28
<212> TYPE: DNA
<213> ORGANISM: Artificial Sequence
<220> FEATURE:
<223> OTHER INFORMATION: Primer N142

<400> SEQUENCE: 96
ggatccgcat gcttgcattt agtcgtgc                                28

<210> SEQ ID NO 97
<211> LENGTH: 56
<212> TYPE: DNA
<213> ORGANISM: Artificial Sequence
<220> FEATURE:
<223> OTHER INFORMATION: N143

<400> SEQUENCE: 97
caggtaatcc cccacagtat acatcctcag ctattgtaat atgtgtgttt gtttgg    56

<210> SEQ ID NO 98
<211> LENGTH: 22
<212> TYPE: DNA
<213> ORGANISM: Artificial Sequence
<220> FEATURE:
<223> OTHER INFORMATION: Primer N144

<400> SEQUENCE: 98
atgtatactg tgggggatta cc                                      22

<210> SEQ ID NO 99
<211> LENGTH: 22
<212> TYPE: DNA
<213> ORGANISM: Artificial Sequence
<220> FEATURE:
<223> OTHER INFORMATION: Primer N145

<400> SEQUENCE: 99
ttagctttta ttttgctccg ca                                      22

<210> SEQ ID NO 100
<211> LENGTH: 57
<212> TYPE: DNA
<213> ORGANISM: Artificial Sequence
<220> FEATURE:
<223> OTHER INFORMATION: Primer N146

<400> SEQUENCE: 100
tttgcggagc aaaataaaag ctaattaatt aagagtaagc gaatttctta tgattta   57

<210> SEQ ID NO 101
<211> LENGTH: 28
<212> TYPE: DNA
<213> ORGANISM: Artificial Sequence
<220> FEATURE:
<223> OTHER INFORMATION: Primer N147

<400> SEQUENCE: 101
actagtacca caggtgttgt cctctgag                                28

<210> SEQ ID NO 102
<211> LENGTH: 22
<212> TYPE: DNA
<213> ORGANISM: Artificial Sequence
<220> FEATURE:
<223> OTHER INFORMATION: Primer N151

<400> SEQUENCE: 102
ctagagagct ttcgttttca tg        22

<210> SEQ ID NO 103
<211> LENGTH: 57
<212> TYPE: DNA
<213> ORGANISM: Artificial Sequence
<220> FEATURE:
<223> OTHER INFORMATION: Primer N152

<400> SEQUENCE: 103
ctcatgaaaa cgaaagctct ctagttaatt aatcatgtaa ttagttatgt cacgctt        57

<210> SEQ ID NO 104
<211> LENGTH: 25
<212> TYPE: DNA
<213> ORGANISM: Artificial Sequence
<220> FEATURE:
<223> OTHER INFORMATION: Primer N155

<400> SEQUENCE: 104
atggcaaaga agctcaacaa gtact        25

<210> SEQ ID NO 105
<211> LENGTH: 22
<212> TYPE: DNA
<213> ORGANISM: Artificial Sequence
<220> FEATURE:
<223> OTHER INFORMATION: Primer N156

<400> SEQUENCE: 105
tcaagcatct aaaacacaac cg        22

<210> SEQ ID NO 106
<211> LENGTH: 57
<212> TYPE: DNA
<213> ORGANISM: Artificial Sequence
<220> FEATURE:
<223> OTHER INFORMATION: Primer N157

<400> SEQUENCE: 106
aacggttgtg ttttagatgc ttgattaatt aagagtaagc gaatttctta tgattta        57

<210> SEQ ID NO 107
<211> LENGTH: 28
<212> TYPE: DNA
<213> ORGANISM: Artificial Sequence
<220> FEATURE:
<223> OTHER INFORMATION: Primer N158

<400> SEQUENCE: 107
ggatcctttt ctggcaacca aacccata        28

<210> SEQ ID NO 108
<211> LENGTH: 56
<212> TYPE: DNA
<213> ORGANISM: Artificial Sequence
<220> FEATURE:
<223> OTHER INFORMATION: Primer N159

<400> SEQUENCE: 108
cgagtacttg ttgagcttct ttgccatcct cagcgagata gttgattgta tgcttg        56

<210> SEQ ID NO 109

```
<211> LENGTH: 19
<212> TYPE: DNA
<213> ORGANISM: Artificial Sequence
<220> FEATURE:
<223> OTHER INFORMATION: Primer N160SeqF1

<400> SEQUENCE: 109
gaaaacgtgg catcctctc                                                19

<210> SEQ ID NO 110
<211> LENGTH: 19
<212> TYPE: DNA
<213> ORGANISM: Artificial Sequence
<220> FEATURE:
<223> OTHER INFORMATION: Primer N160SeqF2

<400> SEQUENCE: 110
gctgactggc aagagaaa                                                 19

<210> SEQ ID NO 111
<211> LENGTH: 20
<212> TYPE: DNA
<213> ORGANISM: Artificial Sequence
<220> FEATURE:
<223> OTHER INFORMATION: Primer N160SeqF3

<400> SEQUENCE: 111
tgtacttctc ccacggtttc                                               20

<210> SEQ ID NO 112
<211> LENGTH: 22
<212> TYPE: DNA
<213> ORGANISM: Artificial Sequence
<220> FEATURE:
<223> OTHER INFORMATION: Primer N160SeqF4

<400> SEQUENCE: 112
agctacccaa tctctatacc ca                                            22

<210> SEQ ID NO 113
<211> LENGTH: 22
<212> TYPE: DNA
<213> ORGANISM: Artificial Sequence
<220> FEATURE:
<223> OTHER INFORMATION: Primer N160SeqF5

<400> SEQUENCE: 113
cctgaagtct aggtccctat tt                                            22

<210> SEQ ID NO 114
<211> LENGTH: 19
<212> TYPE: DNA
<213> ORGANISM: Artificial Sequence
<220> FEATURE:
<223> OTHER INFORMATION: N160SeqR1

<400> SEQUENCE: 114
gcgtgaatgt aagcgtgac                                                19

<210> SEQ ID NO 115
<211> LENGTH: 20
<212> TYPE: DNA
<213> ORGANISM: Artificial Sequence
<220> FEATURE:
<223> OTHER INFORMATION: Primer N160SeqR2

<400> SEQUENCE: 115
```
cgtcgtattg agccaagaac                                               20

<210> SEQ ID NO 116
<211> LENGTH: 20
<212> TYPE: DNA
<213> ORGANISM: Artificial Sequence
<220> FEATURE:
<223> OTHER INFORMATION: Primer N160SeqR3

<400> SEQUENCE: 116
gcatcggaca acaagttcat                                               20

<210> SEQ ID NO 117
<211> LENGTH: 22
<212> TYPE: DNA
<213> ORGANISM: Artificial Sequence
<220> FEATURE:
<223> OTHER INFORMATION: Primer N160SeqR4

<400> SEQUENCE: 117
tcgttcttga agtagtccaa ca                                            22

<210> SEQ ID NO 118
<211> LENGTH: 19
<212> TYPE: DNA
<213> ORGANISM: Artificial Sequence
<220> FEATURE:
<223> OTHER INFORMATION: Primer N160SeqR5

<400> SEQUENCE: 118
tgagcccgaa agagaggat                                                19

<210> SEQ ID NO 119
<211> LENGTH: 19
<212> TYPE: DNA
<213> ORGANISM: Artificial Sequence
<220> FEATURE:
<223> OTHER INFORMATION: Primer N161SeqF1

<400> SEQUENCE: 119
acggtatacg gccttcctt                                                19

<210> SEQ ID NO 120
<211> LENGTH: 20
<212> TYPE: DNA
<213> ORGANISM: Artificial Sequence
<220> FEATURE:
<223> OTHER INFORMATION: Primer N161SeqF2

<400> SEQUENCE: 120
gggtttgaaa gctatgcagt                                               20

<210> SEQ ID NO 121
<211> LENGTH: 22
<212> TYPE: DNA
<213> ORGANISM: Artificial Sequence
<220> FEATURE:
<223> OTHER INFORMATION: Primer N161SeqF3

<400> SEQUENCE: 121
ggtggtatgt atactgccaa ca                                            22

<210> SEQ ID NO 122
<211> LENGTH: 22
<212> TYPE: DNA

```
<213> ORGANISM: Artificial Sequence
<220> FEATURE:
<223> OTHER INFORMATION: Primer N161SeqF4

<400> SEQUENCE: 122
ggtggtaccc aatctgtgat ta                                            22

<210> SEQ ID NO 123
<211> LENGTH: 20
<212> TYPE: DNA
<213> ORGANISM: Artificial Sequence
<220> FEATURE:
<223> OTHER INFORMATION: Primer N161SeqF5

<400> SEQUENCE: 123
cggtttgggt aaagatgttg                                               20

<210> SEQ ID NO 124
<211> LENGTH: 22
<212> TYPE: DNA
<213> ORGANISM: Artificial Sequence
<220> FEATURE:
<223> OTHER INFORMATION: Primer N161SeqF6

<400> SEQUENCE: 124
aaacgaaaat tcttattctt ga                                            22

<210> SEQ ID NO 125
<211> LENGTH: 22
<212> TYPE: DNA
<213> ORGANISM: Artificial Sequence
<220> FEATURE:
<223> OTHER INFORMATION: Primer N161SeqR1

<400> SEQUENCE: 125
tcgttttaaa acctaagagt ca                                            22

<210> SEQ ID NO 126
<211> LENGTH: 19
<212> TYPE: DNA
<213> ORGANISM: Artificial Sequence
<220> FEATURE:
<223> OTHER INFORMATION: Primer N161SeqR2

<400> SEQUENCE: 126
ccaaaccgta acccatcag                                                19

<210> SEQ ID NO 127
<211> LENGTH: 19
<212> TYPE: DNA
<213> ORGANISM: Artificial Sequence
<220> FEATURE:
<223> OTHER INFORMATION: Primer N161SeqR3

<400> SEQUENCE: 127
cacagattgg gtaccacca                                                19

<210> SEQ ID NO 128
<211> LENGTH: 20
<212> TYPE: DNA
<213> ORGANISM: Artificial Sequence
<220> FEATURE:
<223> OTHER INFORMATION: Primer N161Seqr4

<400> SEQUENCE: 128
accacaagaa ccaggacctg                                               20
```

<210> SEQ ID NO 129
<211> LENGTH: 19
<212> TYPE: DNA
<213> ORGANISM: Artificial Sequence
<220> FEATURE:
<223> OTHER INFORMATION: Primer N161SeqR5

<400> SEQUENCE: 129
catagctttc aaacccgct                                                 19

<210> SEQ ID NO 130
<211> LENGTH: 22
<212> TYPE: DNA
<213> ORGANISM: Artificial Sequence
<220> FEATURE:
<223> OTHER INFORMATION: Primer N161SeqR6

<400> SEQUENCE: 130
cgtataccgt tgctcattag ag                                             22

<210> SEQ ID NO 131
<211> LENGTH: 23
<212> TYPE: DNA
<213> ORGANISM: Artificial Sequence
<220> FEATURE:
<223> OTHER INFORMATION: Primer N162

<400> SEQUENCE: 131
atgttgacaa aagcaacaaa aga                                            23

<210> SEQ ID NO 132
<211> LENGTH: 38
<212> TYPE: DNA
<213> ORGANISM: Artificial Sequence
<220> FEATURE:
<223> OTHER INFORMATION: Primer N189

<400> SEQUENCE: 132
atccgcggat agatctagtt cgagtttatc attatcaa                            38

<210> SEQ ID NO 133
<211> LENGTH: 53
<212> TYPE: DNA
<213> ORGANISM: Artificial Sequemce
<220> FEATURE:
<223> OTHER INFORMATION: Primer N190.1

<400> SEQUENCE: 133
ttcttttgtt gcttttgtca acatcctcag cgtttatgtg tgtttattcg aaa           53

<210> SEQ ID NO 134
<211> LENGTH: 38
<212> TYPE: DNA
<213> ORGANISM: Artificial Sequence
<220> FEATURE:
<223> OTHER INFORMATION: Primer N176

<400> SEQUENCE: 134
atccgcggat agatctatta gaagccgccg agcgggcg                            38

<210> SEQ ID NO 135
<211> LENGTH: 31
<212> TYPE: DNA
<213> ORGANISM: Artificial Sequence
<220> FEATURE:

<223> OTHER INFORMATION: Primer N177

<400> SEQUENCE: 135
atcctcagct tttctccttg acgttaaagt a                                        31

<210> SEQ ID NO 136
<211> LENGTH: 38
<212> TYPE: DNA
<213> ORGANISM: Artificial Sequence
<220> FEATURE:
<223> OTHER INFORMATION: Primer N191

<400> SEQUENCE: 136
atccgcggat agatctccca ttaccgacat ttgggcgc                                 38

<210> SEQ ID NO 137
<211> LENGTH: 31
<212> TYPE: DNA
<213> ORGANISM: Artificial Sequence
<220> FEATURE:
<223> OTHER INFORMATION: Primer N192

<400> SEQUENCE: 137
atcctcagcg atgattgatt gattgattgt a                                        31

<210> SEQ ID NO 138
<211> LENGTH: 1474
<212> TYPE: DNA
<213> ORGANISM: artificial sequence
<220> FEATURE:
<223> OTHER INFORMATION: constructed URA3 gene bounded by repeats

<400> SEQUENCE: 138
gcattgcgga ttacgtattc taatgttcag cccgcggaac gccagcaaat caccacccat        60
gcgcatgata ctgagtcttg tacacgctgg gcttccagtg tactgagagt gcaccatacc       120
acagcttttc aattcaattc atcatttttt ttttattctt ttttttgatt tcggtttctt       180
tgaaattttt ttgattcggt aatctccgaa cagaaggaag aacgaaggaa ggagcacaga       240
cttagattgg tatatatacg catatgtagt gttgaagaaa catgaaattg cccagtattc       300
ttaacccaac tgcacagaac aaaaacctgc aggaaacgaa gataaatcat gtcgaaagct       360
acatataagg aacgtgctgc tactcatcct agtcctgttg ctgccaagct atttaatatc       420
atgcacgaaa agcaaacaaa cttgtgtgct tcattggatg ttcgtaccac caaggaatta       480
ctggagttag ttgaagcatt aggtcccaaa atttgtttac taaaaacaca tgtggatatc       540
ttgactgatt tttccatgga gggcacagtt aagccgctaa aggcattatc cgccaagtac       600
aattttttac tcttcgaaga cagaaaattt gctgacattg gtaatacagt caaattgcag       660
tactctgcgg gtgtatacag aatagcagaa tgggcagaca ttacgaatgc acacggtgtg       720
gtgggcccag gtattgttag cggtttgaag caggcggcag aagaagtaac aaaggaacct       780
agaggccttt tgatgttagc agaattgtca tgcaagggct ccctatctac tggagaatat       840
actaagggta ctgttgacat tgcgaagagc gacaaagatt tgttatcgg ctttattgct       900
caaagagaca tgggtggaag agatgaaggt tacgattggt tgattatgac acccggtgtg       960
ggtttagatg acaagggaga cgcattgggt caacagtata gaaccgtgga tgatgtggtc      1020
tctacaggat ctgacattat tattgttgga agaggactat ttgcaaaggg aagggatgct      1080
aaggtagagg tgaacgttac agaaaagca ggctgggaag catatttgag aagatgcggc      1140
cagcaaaact aaaaaactgt attataagta aatgcatgta tactaaactc acaaattaga      1200

```
gcttcaattt aattatatca gttattaccc tatgcggtgt gaaataccgc acagatgcgt    1260
aaggagaaaa taccgcatca ggaaattgta aacgttaata ttttgttaaa attcgcgtta    1320 aattttgtt aaatcagctc attttttaac caataggccg aaatcggcaa aatcttcagc     1380
ccgcggaacg ccagcaaatc accacccatg cgcatgatac tgagtcttgt acacgctggg    1440
cttccagtga tgatacaacg agttagccaa ggtg    1474
```

```
<210> SEQ ID NO 139
<211> LENGTH: 75
<212> TYPE: DNA
<213> ORGANISM: artificial sequence
<220> FEATURE:
<223> OTHER INFORMATION: synthetic primer

<400> SEQUENCE: 139
ctttacattg ttggaaagcc tcgttgtctt ttaagatttt ataagcattg gcattgcgga    60
ttacgtattc taatg    75
```

```
<210> SEQ ID NO 140
<211> LENGTH: 76
<212> TYPE: DNA
<213> ORGANISM: artificial sequence
<220> FEATURE:
<223> OTHER INFORMATION: synthetic primer

<400> SEQUENCE: 140
tgaattagat gaatcagcta gcctaaatat agtatctaag acattgtata caccttggct    60
aactcgttgt atcatc    76
```

```
<210> SEQ ID NO 141
<211> LENGTH: 75
<212> TYPE: DNA
<213> ORGANISM: artificial sequence
<220> FEATURE:
<223> OTHER INFORMATION: synthetic primer

<400> SEQUENCE: 141
ataaaaattt ccctatacta tcattaatta aatcattatt attactaaag gcattgcgga    60
ttacgtattc taatg    75
```

```
<210> SEQ ID NO 142
<211> LENGTH: 76
<212> TYPE: DNA
<213> ORGANISM: artificial sequence
<220> FEATURE:
<223> OTHER INFORMATION: synthetic primer

<400> SEQUENCE: 142
aaattggcat aaaaaagatt aaattcttat ctaagtgaat gtatctatttt caccttggct    60 aactcgttgt atcatc    76
```

```
<210> SEQ ID NO 143
<211> LENGTH: 25
<212> TYPE: DNA
<213> ORGANISM: artificial sequence
<220> FEATURE:
<223> OTHER INFORMATION: primer binding sequence

<400> SEQUENCE: 143
gcattgcgga ttacgtattc taatg    25
```

```
<210> SEQ ID NO 144
<211> LENGTH: 26
<212> TYPE: DNA
<213> ORGANISM: artificial sequence
<220> FEATURE:
<223> OTHER INFORMATION: primer binding sequence

<400> SEQUENCE: 144
gatgatacaa cgagttagcc aaggtg                                             26

<210> SEQ ID NO 145
<211> LENGTH: 75
<212> TYPE: DNA
<213> ORGANISM: artificial sequence
<220> FEATURE:
<223> OTHER INFORMATION: direct repeat sequence

<400> SEQUENCE: 145
ttcagcccgc ggaacgccag caaatcacca cccatgcgca tgatactgag tcttgtacac        60
gctgggcttc cagtg                                                         75

<210> SEQ ID NO 146
<211> LENGTH: 75
<212> TYPE: DNA
<213> ORGANISM: artificial sequence
<220> FEATURE:
<223> OTHER INFORMATION: direct repeat sequence

<400> SEQUENCE: 146
ttcagcccgc ggaacgccag caaatcacca cccatgcgca tgatactgag tcttgtacac        60
gctgggcttc cagtg                                                         75

<210> SEQ ID NO 147
<211> LENGTH: 200
<212> TYPE: DNA
<213> ORGANISM: artificial sequence
<220> FEATURE:
<223> OTHER INFORMATION: promoter to express URA3

<400> SEQUENCE: 147 tttttttattc tttttttga tttcggtttc tttgaaattt ttttgattcg gtaatctccg        60
aacagaagga agaacgaagg aaggagcaca gacttagatt ggtatatata cgcatatgta       120
gtgttgaaga acatgaaat tgcccagtat tcttaaccca actgcacaga acaaaaacct        180
gcaggaaacg aagataaatc                                                   200

<210> SEQ ID NO 148
<211> LENGTH: 804
<212> TYPE: DNA
<213> ORGANISM: artificial sequence
<220> FEATURE:
<223> OTHER INFORMATION: coding region for URA3

<400> SEQUENCE: 148
atgtcgaaag ctacatataa ggaacgtgct gctactcatc ctagtcctgt tgctgccaag        60
ctatttaata tcatgcacga aaagcaaaca aacttgtgtg cttcattgga tgttcgtacc       120
accaaggaat tactggagtt agttgaagca ttaggtccca aaatttgttt actaaaaaca       180
catgtggata tcttgactga ttttttccatg gagggcacag ttaagccgct aaaggcatta       240
tccgccaagt acaattttt actcttcgaa gacagaaaat ttgctgacat tggtaataca       300
gtcaaattgc agtactctgc gggtgtatac agaatagcag aatgggcaga cattacgaat       360
```

```
gcacacggtg tggtgggccc aggtattgtt agcggtttga agcaggcggc agaagaagta    420
acaaaggaac ctagaggcct tttgatgtta gcagaattgt catgcaaggg ctccctatct    480
actggagaat atactaaggg tactgttgac attgcgaaga gcgacaaaga ttttgttatc    540
ggctttattg ctcaaagaga catgggtgga agagatgaag gttacgattg gttgattatg    600
acacccggtg tgggtttaga tgacaaggga gacgcattgg gtcaacagta tagaaccgtg    660
gatgatgtgg tctctacagg atctgacatt attattgttg gaagaggact atttgcaaag    720
ggaagggatg ctaaggtaga gggtgaacgt tacagaaaag caggctggga agcatatttg    780
agaagatgcg gccagcaaaa ctaa                                          804
```